United States Patent [19]
Wallace et al.

[11] Patent Number: 6,096,874
[45] Date of Patent: Aug. 1, 2000

[54] HIGH AFFINITY TAMOXIFEN DERIVATIVES

[75] Inventors: Sidney Wallace, Houston; David Yang, Sugar Land; E. Delpassand, Bellaire; A. Cherif, Houston; S. Quadri, Houston, all of Tex.

[73] Assignee: Board of Regents, the University of Texas System, Austin, Tex.

[21] Appl. No.: 08/477,525

[22] Filed: Jun. 7, 1995

Related U.S. Application Data

[63] Continuation-in-part of application No. 07/976,692, Nov. 13, 1992, abandoned, which is a continuation-in-part of application No. 07/589,928, Oct. 11, 1990, Pat. No. 5,219,548.

[51] Int. Cl.$^7$ .............................. C07F 13/00; C07F 5/00; C07C 211/00; C07C 221/00
[52] U.S. Cl. ................................. 534/10; 534/14; 534/15; 534/16; 564/316; 564/319
[58] Field of Search ............................ 564/316, 319, 564/321; 534/10, 14, 15, 16

[56] References Cited

U.S. PATENT DOCUMENTS

| | | | |
|---|---|---|---|
| 3,288,806 | 11/1966 | De Wald et al. | 260/326.5 |
| 4,696,949 | 9/1987 | Toivola et al. | 514/648 |
| 4,806,685 | 2/1989 | Abraham et al. | 564/324 |
| 4,839,155 | 6/1989 | McCague | 424/1.1 |
| 5,192,525 | 3/1993 | Yang et al. | 424/1.1 |
| 5,219,548 | 6/1993 | Yang et al. | 424/1.1 |

FOREIGN PATENT DOCUMENTS

| | | |
|---|---|---|
| 0054168 | of 1980 | European Pat. Off. . |
| 0260066 | of 1988 | European Pat. Off. . |

OTHER PUBLICATIONS

PCT Search Report mailed Sep. 12, 1996.
Allen et al., "Evidence for the Metabolic Activation of Non–Steroidal Antioestrogens: A Study of Structure–Activity relationships", *J. Pharmac*, 71:83–91, 1980.
Bezwoda et al., "The Value of Estrogen and Progesterone Receptor Determinations in Advanced Breast Cancer", *Cancer*, 68:867–872, 1991.
Fernandez et al., "Activated Oestrogen Receptors in Breast Cancer and Response to Endocrine Therapy", 20(1):41–46, 1984.

(List continued on next page.)

*Primary Examiner*—Gary E. Hollinden
*Assistant Examiner*—Lara C. Kelley
*Attorney, Agent, or Firm*—Arnold, White & Durkee

[57] ABSTRACT

The synthesis of tamoxifen derivatives, most particularly halo, halo alkyl, hydroxy, and amino tamoxifen derivatives is disclosed. The native tamoxifen molecule includes a substituted chemical group positioned on the aliphatic chain of the tamoxifen molecule. Particular tamoxifen derivatives of the invention include chloro, bromo, iodo, fluoro, amino and DTPA tamoxifen derivatives, and corresponding lower alkyl halogenated forms. The halogenated tamoxifen derivatives possess superior binding affinities for estrogen receptor rich tissues, such as uterine tissue and breast tissue, relative to unsubstituted native tamoxifen. Radiolabeled forms of the tamoxifen derivatives may be used as highly specific imaging agents for estrogen receptor rich tissues. The fluoro and bromo tamoxifen derivatives are particularly useful for imaging estrogen receptors by PET whereas the iodinated tamoxifens are particularly useful in imaging estrogen receptors by SPECT. Rapid and efficient methods of preparing the tamoxifen derivatives having high specific activity (>6 Ci/$\mu$mol) are also disclosed. Aliphatic chain substituted tamoxifen derivatives are shown to possess greater estrogen receptor binding affinity and more potent tumor cell inhibition than tamoxifen or tamoxifen derivatives substituted at other locations on the molecule (i.e., non-aliphatic chain substituted tamoxifen). The tanioxifen derivatives of the present invention may advantageously be used as anti-cancer therapeutic agents to halt estrogen-receptor positive tumors, such as those of breast and uterine tissue. The present invention also provides a hydrophilic DTPA-tamoxifen analogue, and uses thereof in imaging estrogen receptor positive ER+ lesions.

37 Claims, 49 Drawing Sheets

OTHER PUBLICATIONS

Hamacher et al., "Efficient Stereospecific Synthesis of No–Carrier–Added 2–[$^{18}$F]–Fluoro–2–Deoxy–D–Glucose Using Aminopolyther Supported Nucleophilic Substitution", *J. Nucl Med*, 27:235–238, 1986.

"Iodine–125–Labeled Estradiol: A Gamma–Emitting Analog of Estradiol that Binds to the Estrogen Receptor", *Science*, 205:1138–1140, 1979.

Kiesewetter et al., Preparation of Four Fluorine–18–Labeled Estrogens and Their Selective Uptakes in Target Tissues of Immature Rats, *The Journal of Nuclear Medicine*, 25(11):1212–1221, 1984.

Lien et al., "Distribution of Tamoxifen and its Metabolites in Rat and Human Tissues during Steady–State Treatment", *Cancer Research*, 51:4837–4844, 1991.

McCague et al., "Nonisomerizable Analogues of (Z)– and (E)–4–Hydroxytamoxifen. Synthesis abd Endocrinological Properties of Substituted Diphenylbenzocycloheptenes", *J. Med. Chem*, 31:1285–1290, 1988.

McElvany et al., "16α–[$^{77}$Br]Bromoestradiol: Dosimetry and Preliminary Clinical Studies", *J Nucl Med*, 23:425–430, 1982.

McGuire et al., "Positron Tomographic Assessment of 16α–[$^{18}$F] Fluoro–17β–Estradiol Uptake in Metastatic Breast Carcinoma", *J. Nucl Med*, 32(8):1526–1531, Aug. 1991.

Mosmann, Tim, "Rapid Colorimetric Assay for Cellular Growth and Survival: Applications to Proliferation and Cytotoxicity Assays", *Journal of Immunological Methods*, 65:55–63, 1983.

Pollack et al., "Effect of Tamoxifen on DNA Synthesis and Proliferation of Human Malignant Glioma Lines in Vitro", *Cancer Research*, 50:7134–7138, Nov. 1990.

Salituro et al., "Iododesethyl Tamoxifen Aziridine: Synthesis and Covalent Labeling of the Estrogen Receptor with an Iodine–Labeled Affinity Label", *Steroids*, 48(5–6):287–313.

Schneider et al., "1,1,2–Triphenylbut–1–enes: Relationship between Structure, Estradiol Receptor Affinity, and Mammary Tumor Inhibiting Properties", *J. Med. Chem.*, 25:1070–1077, 1982.

Tsai et al., "Antagonism of Development and Growth of 7,12–Dimethylbenz(a) anthracene–induced Rat Mammary Tumors by the Antiestrogen U 23,469 and Effects on Estrogen and Progesterone Receptors", *Cancer Research*, 27:1537–1543, 1977.

Wiseman et al., "Tamoxifen Inhibits Lipid Peroxidation in Cardiac Microsomes: Comparison with Liver Microsomes and Potential Relevance to the Cardiovascular Benefits Associated with Cancer Prevention and Treatment by Tamoxifen", *Biochemical Pharmacology*, 45(9):1851–1855, 1993.

Wiseman et al., "Protective Actions of Tamoxifen and 4–hydroxytamoxifen Against Oxidative Damage to Hman Low–Density Lipoproteins: A Mechanism Accounting for the Cardioprotective Action of Tamoxifen", *Biochem J.*, 292:35–638, 1993.

Yang et al., "Halogenated Analogues of Tamoxifen: Synthesis, Receptor Assay, and Inhibition of MCF7 Cells", *Journal of Pharmaceutical Sciences*, 81(7):622–625, Jul. 1992.

Yang et al., "Imaging, Biodistribution and Therapy Potential of Halogenated Tamoxifen Analogues", *Life Sciences*, 55(1):53–67, 1994.

Hanson et al. (1982), *Int. J. Nucl. Med. Biol.*, 9:105–107.

Loser et al. (1985), *Eur. J. Cancer Clin. Oncol.*, 21(8):985–990.

Yang et al. (Jun. 11, 1991), *The Society of Nuclear Medicine 38th Annual Meeting Cincinnati Convention Center*, No. 12071.

Tansey et al. (Jun. 11, 1991), *The Society of Nuclear Medicine 38th Annual Meeting Cincinnati Convention Center*, No. 32680.

Yang et al. (Jun. 30, 1992) *International Conference on Long– Term Antihormonal Therapy for Breast Cancer*.

Foster et al. (1986) *Anti–Cancer Drug Design*, 1:245–257.

Francesco et al. (1986) *Steroids*, 48(5–6):287–313.

International Search Report (1992).

Watanabe et al. (1989) *Journal of Chromatography*, 497:169–180.

D'Argy et al. (1989) *Chemical Abstracts*, 110(3):259, Abstract No. 20581h.

Kangus et al. (1989) *Chemical Abstracts*, 110(25):10, Abstract No. 224948t.

Hannu et al. (1990) Chemical Abstracts, 113(17):Abstract No. 144793k.

DeGregorio et al (1987), *Cancer Chemother Pharmacol* 20:316–381.

Kallio et al (1986), *Cancer Chemother Pharmacol* 17:103–108.

Robertson et al (1982), *J. Org. Chem.* 47:2387–2393.

Katzenellenbogen et al (1984), *Cancer Research* 44:112–119.

Kuroda, et al (1985), *J. Med. Chem* 28:1497–1503.

Ram et al (1989), *Journal of Labelled Compounds and Radiopharmaceuticals*, 27(6):661–668.

Pomper et al (1988), *J. Med Chem.*, 31:1360–1363.

Armstrong (1987), *Journal of Chromatography*, 414:492–196.

Lien et al (1987), *Clin. Chem.* 33(9):1608–1614.

Yang et al (1991), *Pharmaceutical Research*, 8(2):174–177.

Shani et al (1979), *Cancer Treat Rep. (USA)*, 63 (7):Abstract No. 366.

Shani et al (1985), *Med. Chem.* 28:1504–1511.

Mintun et al (1988), *Radiology*, 169:45–48.

Foster et al (1985), *J. Med. Chem.* 28 (10):1491–1497.

Kangas et al (1986), *Cancer Chemother Pharmacol* 17:109–113.

DeGregorio et al (1989), *Cancer Chemother Pharmacol* 23:68–70.

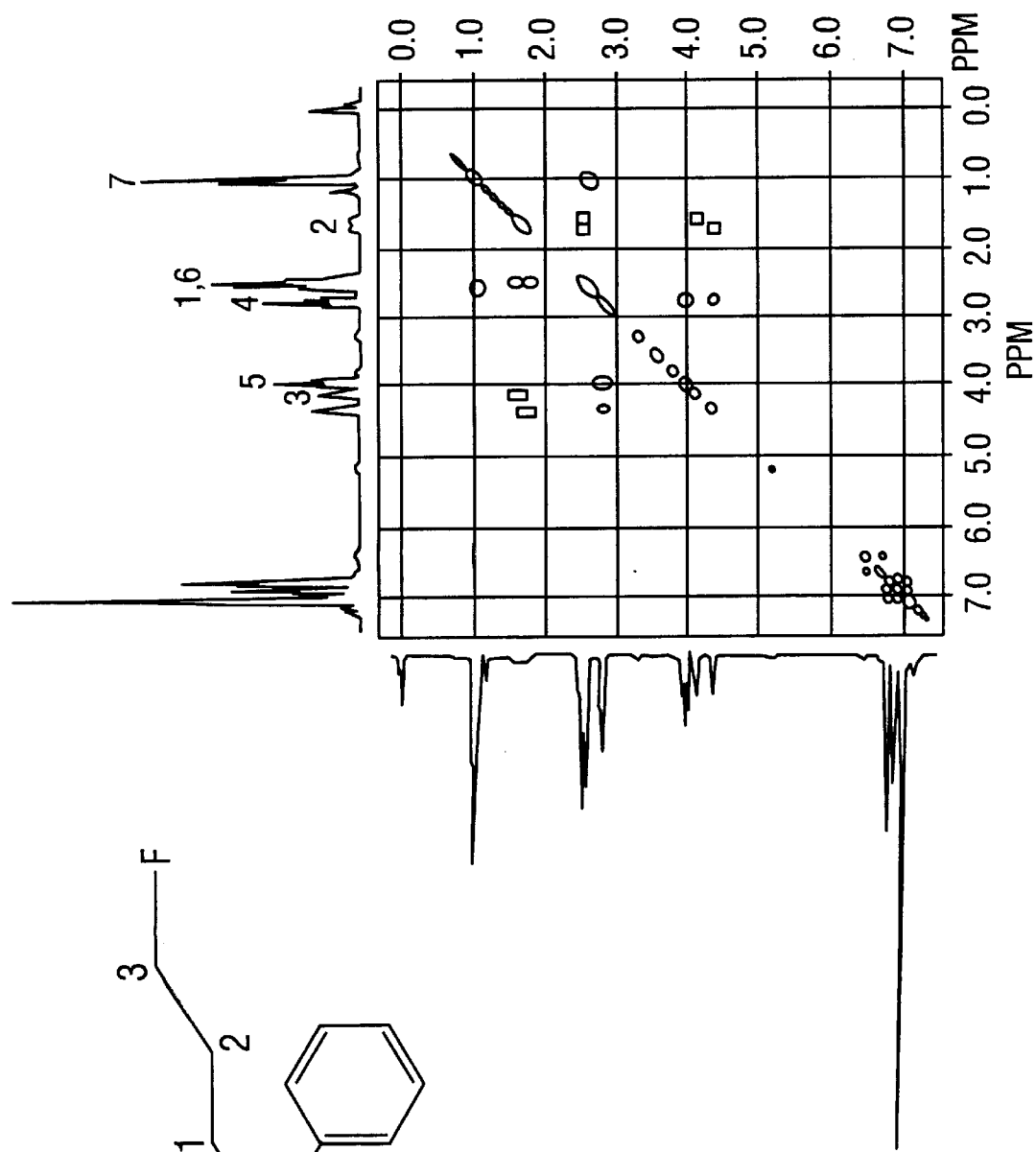
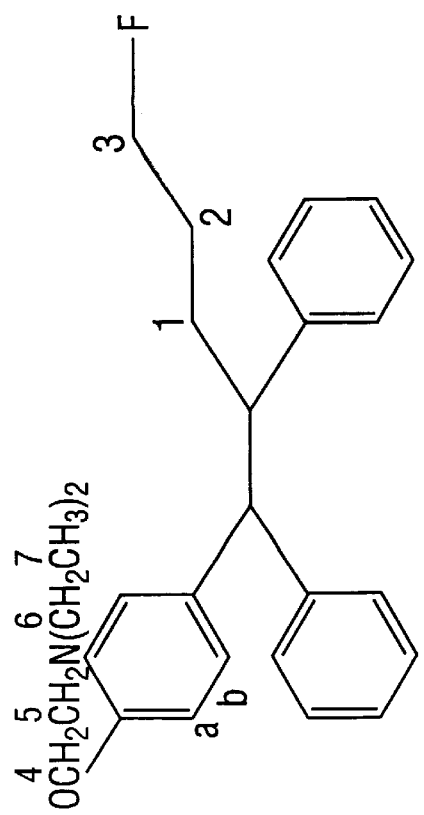
FIG. 6A
FIG. 6B

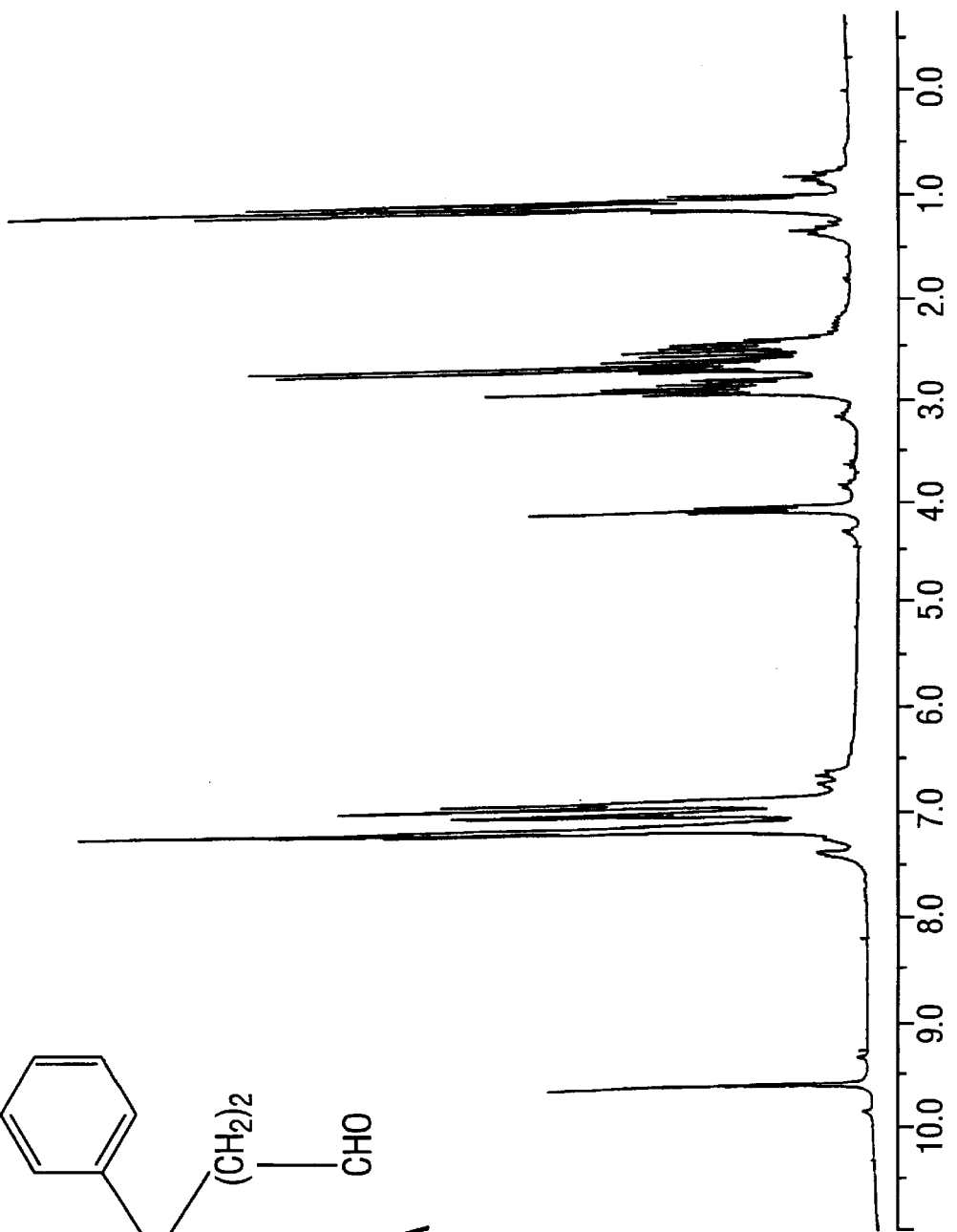
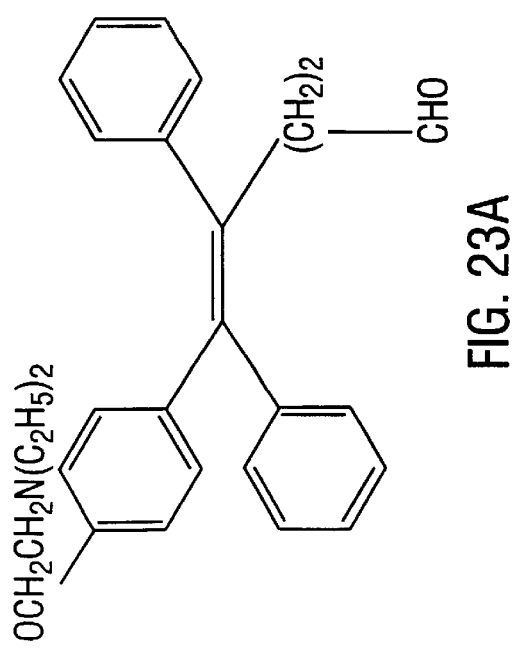
FIG. 23A
FIG. 23B

30 Min.

2 Hours

4 Hours

24 Hours

48 Hours

30 Min.

2 Hours

4 Hours

24 Hours

48 Hours

CONTROL (ANT)
UTERUS CNTS: 2849
BKG CNTS: 296
MUSCLE CNTS: 855

BLOCKING (ANT)

CONTROL (POST)
UTERUS CNTS: 1619
BKG CNTS: 243
MUSCLE CNTS: 438

BLOCKING (POST)

30 Min.

2 Hours

4 Hours

24 Hours

48 Hours

30 Min.

4 Hours

48 Hours

30 Min.

2 Hours

4 Hours

24 Hours

48 Hours

4 Hours

24 Hours

HIGH AFFINITY TAMOXIFEN DERIVATIVES

The present application is a continuation-in-part application of Applicants application, U.S. Ser. No. 07/976,692, filed Nov. 13, 1992, now abandoned, which is a continuation-in-part of U.S. Ser. No. 07/589,928, filed Oct. 1, 1990, now U.S. Pat. No. 5,219,548. Applicants hereby claim priority to this earlier filed application.

BACKGROUND OF THE INVENTION

1. Field of the Invention

The present invention relates to the field of tamoxifen derivatives and analogs, particularly halogenated tamoxifen derivatives and analogs. In that novel tamoxifen derivatives are described wherein the aliphatic chain of the molecule is substituted with a halogen group, the present invention also relates to methods of synthesizing tamoxifen analogs and derivatives.

In that the described tamoxifen derivatives have high affinity for binding estrogen receptors and may be labeled with detectable "tagging" molecules, rendering labeled estrogen receptors highly visible through positron emission topography (PET), single photon emission computed tomography (SPECT) and magnetic resonance imagining (MRI) the present invention also relates to reagents, radiopharmaceuticals and techniques in the field of molecular imaging.

The halogenated tamoxifen derivatives of the present invention are advantageously used in the imaging of estrogen receptors, for example, in breast, ovarian, uterine and brain tissue and may therefore be useful in the diagnosis of estrogen-receptor positive cancers, meningiomas and endometriosis.

The present invention also relates to the field of anti-cancer therapeutic agents, particularly to methods of breast tumor therapy, in that the described high affinity of these halogenated (i.e., iodo-, fluoro-, bromo- and chloro-) tamoxifen derivatives for estrogen receptors may be advantageously used to treat estrogen-receptor positive tumors.

2. Background of the Invention

Endocrine therapy provides an important nonsurgical method for treatment for breast carcinoma. This type of therapy is still considered standard for certain subsets of patients, typically postmenopausal women whose primary tumors have high estrogen levels.[1-3] The synthesis of F-18 fluoroestradiol for application in diagnosing breast tumors in humans has recently been described.[4] Observation of significant changes in the binding of estrogen receptors in breast tumors were reported using PET. However, technical difficulties associated with estrogen receptor saturation in patients receiving tamoxifen, or other estrogen receptor antagonist, has been observed to decrease the sensitivity and accuracy of using an estrogen-based receptor tag in diagnosing and monitoring the progress of tumors in patients receiving such treatments.

Tamoxifen (1), a potent non-steroidal antiestrogen, has been widely used in the treatment of human breast tumors. Tamoxifen has few side effects when compared with other hormonal treatments. Tamoxifen is cytostatic (i.e, it prevents/inhibits cell growth), and exerts competitive inhibitory activity at the receptor level with estrogen. More specifically, the cytostatic activity of tamoxifen results from its ability to bind to cytoplasmic estrogen receptors and be translocated to cell nuclei, where cell proliferation is prevented.[1-3] Thus, tamoxifen is often administered as an anticancer agent.[6] For example, Foster et al.[6] describes the effect of various tamoxifen hydroxy-derivatives on the growth of MCF-7 breast cancer cell line in its native form. However, highly active in vitro hydroxy tamoxifen derivatives were found to be less active than tamoxifen in vivo against a DMBA-induced ER-positive tumor in rats and only slightly more active against a hormone dependent mammary tumor in mice.

Tamoxifen has a relatively low binding affinity for the estrogen receptor (ER). Attempts have therefore been made to synthesize tamoxifen derivatives having improved ER binding affinity and specificity to enhance its action as an anti-cancer therapeutic agent. The structure of tamoxifen is demonstrated as:

[Formula 1]

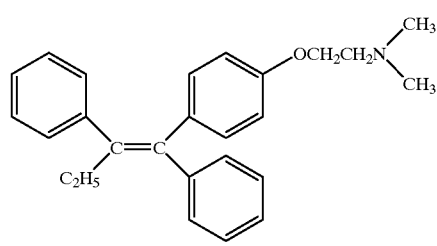

A variety of modified tamoxifen derivatives have been described in the literature. Structural modifications have been made at virtually every site on the three aromatic rings of the tamoxifen molecule. For example, a 4-hydroxytamoxifen derivative in which X=—OH has been developed having the structure shown below [33]:

[Formula 2]

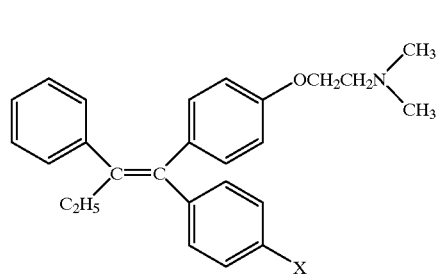

However, while the 4-hydroxytamoxifen derivative was shown to be a potent anti-estrogen in vitro, it proved to be less effective than tamoxifen in vivo, owing to rapid glucuronidation of the hydroxyl group, followed by excretion. 4-Hydroxytamoxifen is the active intracellular form of the tamoxifen molecule in vivo, due to cytoplasmic hydroxylation after tamoxifen enters the cell. However, when 4-hydroxytamoxifen is administered in vivo, its polarity reduces its ability to cross the cell membrane, thereby reducing its access to estrogen receptors located in the cytoplasm. Therefore, in vivo tests indicate 4-hydroxytamoxifen to be less active than the native tamoxifen.[23]

Other tamoxifen derivatives having a 4-position substitution of the phenyl ring, in which X is methoxy, methyl, fluoro or chloro, have also been proposed and evaluated.[15] K. E. Allen et al. (1980) conducted studies wherein the 4-methyl, 4-chloro and 4-fluoro derivatives were evaluated and found to have approximately equal activity for estrogen receptor binding affinity compared to tamoxifen in vitro. However, uterine weight tests indicated that these phenyl group derivatives had lower anti-estrogenic activity than tamoxifen, while other tests indicated that the activity of the 4-methoxy phenyl derivative was about the same as native tamoxifen.

A 4-iodo substitution of the phenyl ring as a tamoxifen derivative (formula 2: X=iodo) has recently been found to have greater potency than tamoxifen in relation to detecting estrogen receptor-positive breast cancer.[13] Other 3-iodo, 4-iodo, 3-bromo and 4-bromo phenyl ring-substituted tamoxifen derivatives have also been described.[13] For example, the McCaque et al. patent (U.S. Pat. No. 4,839,155) described the preparation of an iodo or bromo halogenated tamoxifen. However, the halogen, I or Br, was again substituted at one of the phenyl rings of the tamoxifen structure.

Derivatives of tamoxifen wherein other than the phenyl groups of the molecule are substituted have not been proposed in the art. Such a molecule would be desirable, as it would leave the major portion of the molecule unchanged and free to bind with the "target" molecule or tissue cells. Additionally, to further enhance tissue targeting specificity, a non-phenyl ring halogenated tamoxifen derivative would preferably be coupled with a "targeting" molecule, such as a microparticle.

Non-phenyl ring halogenated tamoxifen derivatives with enhanced binding affinity, greater specific radioactivity, and which can readily traverse the cell membrane have not as yet been developed in the art. The development of such derivatives would represent a tremendous improvement in the quality of imaging techniques currently available, as well as improve the accuracy of PET and SPECT scans.

Other alternative compounds proposed as possible radiopharmaceuticals useful in the imaging of tissue receptors include labeled progesterone and estrogen derivatives. For example, Pomper et al. described a ligand for the progesterone receptor.[16] The aliphatic fluorination of FENP (21-[$^{18}$F]fluoro-16-α-ethyl-19-norprogesterone) is described as demonstrating a high specific uterine target tissue uptake.[16] This ligand for the progesterone receptor was labeled with the positron-emitting radionucleotide fluorine-18 (t ½=110 min).

Estrogen-based imaging agents described in the literature include radionuclides of iodine[20], fluorine[19], and bromine[21]. By way of example, an estrogen-based imaging agent described in the literature is the 16-α-[$^{18}$F]fluoro-17-β-estradiol ligand.[17]

The preparation of 16-α-[$^{18}$F]fluoroestrogens and their selective uptake by estrogen target tissues in rats has been described by Kiesewetter et al.[19]. Significant changes in the binding of estrogen receptors in breast tumor were reported with the use of [$^{18}$F]fluoroestradiol using PET.[4] However, the radioisotope $^{18}$F has a very short half life, and therefore techniques and molecules which employ this radioisotope must be rapid, and preferably more rapid than currently employed molecular labeling techniques allow.

Unfortunately, estrogen-based imaging agents are of limited utility in patients receiving estrogen based therapies due to the competition between imaging agents and therapeutic agents for estrogen receptors. Thus, a poor correlation is likely to exist between the actual physiological response within the tumor during hormonal therapy versus the response which is shown by an estrogen-based imaging agent. For these reasons, a progestin-based imaging agent for breast tumors might be preferred over an estrogen-based agent because tumor response to hormonal therapy appears to correlate better with progesterone receptor positivity than with estrogen receptor positivity.[17] It has further been reported that estrogen receptor positive tumors in patients on hormonal therapy (e.g. tamoxifen) could not be imaged with an estrogen, as the circulating levels of tamoxifen and its metabolites are sufficiently high to fully occupy the estrogen receptor[18], making visualization quite difficult.

While the radiolabeled tamoxifen derivatives described in the literature have demonstrated some increase in estrogen receptor binding affinity, they do not demonstrate sufficient specific radioactivity due to the low tamoxifen phenolic ring incorporation of the radioactive halogen atoms. Thus, the derivatives' enhanced affinity for estrogen receptor is offset by a reduction in the radioactivity incorporated.

Moreover, the fluorine ion radioisotope, $^{18}$F, with its reportedly low effective dose equivalency and a short half-life (t ½=110 min) further exacerbates the problem of obtaining sufficiently labeled reagent, which is stable over an experimentally useful period of time.

For these reasons, any method which would utilize $^{18}$F in labeling the phenyl rings of tamoxifen molecule must be rapid (i.e. within a 2 hour reaction time) to avoid a loss in specific activity of the label.

Currently used tamoxifen derivatives, substituted at the various phenolic sites of the tamoxifen structure, can potentially block the formation of the active metabolite, 4-hydroxytamoxifen. Such a blockage may result in a decrease in receptor binding affinity of the particular tamoxifen analog since the 4-hydroxylated derivative is known to possess higher affinity. Alternatively, a competitive elimination reaction of 4-position substituted analogs may occur in the cytosol through the formation of the active metabolite, 4-hydroxytamoxifen. Such elimination processes are known to sometimes occur after drugs cross cell membranes.

Tamoxifen derivatives which could be more rapidly synthesized, with higher specific radioactivity and/or with improved receptor binding affinity or specificity, would offer a significant advance to the art, especially with regard to the in vivo diagnosis and therapy of estrogen positive tumors and the imaging of estrogen receptors in patients on a hormone-based regimen.

Numerous studies have shown that retinoic acid (RA) provides a promising new approach to the prevention and treatment of cancer. For instance, RA has been used as a clinically effective treatment for promyelocytic leukemia (PML) and juvenile myelogenous leukemia (JCML) in a majority of patients. RA is also active against papillomas, squamous cell carcinoma and other skin diseases (e.g., acne, psoriasis). It was hypothesized that these disorders may be due to the abnormal gene expression of RA receptors. Two subtypes of RA receptors, RARs and RXRs, are important in the biological actions. RA receptors may act to up-regulate gap junctional communication, stabilize normal cells by increasing the secretion of TGF-β (transforming growth factor) against subsequent transformation and thus, decrease cell proliferation.

RA is capable of controlling gene expression, yet, the use of RA in therapy has been hampered by its high toxicity and teratogenicity, which may be associated with its lipophilicity. Therefore, a more hydrophilic RA analogue needs to be developed that may be used for chemoprevention and as chemotherapeutic agents.

Endocrine therapy, one of the oldest nonsurgical methods for the treatment of breast cancer, is still considered standard for certain subsets of patients, typically, postmenopausal women whose breast tumors have higher levels of estrogen receptors. The presence of sex hormone receptors in both primary and secondary breast tumors is an important indicator both for prognosis and choice of therapy for the disease. Tamoxifen, a potent antiestrogen that binds to cytoplasmic estrogen receptors and prevents cancer cell proliferation, has been widely used in the therapy of ER(+) breast tumors. Compared with other hormonal treatments, tamoxifen has few side effects. Tamoxifen therapy results are positive in 30% of unselected patients with breast cancer. In patients with ER(+) tumors, a response rate of 50% to 60% was obtained. Patients with metastatic cancer who do respond to the treatment have a response duration of 10 to 18 months and prolonged survival.

It has been shown that the concentrations of serum selenium and Vitamins A, C, and E were increased significantly in patients treated with tamoxifen for 3–6 months. The results suggest that tamoxifen therapy exerts significant positive effects on the rate of lipid peroxidation and protective systems in postmenopausal women with breast cancer. In the cancerous stress condition, the requirement for vitamins and antioxidants increases progressively, therefore, the level of vitamins decreased in women with untreated breast cancer as opposed to normal control subjects. Thus, it would be advantageous to provide an anti-cancer therapy which prevents depletion of vitamins.

SUMMARY OF THE INVENTION

The present invention provides novel halogenated tamoxifen analogs found to have surprisingly and unexpectedly enhanced binding affinity for estrogen receptors. The particular chemistry of the claimed tamoxifen analogs and derivatives advantageously provides a rapid and simple method for preparing and labeling the tamoxifen molecule at a non-aromatic carbon of tamoxifen, particularly at the aliphatic (alkyl) chain of the native Lamoxifen structure demonstrated at Formula 1.

The claimed no-carrier added, aliphatic chain substituted and radiolabeled tamoxifen derivatives are unlike any other labeled tamoxifen derivative described in the literature, and possess an enhanced binding affinity for estrogen receptors while retaining high specific radioactivity. Due to this enhanced binding affinity for estrogen receptors, the described tamoxifen derivatives and analogs can be advantageously employed to treat, diagnose and/or monitor estrogen receptor-positive tumors (e.g., hormone dependent cancers). Additionally, the derivatives may also be advantageously used to predict the efficiency of tamoxifen-related therapy of breast tumors.

The term "aliphatic chain" substituted tamoxifen derivative as used in describing the claimed halogen substituted forms of the native tamoxifen molecule refers to chemically substituted forms of the tamoxifen molecule wherein a halogen, haloalkyl or hydroxy group is positioned at other than one of the three phenyl rings of the native tamoxifen structure, and at other than the double carbon bond of the native tamoxifen chemical structure (See Formula 1). Even more particularly, the tamoxifen derivatives of the present invention are defined as including a halogen, haloalkyl or hydroxy group at the end of the aliphatic carbon chain which is pendant to one of the carbons which comprises the double carbon-carbon bond of the native tamoxifen structure.

Any of the family of halogen atoms may be used in conjunction with the claimed invention. By way of example, the halogen atoms include fluorine, bromine, iodine, chlorine and astatine. Those particular halogens most preferred in the present invention include fluorine, bromine, iodine and chlorine.

The inventors' halo-alkyl, halogen, hydroxy and amino substituted tamoxifen derivatives include the halogen atom, hydroxy moiety, or amino group strategically placed on the aliphatic chain of the tamoxifen molecule. Thus modified, the molecule has greater estrogen receptor binding affinity than native tamoxifen. Additionally, the placement of a halogen, hydroxy or amino group at the aliphatic side chain, rather than on the aromatic portions of the tamoxifen structure, preserves the major portion of the tamoxifen molecule for binding with estrogen receptors and/or other molecules. Moreover, labeling of the tamoxifen structure at the alkyl site rather than at any of the structures phenolic rings, requires only minimal alteration of the tamoxifen structure. Limited modification of the tamoxifen structure is desirable because phenyl rings and phenoxyethylamine chains are essential for retaining the structure necessary to assure proper conformational fit with estrogen receptors and to facilitate successful entry of the molecule through the cell membrane and into the cytoplasm for in vivo use. As used in the present invention, the term "native" tamoxifen refers to that structure of tamoxifen which is unsubstituted and which corresponds to the chemical structure presented at Formula 1.

The substitution of the N,N-dimethyl group of tamoxifen with an N,N-diethyl group is demonstrated by the inventors to increase estrogen receptor binding with the halogen tamoxifen analog up to 30-fold. The binding affinity of the described halogenated tamoxifen derivatives to estrogen receptors is increased in all cases by at least 4-fold as compared to native tamoxifen.

Radiolabeling of the halogen tamoxifen derivative with [$^{18}$F], [$^{131}$I], [$^{123}$I], [$^{77}$Br] or [$^{11}$I] for SPECT, or [$^{75}$Br] for PET provides a molecule with both high specific radioactivity and high estrogen receptor binding affinity. Radiolabeled forms of the halogen chloride [Cl] may also be employed. In order to account for the short half life of the particular radioisotopes used, the Inventors have optimized the synthesis of these halogenated tamoxifen derivatives to provide relatively high specific radioactivity. These halogenated derivatives are also shown to have high binding affinity for estrogen receptors. The optimization of isotope half life, high estrogen receptor affinity and target cell specificity provides particular advantages for the in vivo imaging of estrogen receptors.

The distinguishing structural features of the claimed aliphatic chain substituted tamoxifen derivatives establish in part the superiority of the claimed analogs over the N,N-dimethyl (phenyl ring substituted) tamoxifen derivatives described by Foster et al. and others.[6] The claimed tamoxifen analogs and derivatives also feature the specific substitution of tamoxifen with a fluorine, iodine, chlorine or bromine halogen atom or lower halo-alkyl group at the aliphatic chain of the tamoxifen molecule, in contrast to the phenyl-ring substituted tamoxifen structure described in Foster et al.[6] The synthesis and chemical structure of the claimed halogenated and halo-allyl tamoxifen analogs are distinct from all derivatives discussed in the literature, including the phenolic ring-substituted tamoxifen derivative described by McCague in U.S. Pat. No. 4,839,155.

Most generally, the tamoxifen derivatives of the claimed invention comprise the following structure:

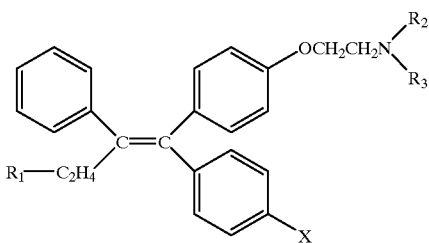

wherein $R_1$ is a halogen or lower halo-alkyl; chloromethyl, bromomethyl-hydroxy, hydroxymethyl, tosyl or tosylmethyl; $R_2$ is a lower alkyl; $R_3$ is a lower alkyl, and wherein $R_2$ is not methyl when $R_3$ is methyl. In a most preferred embodiment of the described tamoxifen derivatives, $R_2$ and $R_3$ are most particularly defmed as ethyl. In still another embodiment, $R_2$ is methyl and $R_3$ is ethyl. In particular embodiments of the invention, $R_1$ is fluoromethyl and $R_2$ and $R_3$ are ethyl. In still another embodiment, $R_1$ is iodomethyl and $R_2$ and $R_3$ are ethyl.

A lower halo-alkyl as defmed for purposes of the present invention is a carbon chain of less than 5 carbons with a halogen atom attached thereto. A lower alkyl is defined as a carbon chain of less than 5 carbon atoms such as methyl (1-C), ethyl (2-C), propyl (3-C), butyl (4-C) or pentyl (5-C). Most preferably $R_2$ is methyl or ethyl. Similarly, $R_3$ is most preferably methyl or ethyl. However, $R_2$ is not methyl when $R_3$ is methyl.

In a particularly preferred embodiment of the tamoxifen derivatives described herein, $R_1$ is a halogen further defined as bromine, chlorine, fluorine or iodine. Where $R_1$ is a lower halo-alkyl, the lower halo-alkyl by way of example is defined as bromomethyl, fluoromethyl, iodomethyl or chloromethyl. In still a further embodiment of the described tamoxifen derivative, $R_1$ is a lower hydroxy alkyl, such as, for example, hydroxymethyl.

In a second most particularly preferred embodiment, the tamoxifen derivatives included within the scope of the invention are radiolabeled, and comprise:

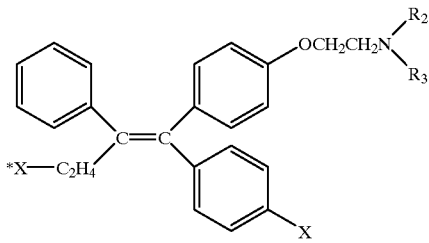

wherein *X is $^{18}F$, $^{131}I$, [$^{18}F$]fluoromethyl, [$^{131}I$]iodomethyl, chloromethyl, or bromomethyl; $R_2$ is methyl or ethyl, and wherein $R_3$ is methyl or ethyl. Most preferably, $R_2$ is not methyl when $R_3$ is methyl. In a particularly preferred embodiment of this particular tamoxifen derivative, *X is [$^{18}F$]fluoromethyl, $R_2$ is ethyl, and $R_3$ is ethyl. The three phenyl rings of the tamoxifen structure are unsubstituted phenyl rings. In still another particularly preferred embodiment, *X is [$^{131}I$]iodomethyl, $R_2$ is ethyl and $R_3$ is ethyl.

In still another most preferred embodiment of the claimed tamoxifen derivative, $R_1$ is chloromethyl or chloro, $R_2$ is ethyl and $R_3$ is ethyl. Where bromine is the halogen, $R_1$ is bromomethyl or bromo, $R_2$ is ethyl and $R_3$ is ethyl.

The invention also provides a tamoxifen derivative $^{99m}$Tc-labeled tamoxifen (TX) analogue, and the use of this and other simllar tamoxifen analogs in the development of SPECT ligands. These SPECT ligands may be used, for example, in the imaging of breast tumors, particularly estrogen receptor positive breast tumors.

The fluoromethyl tamoxifen derivatives herein disclosed demonstrate an enhanced binding affinity for estrogen receptors compared to other tamoxifen derivatives having a 30-fold (trans) and 6-fold (cis) enhanced estrogen receptor binding affinity. For iodo-methyl tamoxifen analogs, the trans isomer has a 15-fold and the cis-isomer has a 10-fold enhanced estrogen receptor binding affinity, compared to other tamoxifen derivatives described in the literature. Salituro et al. reported that the cis isomer of tamoxifen azizidine has 50-fold less affinity than the trans isomer. Placing a fluorine atom at the 4-position of phenyl ring has been demonstrated to decrease binding affinity 40-fold when compared to native tamoxifen. Pomper et al describes progesterone analogs only, which have affinity for progesterone receptors. Thus, that data is not directly compared here. (Shani et al.)[38]

The bromomethyl tamoxifen analogs provide for the trans isomer a 50-fold enhancement of estrogen receptor binding affinity, and for the cis isomer, a 38-fold enhancement of estrogen receptor binding affinity. Particular other of the tamoxifen derivatives exhibit at least a 4-fold increase in estrogen receptor binding affinity compared to native tamoxifen.

Because of the enhanced estrogen receptor binding affinity demonstrated by the described tamoxifen derivatives and analogues, Applicants provide an efficient and specific reagent which is useful in the imaging of estrogen receptors. In such an embodiment, the tamoxifen derivative includes a radiolabel "tag", most preferably an $^{18}F$, $^{131}I$, $^{123}I$ or $^{75}Br$ (for positron) and $^{77}Br$ atom (for SPECT). In a most particularly preferred embodiment of the imaging reagent, the "tag" is an $^{18}F$, $^{131}I$, or $^{77}Br$ radionucleotide located at the alkyl side chain of the halogen-substituted tamoxifen molecule.

Most preferably, the alkyl side chain (for $R_2$ and $R_3$) comprises a carbon chain of at least two carbons (ethyl). Methods of performing the described radiosynthesis of the disclosed [$^{18}F$]fluoromethyl, [$^{131}I$]iodomethyl, $^{77}Br$ bromomethyl tamoxifen derivatives are also provided herein. The radiosynthesis of $^{77}Br$-labeled tamoxifen is similar to the $^{131}I$-labeled analog. Therefore, the methods described herein for the preparation of radiolabeled fluoro and iodo tamoxifen derivatives may be utilized for the preparation of radiolabeled forms of the bromo and chloro derivatives, by using an analogous bromo- or chloro-salt as the starting reagent.

In that the halogenated derivatives of tamoxifen disclosed herein have enhanced estrogen receptor binding affinity, the presently disclosed tamoxifen derivatives provide an improved method by which estrogen receptors may be imaged through a PET or a SPECT radioimaging protocol. Most particularly, the halogen to be used in forming these estrogen binding agents is fluorine, bromine, or iodine.

Additionally, in order to even further enhance the tissue-targeting of the halogen tamoxifen derivatives to those tissues rich in estrogen receptors, the inventors propose to couple the described radiolabeled, substituted tamoxifen derivatives to microparticles. This coupling can be accomplished by reacting the tamoxifen derivative (such as the halogenated or amino tamoxifen derivatives) with a polymer in the presence of a coupling reagent (e.g., dicyclohexylcarbodiimide) (See FIG. 4). The coupling of the tamoxifen derivative with the microparticle is expected to enhance the molecule targeting to particular tissues. The "payload" (e.g., a chemotherapeutic halogenated tamoxifen derivative) can then be released from microparticles by a diffusion or erosion process and used to kill tumors.

To test this approach, estrone (estrogen agonist) was conjugated to poly(benzyl)glutamate (PBLG). After conjugation, the estrogen receptor binding was determined. The $IC_{50}$ for estrone was $5\times10^{-8}M$, whereas the conjugated analog was $5\times10^{-7}M$. The conjugation yield was 86% (determined from UV at 282 nm). PBLG polymer loaded with cisplatin (an antitumor agent) showed sustained release properties (particle size 100 $\mu M$). Similar conjugation techniques will be used to conjugate halogenated tamoxifen to PBLG.

Any substituted tamoxifen derivative, wherein the halogen substitution is located at a non-aromatic site of the tamoxifen molecule, specifically at the aliphatic side chain (i.e., the $C_2H_5$ group shown in the native tamoxifen structure), would be capable of functioning as an imaging agent with enhanced estrogen receptor binding affinity. The halogenated tamoxifen derivatives most preferred in the present invention include the bromotamoxifen analogs, such as bromomethyltamoxifen. Of the fluoromethyl derivatives, N, N-diethylfluoromethyltamoxifen is most preferred. The most preferred iodo-tamoxifen derivative of the described estrogen receptor radiopharmaceutical agents is iodomethyltamoxifen labeled with $^{131}I$. The most preferred bromotainoxifen derivatives of the present invention include the bromomethyl-tamoxifen analogs labeled with $^{77}Br$.

One object of the present invention is to provide an estrogen receptor imaging reagent which has high affinity for the estrogen receptor and high enough specific activity (>1 Ci/$\mu$mol) to be suitable for use in positron emission tomography. Another object of the invention is to provide an imaging reagent which, as a result of the foregoing characteristics, has superior target tissue selectivity in vivo. Another object of the present invention is to provide a method for monitoring the effectiveness of tamoxifen therapy in treating breast tumors.

A further object of the present invention is to achieve a substituted tamoxifen derivative which has both high estrogen receptor binding affinity and high specific radioactivity. More specifically, an object of the present invention is to provide an easy and rapid radiosynthesis of substituted tamoxifen derivative (i.e., with fluoro-, iodo-, chloro-, or bromo- or hydroxy-tamoxifen analogs) with high specific radioactivity (e.g., $^{18}F$, $^{131}I$, or $^{77}Br$) at the aliphatic chain of the tamoxifen structure.

By providing a molecular substitution (i.e., halogen, halo alkyl or hydroxy group) at the aliphatic chain of the tamoxifen molecule, the bioactivity of the claimed tamoxifen derivatives is preserved through the retention of the majority of the native structure of the molecule, leaving the majority of the molecule available for binding cell (estrogen) receptors.

An additional object of the invention is to provide a simple and inexpensive method for radiosynthesizing these derivatives. Methods for preparing the disclosed site specific halogenated tamoxifen derivatives are thus also provided. Currently available methods for directing the substitution of tamoxifen at the aliphatic chain require multiple and time consuming chemical steps. Thus, the formulation of a more efficient and rapid method for preparing halogen alkyl chain substituted tamoxifen derivatives would represent a significant and valuable advance in using particular short half life radiolabeled tamoxifen analogs as radiopharmaceuticals. For example, radionuclide $^{18}F$ analogs have an extremely short half life of only about 2 hours. Therefore, time is of the essence in processing and using $^{18}F$-labeled tamoxifen analog molecules.

An additional object of the present invention is to provide halogenated tamoxifen derivatives which have superior estrogen receptor binding affinities compared to native tamoxifen and to the tamoxifen and progestin derivatives described in the literature.

By way of example, such halogen tamoxifen derivatives of the present invention include floro-, iodo-, bromo- and chloro- tamoxifen analogs. In regard to the $IC_{50}$ values, it should be considered that different species (e.g., pig, rat, dog, rabbit) will have different $IC_{50}$ values (for the same compound). However, the Ki should remain the same. Therefore, to report data, one must include a standard sample (e.g., tamoxifen, estradiol, diethylstilbestrol) and compare the relative value to a standard sample. $IC_{50}$ values, therefore, between species cannot be readily compared. Relative binding affinities are more easily comparable. Results of the presently described halogenated alkyl analogs of tamoxifen are therefore expressed in terms of relative binding affinities.

Another object of the present invention is to provide a more stable in vivo reagent. The Inventors have discovered that one of the advantages of adding halogen atoms to the tamoxifen alkyl chain, instead of at a ring structure of the molecule, is that the molecule has a greater in vivo stability. For example, the active metabolite of tamoxifen is formed at the 4-position of the aromatic ring. If a halogen is placed on the phenyl ring, the halogen-substituted site of the molecule will hinder active metabolite formation. Also, in vivo elimination of halogen may then occur at the phenyl ring to destroy the halogen-substituted forms of tamoxifen. Thus, halogen substitution on the phenyl ring reduces the amount of active metabolite formation in vivo. Substitution of the tamoxifen molecule at the alkyl chain, provides a more stable in vivo reagent as the alkyl chain portion of the tamoxifen molecule does not block the hydroxylation reaction which results in the formation of the active metabolite of tamoxifen.

An additional object of the invention is to provide an effective anti-cancer therapeutic agent for reducing estrogen-receptor positive breast, ovarian, and uterine cancer. The described analogs may also be useful as anti-cancer agents of cancers affecting the estrogen receptor-rich tissue of the brain.

An ultimate object of the present invention is to provide a non-steroid based radiopharmaceutical agent, useful in PET, which has high specific radioactivity and high target tissue selectivity by virtue of its high affinity for the estrogen receptor. The tissue selectivity is capable of further enhancement by coupling this highly selective radiopharmaceutical with targeting agents, such as microparticles.

These objects of the present invention are served with the particular aliphatic substituted tamoxifen derivatives of the present invention. Scratchard analysis of estrogen receptor binding in pig uterus using [H-3]estrdiol gave Bmax=376 fmol/mg of protein and Kd=5 nM. The IC-50s ($\mu M$) were: TX,30, FMTX, Cis=5, trans=1; ClMTX, cis=4, trans=0.4; BrMTX, cis=0.8, trans=0.2; ImTX, cis=3, trans=2; OHMTX cis=10, trans=7. For MCF7 breast tumor cell inhibition, the IC-50 of TX was 11 $\mu M$. The relative potencies were TX=100; FMTX, cis=224, trans=93; ClMTX, cis=335, trans=146; BrMTX, cis=2355, trans=298; IMTX, cis=466, trans=175; OHTX, cis=66, trans=50. These results indicate that all of the analogs of tamoxifen described herein produce greater receptor binding affinity and have more potent tumor cell inhibition than tamoxifen, thus establishing their utility for in vivo imaging of breast tumors.

Additionally, ER binding in pig uterus using [$^3$H] estradiol, Scratchard analysis (N=9) gave Kd=5 nM and Bmax=376 fmol/mg of protein. The Ki (nM) values were: TX=15,000; fluoromethy TX (FMTX), cis=2500, trans=500; iodomethyl - TX (IMTX), cis=1500, trans=1,000. In vivo tissue uptakes in rat (% injected dose per organ, n=5) for $^{131}$I-IMTX (trans) at 3 h, 6 h, and 24 h were: uterus, 0.5±0.04, 0.14IO.16 and 0.01±0.001; liver, 5.3±0.84, 3.0±0.02, 1.7±0.21. Uterus/blood ratios were 1.6, 1.5 and 1.2. The IC50 ($\mu$M) values for MCF7 cell inhibition were TX=11, FMTX, cis=4.5, trans=1.8, IMTX, cis=2.4, trans=6.3 uterus/muscle rations were 11.0, 7.6 and 3.6.

Still another aspect of the invention provides amino tamoxifen derivatives having an amino group substitution at the alkyl, nonphenolic site of the native tamoxifen chemical structure. Preferably, none of the phenolic sites of the molecule are substituted. More specifically, the amino tamoxifen derivative of the present invention may be described as having a formula:

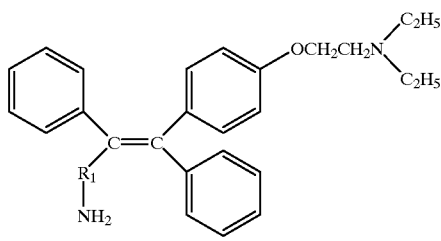

wherein $R_1$ is methyl, ethyl or propyl. Most preferably, the amino tamoxifen derivative of the present invention includes an $R_1$ that is propyl (3 carbon chain alkyl group). The present invention also provides for labeled, particularly radiolabeled forms of the amino tamoxifen derivative described herein, wherein the label or radiolabel is included at the alkyl amino substituted site of the derivative. In one preferred embodiment, the labeled amino tamoxifen derivative comprises the amino tamoxifen derivative formula defined as:

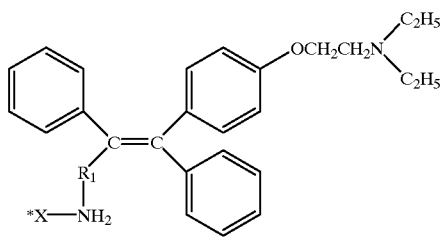

The amino tamoxifen derivatives may thus be prepared to include a detectable labeling agent at the alkyl amino group. Any labeling agent may be employed in conjunction with the presently described amino tamoxifen derivatives. By way of example, such radiolabels include $^{18}$F, $^{77}$Br, $^{75}$Br, $^{131}$I, $^{121}$I or [$^{11}$CH$_3$I]. In a most preferred embodiment of the radiolabeled amino tamoxifen derivative, $R_1$ is propyl and the labeling agent is [$^{11}$CH$_3$I].

The radiolabeled amino tamoxifen derivatives thus have the following structure, wherein the *X represents the radiolabeled site of the molecule:

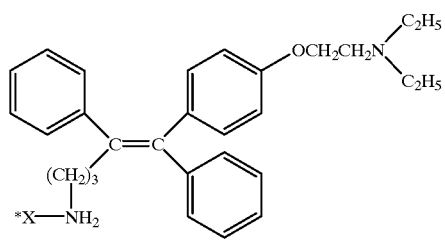

The present invention also provides methods for inhibiting estrogen-receptor positive tumors. In one preferred aspect of the method, an amino tamoxifen derivative having a formula:

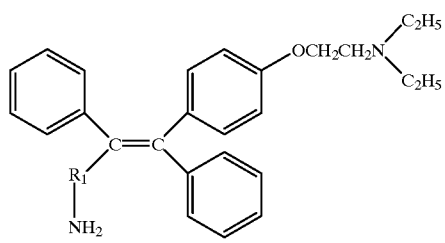

wherein [$R_1$] is methyl, ethyl, or propyl, is to be used. Most preferably, the method comprises administering the amino tamoxifen derivative to an animal or tumor. Preferably, $R_1$ of the amino tamoxifen derivative is propyl (3-carbon chain alkyl group). In an alternative embodiment, the amino tamoxifen derivative includes methyl as $R_1$.

A radiopharmaceutical agent having binding affinity for an estrogen receptor is also provided. The radiopharmaceutical agent is more particularly described as an alkyl-chain amino substituted radiolabeled tamoxifen derivative. By way of example, the radiolabel of the alkyl chain amino substituted tamoxifen derivative may comprise $^{18}$F, $^{77}$Br, $^{75}$Br, $^{131}$I, $^{121}$I or $^{11}$CH$_3$I. Most preferably, the radiolabel of the above-described alkyl chain amino substituted tamoxifen derivative is labeled at the alkyl side chain of the tamoxifen derivative at a site, *X. For example, *X may comprise $^{11}$CH$_3$I, and would have the following structure:

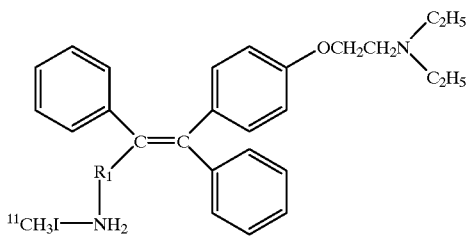

The inventors also disclose herein methods for preparing an alkyl chain amino substituted tamoxifen derivative. This method is outlined in detail in the Detailed Description of the Preferred Embodiments. Generally stated, the alkyl chain substituted amino tamoxifen derivative of the present invention is prepared by synthesizing a tosyl analog of tamoxifen as described herein; reacting the tosyl analog of tamoxifen with sodium azide; and hydrogenating the tosyl analog of tamoxifen to provide an amino tamoxifen analog. This method is shown in FIG. 20. The synthesis of various tamoxifen analogs (electronic effect) is presented in Table 1.

TABLE 1

Synthesis of Tamoxifen analogues (Electronics Effect)

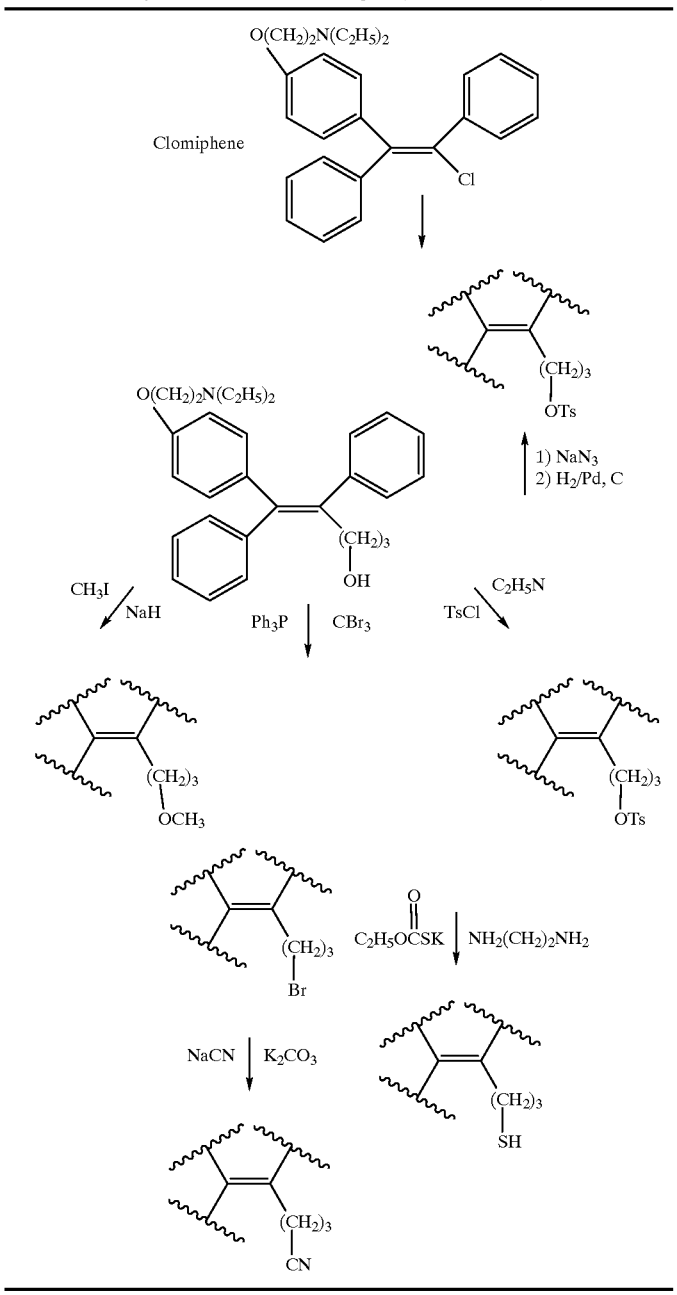

The present invention also provides for methods of imaging estrogen receptors in an estrogen receptor-rich tissue. In one embodiment, the method comprises administering a sufficient quantity of an alkyl chain amino substituted radiolabeled tamoxifen derivative to an estrogen receptor-rich tissue of a patient; positioning the patient supine in a PET device; performing an emission scan of the estrogen receptor-rich tissue and obtaining a PET image of the tissue; and evaluating the PET image for the presence or absence of focally increased uptake of the radiolabeled amino substituted tamoxifen derivative in the tissue. By way of example, the radiolabel of the alkyl chain amino substituted radiolabeled tamoxifen derivative is $^{18}F$, $^{77}Br$, $^{75}Br$, $^{131}I$, $^{121}I$ or $^{11}CH_3I$. The method may be used to image estrogen receptors in virtually any estrogen receptor-rich tissue. By way of example, such estrogen receptor-rich tissues include breast tissue or uterine tissue.

The alkyl chain amino substituted tamoxifen derivatives of the present invention may also be advantageously employed as pharmaceutical agents for the therapy of estrogen hormone dependent tumors. As such, the invention provides in still another aspect a pharmaceutical agent suitable for the therapy of an estrogen hormone dependent tumor. The pharmaceutical agent of the present invention may therefore be defined as a alkyl chain amino substituted tamoxifen derivative. The pharmaceutical agent, in a most preferred embodiment, may be defined according to the formula:

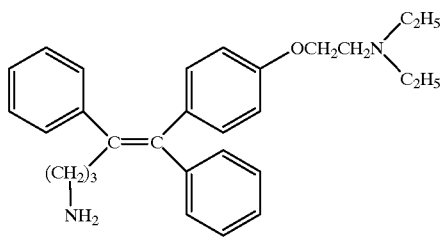

The present invention also provides for DTPA tamoxifen derivatives. These compounds have in some embodiments a structure defined according to the formula:

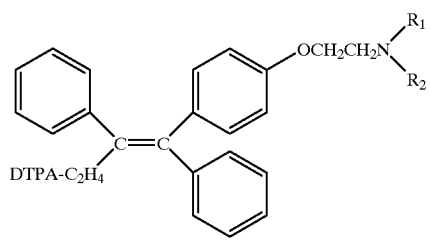

wherein, $R_1$ is methyl or ethyl and wherein, $R_2$ is methyl or ethyl. In some embodiments of the derivative, $R_1$ is not methyl when $R_2$ is methyl. In still other embodiments, both $R_1$ and $R_2$ are ethyl. In still other embodiments, the DTPA tamoxifen derivatives is further defined as an amino DTPA tamoxifen derivative.

In some aspects of the present DTPA tamoxifen derivatives, the compound includes a detectable labeling agent, such as an enzyme or radio isotope. By way of example, such PET and SPECT radio isotopes include $^{68}$Ga, $^{111}$In, $^{99m}$Tc or $^{90}$Y, $^{188}$Re, when DTPA-tamoxifen is chelated with paramagnetic atoms $^{56}$Fe, $^{55}$Mn or $^{157}$Gd, it can be applied to MRI studies.

The present inventors have found that the DTPA tamoxifen derivatives of the present invention are relatively hydrophilic compared to native tamoxifen. Hence, the DTPA tamoxifen preparations of the present invention are particularly convenient for packaging in commercial products, such as in diagnostic imaging kits and the like.

The present invention also in still another aspect provides for a method of inhibiting an estrogen receptor positive tumor. For example, the method may comprise administering to a patient a tamoxifen derivative having a formula:

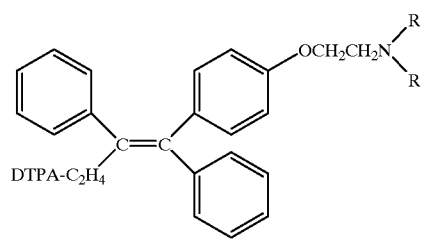

wherein, R is a lower alkyl of from 1 to 5 carbons, such as methyl or ethyl.

Another aspect of the invention provides for a method of preparing a DTPA tamoxifen derivative. In one embodiment, the method comprises dissolving a quantity of clomiphene in a sufficient volume of tetrahydrofurin to form a reaction mixture; adding bromomethyldioxsolane to the reaction mixture to form a second reaction mixture; diluting the second reaction mixture with cholorform and washing with water to provide a washed mixture; drying the washed mixture over sodium sulfate, filtering and evaporating the mixture to driedness to provide a dry product; purifying the dry product to obtain aldotamoxifen; mixing the aldotamoxifen with aminoethylanalide-DTPA to provide a third mixture; and treating the third mixture with $NaCnBh_3$ and evaporating the mixture to provide DTPA-tamoxifen.

The invention also provides for a method of preparing a radiolabeled DTPA-tainoxifen. In one embodiment, the method comprises the afore listed steps, followed by dissolving the DTPA-tamoxifen in ethanol-water to provide a solution; adding radioisotope to the solution; adding sodium acetate and sodium citrate to the solution and formulating the solution in ethanol/saline to obtain a radiolabeled DTPA tamoxifen. In particular embodiments, the isotope is $^{111}InCl^3$, $^{111}InCl^{333}$ or $^{99m}Tc$.

In still other embodiments, an aminotamoxifen analog which is a compound of:

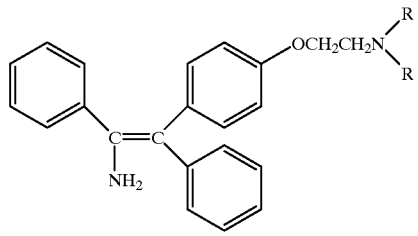

wherein, $R_1$ is methyl or methyl and wherein, $R_2$ is methyl or ethyl. This amino tamoxifen analog may further comprise a radiolabel or other detectable labeling agent most preferably, the labeling agent is to be placed at the site of the $NH_2$ molecule. The molecule may further comprise an aldehyde (X) group pendant the amino group. By way of example, said aldehyde may be DTPA. In one embodiment, the labeling agent is $^{111}$In.

In still another aspect, the invention provides for a method of inhibiting an estrogen receptor positive tumor. This method in one embodiment comprises administering an amino tamoxifen analog having the structure:

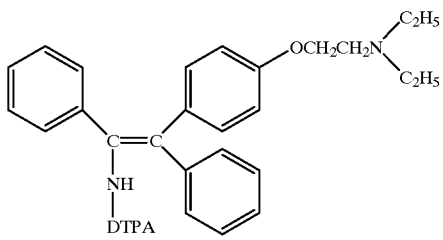

similarly, the invention provides for a radiopharmaceutical agent, this particular agent having binding affinity for an estrogen receptor. This agent is further defined as comprising an alkyl chain radio labeled amino DTPA tamoxifen analog.

The inventors also disclose a method for imaging estrogen receptors in an estrogen receptor-rich tissue. This method in one embodiment comprises administering a sufficient quantity of an amino tamoxifen DTPA analog to an estrogen receptor rich tissue; positioning the patient supinena PET devised; performing an emission scan of the estrogen receptor ridge tissue, and obtaining a PET image of the tissue; and evaluating the PET image for the presence or absence of focally increased intake of the radiolabel and the tissue.

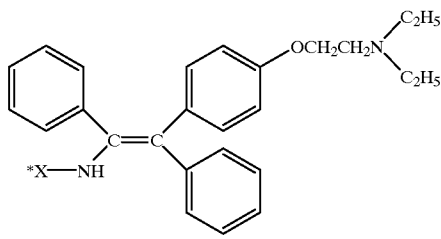

wherein, X is an aldehyde. By way of example X may be DTPA.

It is anticipated that the particular estrogen receptor rich tissues with which the described method may be most particularly useful includes breast or uterine tissue. However, other estrogen rich or even other estrogen possessing tissues may also be processed according to the claimed method in order to detect presence of this particular type of receptor or estrogen responsive tissue.

In still another embodiment, the invention provides a pharmaceutical agent for the therapy of an estrogen hormone dependent tumor. This pharmaceutical agent in some embodiments comprises an amino tamoxifen DTPA analog. This analog in particular embodiments has a structure:

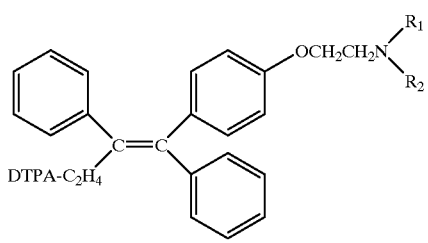

wherein, $R_1$ is methyl or ethyl and wherein $R_2$ is methyl or ethyl. They need not necessarily include a radio isotope, making them particularly patient compatible, the DTPA analog also, as previously described as being hydrophilic. These compounds therefore may be relatively quickly cleared by the liver.

The invention also provides compositions comprising a DTPA-tamoxifen derivative and a vitamin, such as Vitamin A. These cocktails are also useful in the treatment of cancer. These preparations are also useful in a method for diagnosing and monitoring the treatment of breast cancer, comprising administering to a patient suspected of having breast cancer a composition of an amino tamoxifen derivative and Vitamin A. In some embodiments, this amino tamoxifen derivative is DTPA-tamoxifen.

The following numerical designation of particular tamoxifen compounds is employed throughout the Specification:

| | |
|---|---|
| Compound I | Tamoxifen |
| Compound II | N,N-diethyl-hydroxytamoxifen |
| Compound III | N,N-diethyl-hydroxymethyltamoxifen |
| Compound IV | N,N-diethyl-fluorotamoxifen |
| Compound V | Hydroxytamoxifen |
| Compound VI | N,N-diethyl-fluoromethyltamoxifen |
| Compound VII | Fluorotamoxifen |
| Compound VIII | N,N-diethyl-O-tosyltamoxifen |

-continued

| | |
|---|---|
| Compound IX | N,N-dimethyl-O-tosylmethyltamoxifen |
| Compound X | N,N-diethyl-iodomethyltamoxifen |
| Compound XI | N,N-diethyl-bromomethyltamoxifen |
| Compound XII | N,N-diethyl-chloromethyltamoxifen |

The following abbreviations are included throughout the body of the Specification:

| | |
|---|---|
| BrTX = | bromotamoxifen |
| BrMTX = | bromomethyltamoxifen |
| ClTX = | chlorotamoxifen |
| ClMTX = | chloromethyltamoxifen |
| ITX = | iodotamoxifen |
| IMTX = | iodomethyltamoxifen |
| FTX = | fluorotamoxifen (VII) |
| FMTX = | fluoromethyltamoxifen |
| TX = | tamoxifen (I) |
| $B_{max}$ = | the total number of binding sites determined from Scratchard analysis. |
| $E_2$ = | estradiol |
| $IC_{50}$ = | the concentration of test compounds that decreases 50% of specific radioligand binding in receptor assay or 50% of cell viability in MCF-7 cell growth assay. |
| PET = | positron emission topography |
| $K_d$ = | dissociation constant determined from a saturation estrogen receptor assay and a Scatchard analysis. |
| ER = | estrogen receptor |
| FMTX = | Fluoromethyltamoxifen |
| $K_i$ = | inhibition constant determined using the equation $K_i = \dfrac{IC_{50}}{1 + [^3H]\,estradiol/Kd}$ |
| RBA = | relative binding affinity, the relative concentration of estradiol and tamoxifen or its derivatives required to achieve 50% inhibition of $[^3H]$-$E_2$ binding. |
| RP = | relative potency |
| TX = | Tamoxifen |
| $NH_2$-TX = | Amino tamoxifen |

BRIEF DESCRIPTION OF THE DRAWINGS

FIG. 6 (cis) fluorotamoxifen Scatchard plot analysis.

FIG. 23 $^1$H-NMR of Aldotamoxifer.

FIG. 35B=2 hours;
FIG. 35C=4 hours.

FIG. 36A=24 hours;
FIG. 37A–48 hours.

FIG. 37 DTPA—tamoxifen conjugate.

FIG. 38 Female nude mice were injected with 2×10$^6$ MCF-7 breast cancer cells, plus a 60-day release 17-β estradiol pellet implanted s.c. After 20 days, the mice were treated daily with s.c. injections of 50 μg tamoxifen in 0.1 ml peanut oil, or oil alone. The estradiol pellet was removed from one group of mice, and these animals received no further treatment. Tumor volumes were measured twice weekly. Oil=●; tamoxifen=▽; estrogen withdrawn=▼.

FIG. 39 Female nude mice were injected with 2×10$^6$ MCF-7 breast cancer cells, plus a 60 day release 17-β estradiol pellet implanted s.c. After 20 days, the mice were treated daily with s.c. injections of 50 μg tamoxifen or iodotamoxifen in 0.1 ml peanut oil, or oil alone. The volumes were measured twice weekly. Oil=●; tamoxifen= ▽; estrogen withdrawn=▼.

FIG. 41 Synthesis of DTPA-vitamin A conjugate.

FIGS. 42A, 42B, and 42C Shows biodistribution of $^{111}$In-DTPA-tamoxifen in breast tumor-bearing rats (n+3/time interval, 10 μCi/rat, i.v.). Control group were administered with $^{111}$In-DTPA alone.

FIGS. 43A, 43B, and 43C Demonstrates the biodistribution of $^{111}$In-DTPA-vitamin A in breast tumor-bearing rats (n+3/time interval, 10 μCi/rat, i.v.). Control groups were administered with $^{111}$In-DTPA alone.

FIG. 48 Proposed synthetic scheme of $^{99m}$Tc-tamoxifen.

DETAILED DESCRIPTION OF THE PREFERRED EMBODIMENTS

Figure 1:
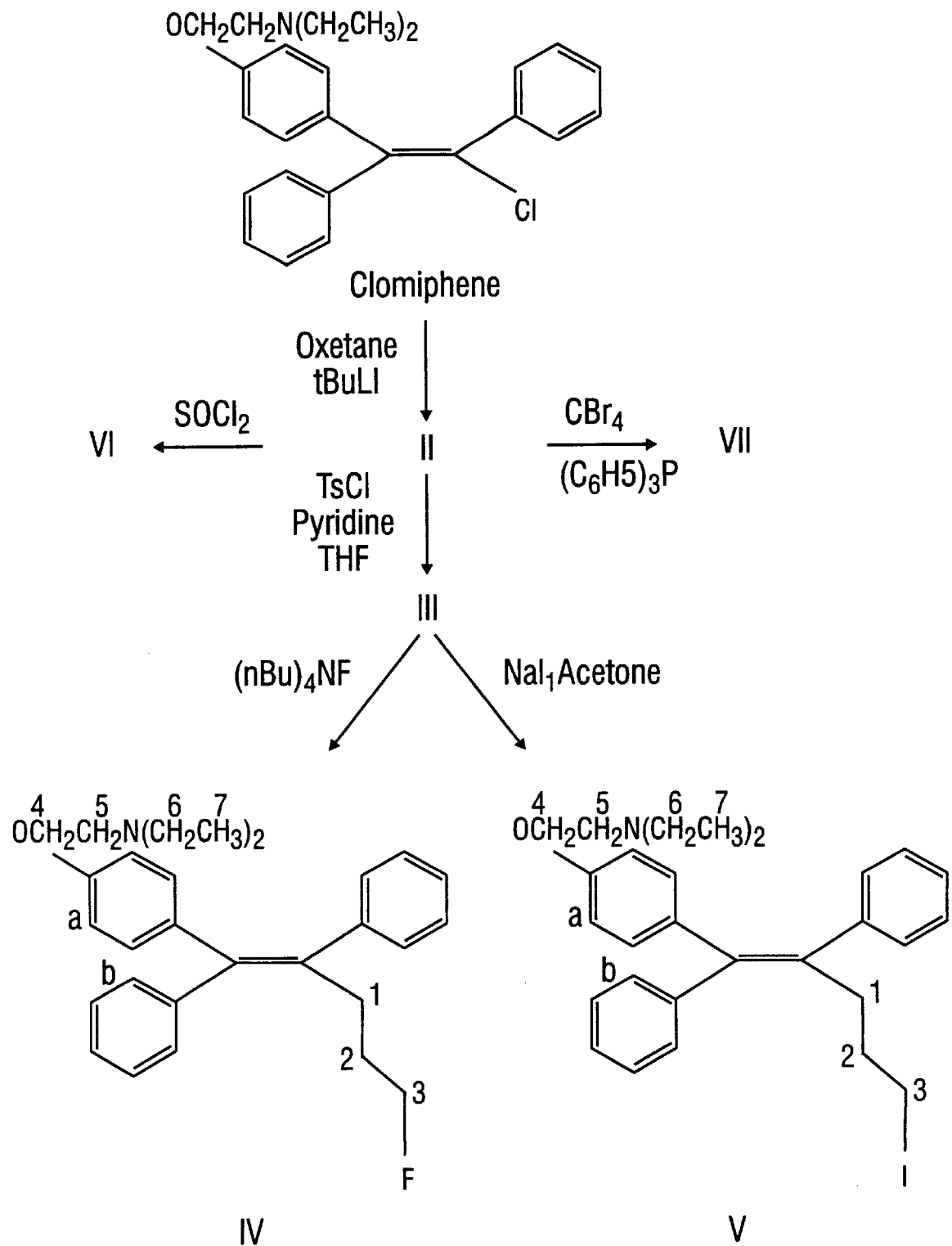
FIG. 1 Synthesis of Tamoxifen Derivatives.

The present invention discloses aliphatic chain-substituted tamoxifen derivatives having markedly enhanced estrogen receptor binding affinity compared to native forms of tamoxifen. The tamoxifen derivatives may include a halogen, a hydroxy or a lower haloalkyl moiety. Any of the halogen molecules Br, Cl, I, or F may be employed in the described site-specific halo and haloalkyl tamoxifen derivatives. Particularly preferred halotamoxifen derivatives of the present invention include fluorotamoxifen (FTX), iodotamoxifen (ITX), bromotamoxifen (BrTX), chlorotamoxifen (ClTX), and iodomethyltaxoxifen (IMTX). By way of example, a lower haloalkyltamoxifen derivative of the invention particularly includes chloromethyl tamoxifen (ClMTX).

The present invention also includes radiolabeled forms of tamoxifen. The radiolabeled forms of the substituted tamoxifen derivatives provide reagents having high specific activity. These radiolabeled tamoxifen derivatives are demonstrated to be particularly useful in estrogen receptor mapping in estrogen rich tissues, such as the uterus and breast. By way of example, the inventors provide PET imaging of estrogen-rich tissues, such as the uterus and mammary tumors, with [$^{18}$F] FTX.

Unlabeled forms of the described fluorotamoxifen derivatives were prepared from hydroxytamoxifen via diethylaminosulfar trifluoride reaction at a 47% product yield. The binding affinity of these particularly synthesized fluorotamoxifen derivatives to cytosol estrogen receptors of pig uteri in vitro was higher ($K_i$ is 500 nM; trans-compound VI) than the binding affinity observed between estrogen receptors and native tamoxifen ($K_i$ is 15,000 nM).

Unlabeled forms of iodomethyltamoxifen were prepared from tosyl analogs of tamoxifen by reacting with sodium iodide. The binding affinity of iodotamoxifen was 10–15 fold higher than tamoxifen. The unlabeled forms of chloromethyltamoxifen or bromomethyltamoxifen were prepared by treatment of a tamoxifen hydroxy precursor with $SOCl_2$ or $CBr_4$, respectively, to provide chloromethyltamoxifen and bromomethyltamoxifen in 87% and 50% yields, respectively.

Radiosynthesis with fluorine-18 was performed on tosyl tamoxifen analogs to produce radiolabeled fluorotamoxifen molecules having the described high specific activity (2–4 Ci/μmol) and a radiochemical yield of 60%. Radiochemical purity was >99%. Radiosynthesis of $^{131}$I-labeled analogs (Compound X) of tamoxifen was performed by reacting tosyl analogs of tamoxifen with NaI. The radiochemical yield was 60%.

The fluoromethyl tamoxifen, chloromethyl tamoxifen, bromomethyl tamoxifen and iodomethyltamoxifen analogs were found to bind to cytosol estrogen receptors of pig uteri and ovaries. IC-50's (μm) for F, Cl, Br, I, and native tamoxifen (TX) were found to be 1, 0.4, 0.2, 2 and 30. These results demonstrate that these halogenated derivatives are effective competitive ligands of [H-3]estradiol (5 nM).

Clomiphene, estradiol, and tamoxifen were obtained from Sigma Chemical Company (St. Louis, Miss.). Flash chromatography according to the procedure of Still et al.[7] was used. Silica gel Sep-Paks from Waters Associates (Milford, Mass.) were used for purifications. Thin-layer chromatographic (TLC) analysis was performed on Whatman K6F silica gel-packed plates (250 μm) (Anspec, Miss.). [$^3$H] estradiol (specific activity 160 Ci/mmol) for receptor binding was purchased from Amersham (Arlington Heights, Ill.). The no-carrier-added Na$^{131}$I was purchased from Syncore. High pressure liquid chromatography (HPLC) was carried out on a LDC system, consisting of two LDC ConstaMetric Pumps, a Rheodyne injector and a Spectra Physics model SP8450 variable UV/Vis detector.

Melting points were determined on a Meltemp melting point apparatus and are uncorrected. $^1$HNMR spectra were obtained from a GE 300 MHz instrument, and mass spectral data were obtained by direct probe analysis (Finnigan MAT INCOS-50) at The University of Texas Health Science Center, Houston, Tex. Elemental analyses were performed by Galbraith Laboratories, Inc., Knoxville, Tenn.

Improved and more efficient methods for the synthesis of all of the described halogenated tamoxifen analogs, including N,N-diethylfluorotamoxifen, fluoromethyl-N,N-diethyltamoxifen, N,N-diethylbromomethyltamoxifen, N,N-diethylchloromethyltamoxifen and iodomethyl-N,N-diethyltamoxifen are also disclosed as part of the invention. For example, the synthesis of fluoromethyltamoxifen and iodotamoxifen (lower alkyl halotamoxifen derivatives) has been simplified from an at least ten (10) step procedure to a more rapid and simple three-step procedure (FIG. 1). The N,N-diethylfluoro (Compound IV) and the N,N-diethylfluoromethyl (Compound VI) and N,N-diethyliodomethyl (Compound X) analogs of tamoxifen were prepared for preliminary evaluation according to these improved protocols. N,N-Diethylfluoro (IV), N,N-diethylfluoromethyl (VI) and N,N-diethyliodomethyl (X) analogues of tamoxifen were prepared from the corresponding hydroxy analogues of tamoxifen via tosyl analogues by displacement with either sodium fluoride or sodium iodide. N,N-diethyl-bromomethyltamoxifen (XI) and N,N diethylchloromethyltamoxifen (XII) analogs of tamoxifen were prepared from the corresponding hydroxy precursors of tamoxifen with $CBr_4$ or $SOCl_2$, respectively. Mixtures of the cis- and trans-isomers of the respective alkyl-chain substituted tamoxifen derivatives were obtained from this synthesis.

The cis- and trans- isomer products of each of the reactions described above were separated by passing the reaction mixture through a silica gel-packed column and eluting with ether/petroleum ether/ triethylamine (1:1:0.1). The $^1$HNMR chemical shift signals for cis- and trans- isomers were assigned based on published information.[8,11]

It was ascertained that the tosyl group on N,N-diethyl-O-tosyltamoxifen could be displaced by nucleophilic fluoride substitution reaction with a milder condition (e.g. kriptofix-222 and KF). Using this procedure, the fluoro-analogue of tamoxifen, compound IV, was prepared in 40% yield from the corresponding tosyl derivative of hydroxytamoxifen. However, elimination occurred to form the butadiene by-product in the presence of the stronger base (e.g. tetrabutylammoniumhydroxide). The formation of the butadiene by-product is due to an elimination reaction on the tosyl analogue.

Synthesis of Aliphatic Halotamoxifen Derivatives

| Compound | R |
| --- | --- |
| VI | F |
| X | I |

Increasing the side chain by one carbon results in the synthesis of Cis-N,N-diethylfluoromethyltamoxifen (VI), which is more stable toward tosyl elimination. The yield for compound VI was 60%. Compound VI showed a 6-fold (cis) and 30-fold (trans) higher affinity for the estradiol receptor binding site than native tamoxifen. The yield for Compound X was 50% (trans) and 70% (cis). Compound X showed a 10-fold (cis) and 15-fold (trans) higher ER affinity than tamoxifen. Receptor binding affinity of fluorotamoxifen, with a fluorine atom placed on the phenyl ring of tamoxifen, and of iodotamoxifen, with an iodine atom placed on the phenyl ring of tamoxifen, has been reported.[22,23] However, that significant difference in the uterus uptake between blocked and unblocked groups, suggesting uterus uptake was mediated through an estrogen-receptor process. Although liver

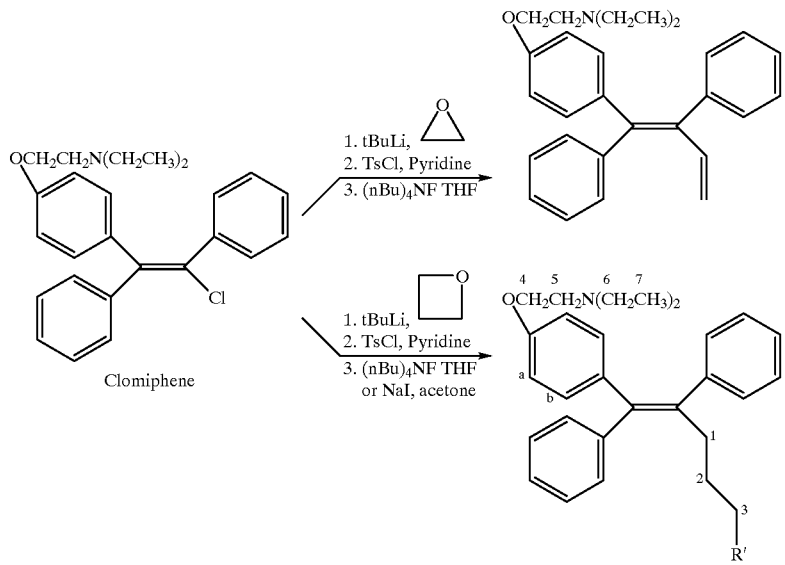

reaction for fluorotamoxifen preparation takes longer and yields lower specific radioactivity for $^{18}$F-labeled tamoxifen, which is not practical for estrogen-receptor studies using PET.

The iodine atom placed on a phenyl ring at the 2-position next to the phenoxy ring gave poor estrogen receptor binding. The iodine atom placed on the 4-position of the aromatic ring gave good receptor binding[13], yet it may be unstable in vivo due to an elimination reaction, resulting in formation of the active hydroxy metabolite. Also, the iodine atom is quite bulky, and may change the planar conformation (e.g., phenyl ring), thus impairing the binding to estrogen receptors, thereby decreasing binding affinity.

The present invention, in particular general aspects, provides hydrophilic labeling analogues of tamoxifen. One such example is DTPA-TX and chelation of DTPA with different inorganic metal produces DTPA chelates that are metabolically stable, can be used to measure renal flow (e.g., $^{99m}$Tc-DTPA, $^{111}$In-DTPA), and can be used to enhance magnetic resonance imaging (MRI) contrast (e.g., Gd-DTPA, Mn-DTPA, Fe-DTPA). Other applications of DTPA involve uses as a conjugate with antibodies and peptides. Synthesis of aldehyde tamoxifen analogues, such as DTPA-TX, whose aldehyde group can be easily reacted with DTPA-P-(aminoethyl)anilide to form an imine bond, are herein disclosed. The imine bond can be further reduced to a C—N bond, which should be stable against enzyme cleavage. This constitutes a new approach to formulating hydrophilic tamoxifen analogues that can produce a labeling yield of 100%.

To study the biodistribution of DTPA-TX, a breast-tumor-bearing rat model and a tumor cell line was used, the cell line originally induced by treatment with dimethylbenz[a] anthracene, that has a reportedly high level of ERs. Our in vitro estrogen receptor assay of breast tumors showed a tumor ER level of 7.5 fmol/mg and a receptor binding affinity for DTPA-TX similar to that of tamoxifen. The tumor-to-tissue and uterus-to-tissue ratios of $^{111}$In-DTPA-TX conjugate increased as a function of time. There was a uptake increased, it was still 10- to 15-fold less than that of fluorotamoxifen and iodotamoxifen at 2 h postinjection. Labeled DTPA-TX cleared quickly from blood, and clearance remained steady throughout time studies, indicating that the activity was localized in and specifically bound by the target tissue.

In addition, gamma scintigraphy of breast-tumor-bearing rats demonstrated that tumors could be well visualized at 30 min and clearly differentiated from bladder and liver by 48 h. The present autoradiographic findings provided similar results.

For accurately measuring breast tumor response to tamoxifen therapy, labeled hydrophilic tamoxifen is preferable to unlabeled tamoxifen because the water-soluble analogue has less liver and lung uptake, faster blood clearance, and a higher tumor-to-tissue ratio. Furthermore, assessing ER+ breast tumors or other ER+ lesions with labeled DTPA-TX prior to chemotherapy is a rational means of selecting patients for treatment with either tamoxifen or tamoxifen analogues. Such selection would also permit more accurate evaluation of antiestrogens, since their use is limited to patients with ER+ lesions. Finally, DTPA-TX and other new ligands can be chelated with unlabeled gadolinium, iron, or manganese for potential application as enhancers of MRI of breast tumors. Consequently, the use of radiolabeled DTPA-TX analogues to diagnose breast cancer may improve the response of breast tumors to tamoxifen therapy.

As used in the present invention, the term "lower alkyl" refers to a carbon chain of less than 5 carbon atoms in length. Most preferably the lower alkyl comprises 1 carbon (methyl) or 2 carbons (ethyl).

The following examples are presented only to describe preferred embodiments and utilities of the present invention, and to satisfy best mode requirements. The examples are not meant to limit the scope of the present invention unless specifically indicated otherwise in the claims appended hereto.

EXAMPLE 1

SYNTHESIS OF TRANS-FLUOROTAMOXIHEN (COMPOUND VII)

Hydroxytamoxifen (trans) (V) (8) (330 mg, 0.85 mmol) was dissolved in methylene chloride (20 ml), cooled to −40° C. and then treated with triethylamine (200 μl) added. Diethylaminosulfur trifluoride (250 μl, 1.89 mmol) was added and the reaction mixture was stirred for 1 hour at −40° C. according to our previous published method.[9] The reaction mixture was then washed with water and the methylene chloride layer evaporated to dryness. The reaction mixture was chromatographed on a silica gel column using 1:1:0.1 hexane/ethylacetate/triethylamine as eluant to yield 145 mg (43.7%) of VII:$R_{535}$ 0.40 (1:1:0.1 ether/petroleum ether/ triethylamine); $^1$HNMR (CDCl$_3$) δ2.29 (S, 6, NMe$_2$) 2.66 (t, J=5.6 Hz, 2, OCH$_2$CH$_2$N), 2.87 (dt, J=21.2 Hz, 6.3 Hz, 2, CH$_2$CH$_2$F), 3.93 (t, J=5.5 Hz, 2, OCH$_2$CH$_2$N), 4.34 (dt, J=47.2 Hz, 6.3 Hz, 2, CH$_2$F), 6.56 (d, J=8.5 Hz, 2, ArH 3,5 to OCH$_2$), 6.77 (d, J=8.3 Hz, 2, ArH 2,6 to OCH$_2$), 7.12–7.35 (m, 10, ArH); m/z 389 (12, M$^+$), 342 (30, $^+$CH$_2$-CH$_2$-F).

EXAMPLE 2

SYNTHESIS OF N,N-DIETHYLHYDROXYTAMOXIFEN (COMPOUND II)

Clomiphene (6.06 g, 14.9 mmol) was dissolved in tetrahydrofuran (100 ml) and cooled to −40° C. t-Butyl lithium (1 M in pentane, 24 mmol) was added slowly. After 5 minutes, ethylene oxide (14.6 ml, 290 mmol) was added, and the reaction mixture was stirred for 6 hours, poured into water and extracted with ether. The ether layer was evaporated and chromatographed on a silica gel column using 1:1:0.1 ether/petroleum ether/triethylamine as eluant to yield trans product (1.96 g, 27.1%, oil): and cis product (1.56 g, 21.5%, oil): Assignment of $^1$HNMR for aliphatic protons are presented in Table 2.

EXAMPLE 3

SYNTHESIS OF N,N-DIETHYL-O-TOSYLTAMOXIFEN (COMPOUND VIII)

Cis- or trans- N,N-diethylhydroxytamoxifen (II) (100 mg, 0.27 mmol) was dissolved in methylene chloride (2 ml) and cooled to 0° C. Pyridine (150 μl) and tosyl chloride (55 mg, 0.27 mmol) were added. After 2 hours, the reaction mixture was diluted with methylene chloride and washed with water. The methylene chloride layer was evaporated and chromatographed on a $^{18}$C column using 85:15:1 acetonitrile/water/triethylamine as eluant to yield cis (51 mg, 34%, oil) or trans tosyl analog (30 mg, 20%, oil): m/z 569(60, M$^+$), 397(20, $^+$OSO$_2$PhCH$_3$). Values for aliphatic protons are presented in Table 2.

EXAMPLE 4

SYNTHESIS OF N,N-DIETHYLFLUOROTAMOXIFEN (COMPOUND IV)

The present example is provided to demonstrate two methods by which compound IV may be prepared.
Method 1

Cis or trans N,N-diethylhyroxytamoxifen (II) (400 mg, 0.96 mmol) was dissolved in tetrahydrofuran (25 ml), and the solution was cooled to −40° C. A solution of triethylamine (480 μl) was added. Diethylaminosulfur trifluoride (1280 μl, 2.11 mmol) was added and the reaction mixture was stirred for three hours at −40° C. The crude material was poured into water and then extracted with ether. The ether layer was dried over anhydrous magnesium sulfate, filtered and evaporated to dryness. The mother liquor was chromatographed on a silica gel packed (3×60 cm, ACE Gloss) column using 1:1:0.1 ether/petroleum ether/triethylamine to yield purified 60 mg (15%) of trans IV (oil): Rf 0.70, and 80 mg (20%) of cis IV (oil), Rf 0.60 (1:1:0.1 ether/petroleum ether/triethylamine); trans $^1$HNMR (CDCl$_3$ δ 1.02(t, J=7.3 Hz, 6, (CH$_3$CH$_2$N), 2.57 (q, J=7.1 Hz, 4, CH$_3$CH$_2$N), 2.78(t,J=6.3 Hz, 2, OCH$_2$CH$_2$N), 2.91 (dt, J=21.5 Hz, 6.3 H, 2, CH$_2$CH$_2$F), 3.90 (t, J=6.2 Hz, 2, OCH$_2$CH$_2$N), 4.33 (dt, J=47.4 Hz, 6.3 Hz, 2, CH$_2$CH$_2$F), 6.56 (d, J=8.5 Hz, 2, ArH 3,5 to OCH$_2$), 6.75 (d, J=8.7 Hz, 2, ArH 2,6 to OCH$_2$), 7.12–7.37 (m, 10, ArH); m/z 417(50,M+)Hz. Anal. (C$_{28}$H$_{32}$NOF·⅓ H$_2$O) C, H, N. Calc., C:79.40.H:7.70, N:3, 31; Found, C:79.71, H:7.61, N:3.36.cis $^1$HNMR (CDCl$_3$) δ1.08 (t, J=7.1 Hz, 6, CH$_3$CH$_2$N), 2.64 (q, J=7.3 Hz, 4, CH$_3$CH$_2$N), 2.89–2.96 (m, 4, OCH$_2$CH$_2$N and CH$_2$CH$_2$F), 4.06 (t, J=6.4 Hz, 2 OCH$_2$CH$_2$F), 4.35(dt, J=47.1 Hz, 6.4 Hz, 2, CH$_2$CH$_2$F), 6.89–7.26 (m, 14, ArH); m/z 417 (70, M+), 402 (30). m.p. 55–57° C. Anal. (C$_{28}$H$_{32}$NOF.0.5 H$_2$O) C,H,M, calc., C:78.84, H:7.80, N:3.28; Found, C:78.71, H:7.48, N:3.20
Method 2

N,N-Diethyl tosyl analogue of tamoxifen (VIII) (40 mg, 0.07 mmol) was dissolved in tetrahydrofuran (200 μl) and then treated with tetrabutylammonium fluoride (170 μl, 1M in tetrahydrofuran). Fifteen minutes after adding TBAF, two spots were visualized by silica gel TLC (4:1 chloroform/methanol). Both products were isolated from a silica gel Sep-Pak by elution with ether/petroleum ether/triethylamine (1:1:0.1). One product isolated was the trans isomer of compound (IV) (11 mg, 40%) and the other was a butadiene derivative (30%, oil). Butadiene derivative $^1$HNMR (CDCl$_3$) δ1.08 (t, J=7.0 Hz, 6, CH$_3$CH$_2$N), 2.65 (q, J=7.0 Hz, 4, CH$_3$CH$_2$N), 2.90 (t, J=6.0 Hz, 2, OCH$_2$CH$_2$N), 4.08 (t, J=6.0 Hz, 2, OCH$_2$CH$_2$N), 4.94 (d, J=17.2 Hz, 1m CH═CH$_2$), 5.17 (d, J=10.9 Hz, 1, CH═CH$_2$), 6.78–7.26 (m, 9, ArH and CH═CH$_2$). m/z 397 (60, M$^+$). Anal. (C$_{28}$H$_{31}$NO·1.5 H$_2$O) C,H,N. Calc., C:79.21, H: 8.06: N:3.30; Found, C:79.76, H:7.56, N:3.09.

1,5H$_2$O indicates that the sample is either not dry enough or hydroscopic.

EXAMPLE 5

SYNTHESIS OF N,N-DEETHYLHYDROXYMETHYLTAMOXIFEN (COMPOUND III)

Clomiphene (3.8 g, 9.3 mmol) was dissolved in tetrahydrofuran (50 ml), cooled to −40° C. and then treated with t-butyl lithium (1 M in pentane, 20 mmol). After 10 minutes, trimethylene oxide (6 ml, 93 mmol) was added, the mixture stirred for 16 hours at room temperature, and then poured into water. The product was extracted with ether and chromatographed on a silica gel column using 1:1:0.1 ether/petroleum ether/ triethylamine as eluant to yield purified trans-product (1 g, 25%), m.p. 93–95° C. and cis product (N,N-diethylhydroxymethyl tamoxifen) (1.0 g, 25%), m.p. 85–87° C. Anal. (C$_{29}$H$_{35}$ NO$_2$) C,H,N: Calc., C:81.08, H:8.21, N:3.26; Found, C:80.56, H:7.94, N:3.32. Values for aliphatic protons are presented in Table 2.

EXAMPLE 6

SYNTHESIS OF CIS-N,N-DIETHYL-O-TOSYLMETHYLTAMOXIFEN (COMPOUND IX)

Cis-N,N-diethylhydroxymethyltamoxifen (500 mg, 1.17 mmol) (III) was dissolved in methylene chloride (20 ml), and the solution cooled to 0° C. Pyridine (0.66 ml) and tosyl chloride (266 mg, 1.40 mmol) were added. After 4 hours, the reaction mixture was diluted with additional methylene chloride (20 ml) and washed with water, dried over magnesium sulfate, filtered, and evaporated to yield 476 mg. The crude mixture was chromatographed on a $^{18}$C reverse phase column using 85:15:1 acetonitrile/water/triethylamine as eluant to yield the purified cis tosyl analogue of IX (200 mg, 29%, oil) $R_f$0.35 (silica gel plates, ether/petroleum ether/triethylamine 1:1:0.1), m/z 583(10, M$^+$). Values for aliphatic protons are presented in Table 2.

EXAMPLE 7

SYNTHESIS OF N,N-DIETHYLFLUOROMETHYLTAMOXIFEN (COMPOUND VI)

The cis- or trans-tosyl analogue of IX (117 mg, 0.2 mmol) was dissolved in tetrahydrofuran (400 μl) according to the inventors' reported procedure.[9] Tetrabutylammonium fluoride (485 μl, 1 M in tetrahydrofuran) was added, and the reaction was warmed to 80° C. After 30 minutes, the reaction was completed. The mixture was then hydrolyzed with 6N HCl 6.2 ml for 10 min. The product was chromatographed on a silica gel column, which was eluted with 1:1:0.1 ether/petroleum ether/triethylamine to yield 52 mg (60%, oil) of purified cis fluoro product (VI) or 40 mg (46% oil) of trans product $R_f$: 0.80 (silica gel plates, ether/petroleum ether/triethylamine 1:1:01), m/z 431(40, M$^+$). Anal. ($C_{29}H_{34}NOF$) C,H,N: Calc., C:80.71, H:7.94, N:3.25; Found, C:80.39, H:8.02, N:3.13 (cis) or C:79.58, H:8.01, N:3.20; $^1$HNMR AND $^{13}$C-NMR data are shown in Table 3.

EXAMPLE 8

PREPARATION OF N,N-DIETHYLEIODOMETHYLTAMOXIFEN (COMPOUND X)

Tosyl analog of tamoxifen (117 mg. 0.2 mmol) was dissolved in acetone (15 ml). Sodium iodide (150 mg, 1.0 mmol) was added, and the reaction was refluxed for 6 h. The mixture was evaporated to dryness and chromatographed on a silica gel column using ether/petroleum ether/triethylamine (1:1:15%) eluant to yield cis 75 mg (70%) $R_f$ 0.50; or trans 54 mg (50%), $R_f$ 0.65 (1% triethylamine in ether/petroleum ether; 1:1). m/z 539 (M$^+$, 100), 524(20), 312(30), 191(30), 100(60), 86(100). trans m/z 539 (M$^+$, 100), 524(30), 452(20), 312(20), 191(30), 100(60), 86(100). The $^1$HNMR and $^{13}$CNMR assignments are shown in Table 5.

The end product N,N-Diethyliodomethyltamoxifen will then be radiolabeled with $^{131}$I, as described in Example 12.

EXAMPLE 9

SYNTHESIS OF N,N-DIETHYLBROMOMETHYLTAMOXIUEN (COMPOUND XI)

The present example is provided to demonstrate the most preferred method and best mode for preparing the bromo-tamoxifen analogs of the present invention. Generally, the bromomethyl-tamoxifen analogs were prepared by treatment of a tamoxifen hydroxy precursor with $CBr_4$ in 50% yields. The IC-50 with Br per μm was 0.2. The bromomethyl-Tx analogs were found to bind to estrogen receptors greater than other halogenated tamoxifens tested with F, Cl, or I.

Synthesis

1-[4-(2-Diethylaminoethoxy)phenyl]-1,2-diphenyl-5-bromo-1-entene (N N-Diethylbromomethyltamoxifen)

Triphenylphosphine (105 mg, 0.4 mmol) was added to a stirred solution of hydroymethyltamoxifen (85 mg. 0.2 mmol) (1) and carbon tetrabromide (100 mg, 0.6 mmol) in THF (10 ml). After 2 h, the reaction mixture was filtered and the filtrate was evaporated to dryness. The mixture was reconstituted in chloroform (100 μl) and chromatographed on a silica gel column using ether/petroleum ether/triethylamine (1:1:10%) as eluant to yield the cis (36 mg, 37%) or trans (39 mg, 40%) product. Elemental analysis - ($C_{29}H_{34}NOBr$) C,H,N: Calc. Trans - C:70.72, H:6.96, N:2.84, Found Trans - C:70.45, H:7.11, N:2.68; Calc. Cis ($H_2O$) - C:68.29, H:7.11, N:2.99, Found Cis - C:68.70, H:7.63, N:2.74. Trans - m/z 493 (20 mt), 491 (20); Cis - m/z 493 (20, M+), 491(20), 267 (20), 252 (30), 191 (40), 86 (100).

EXAMPLE 10

SYNTHESIS OF N,N-DIETHYLCLOROMETHYLAMOXIFEN COMPOUND (XII)

The present example is provided to demonstrate the most preferred method and best mode for preparing the chloro-tamoxifen analogs of the present invention. Generally, the chlioromethyl analogs were prepared by treatment of hydroxy precursor with $SOCl_2$ (87% yield). The IC-50 (μM) for Cl was 0.4.

Synthesis

1 [4-(2-Diethylaminoethoxy)phenyl]-1,2-diphenyl-5-chloro-1-pentene (N,N-Diethylchloromethyltamoxifen)

Thionyl chloride (1 ml) was added to stirred solution of cis or trans hydroxymethyltamoxifen (110 mg, 0.26 mmol) in benzene (25 ml). The mixtures were refluxed for 1 h. Thin-layer chromatography indicated one spot ($R_f$=0.45, $Et_2O$/petroleum ether/triethylamine; 1:1:10%). The reaction mixtures were evaporated and passed through a silica-gel Sep-Pak column eluted with $Et_2O$/petroleum ether/triethylamine (1:1:10%). The cis isomer obtained was 100 mg (87%); the trans isomer was 90 mg (78%). HPLC analysis showed that the retention time for cis isomer was 5.17 min and trans isomer was 5.34 min at flow rate 2 ml/min, U.V.=254 nm, on a C-18 column, mobile phase: acetonitrile:water:triethylamine (85:15:1%); U.V.=254 nm. Elemental analysis - ($C_{29}H_{34}NOCl$) C,H,N: Calc. (cis= trans) - C:77.74, H:7.65, N:3.12, Found Cis - C:77.28, H:7.83, N:3.01; Found Trans - C:77.45, H:7.73, N:2.87. Trans - m/z 450 (20, M+), 448 (60), 447 (100); Cis - m/z 450 (15, M+), 448 (45), 447(50);

TABLE 2

| | Elemental Analysis | | | | | |
|---|---|---|---|---|---|---|
| | Bromide | | | Chloride | | |
| | | Found | | | Found | |
| | Calc. | H$_2$O | Cis(H$_2$O) | trans | Calc. | Cis | trans |
| C | 70.72 | 68.29 | 68.70 | 70.45 | 77.74 | 77.28 | 77.45 |
| H | 6.96 | 7.11 | 7.63 | 7.11 | 7.65 | 7.83 | 7.73 |
| N | 2.84 | 2.99 | 2.74 | 2.68 | 3.12 | 3.01 | 2.87 |

EXAMPLE 11

$^1$H-NMR AND $^{13}$C-NMR ASSIGNMENT OF FLUOROTAMOXIFEN DERIVATIVES $^1$HNMR Assignment Assignment of $^1$H-NMR for compound VI and X was done by two dimensional NMR which includes COSY, Long Range COSY and HC COSY, Long Range HC COSY (COSY Homonuclear Chemical Shift Correlation). The aromatic portion is subdivided into three isolated spin systems at 200 MHz. In the trans isomer, two spin systems were readily established for aromatic protons a and b (Shanni, 1985; McCague, 1988). For compound VI, a correlation among the H1 methylene protons (resonates at 2.76 ppm for cis and 2.55 ppm for trans), the H2 germinal methylene protons (resonates at 1.79 ppm for cis and 1.80 ppm for trans) and H3 protons (resonates at 4.38 ppm for cis and 4.42 ppm for trans) was observed during the analysis of the COSY Spectrum as shown in Table 4. In addition, the protons at the 4 and 5 - ethylene bridge correlated with each other using the COSY spectrum analysis. H-5 resonates down field at 3.99 ppm (cis) and 3.91 ppm (trans) whereas H-4 resonates at 2.8 ppm (cis) and 2.79 ppm (trans). H-6 protons of the ethyl group showed a gradruplet (resonates at 2.57 ppm for cis and 2.57 ppm for trans) which directly correlates with H-7 methyl protons at 1.01 ppm (cis) and 1.03 ppm (trans). The $^1$HNMR data are shown at Table 3.

TABLE 3

$^1$H NMR DATA OF TAMOXIFEN DERIVATIVES
(Carbon number shown at Table 6)

| | H-1 | J$_{1,2}$ | J$_{1,2}$ | H-2 | H-3 | J$_{3,4}$ | J$_{3,4}$ | H-4 |
|---|---|---|---|---|---|---|---|---|
| II (Cis) | 2.79 | 6.3 | 6.3 | 3.96 | 2.70 | 7.1 | 7.1 | 3.49 |
| II (trans) | 2.72 | 6.2 | 6.3 | 3.88 | 2.76 | 7.1 | 7.1 | 3.54 |
| III (Cis) | ≈2.48 | — | 6.3 | 3.99 | ≈2.64 | — | 7.3 | 1.56 |
| III (trans) | ≈2.45 | — | 6.4 | 3.90 | 2.77 | 6.4 | 7.3 | 1.59 |
| VIII (Cis) | 2.91 | 6.3 | 7.1 | 3.94 | 2.84 | 7.1 | 6.3 | 4.07 |
| VIII (trans) | ≈2.80 | — | — | ≈3.89 | ≈2.76 | — | — | ≈3.94 |
| IX (Cis) | | 2.48 | 6.0 | 6.3 | 3.90 | 2.90 | 6.0 | 7.11.66 |

$^{13}$C-NMR Assignment

Proton resonance assignments were unequivocally assigned by COSY spectrum. Protonated carbon resonance was assigned from HC-COSY spectrum. The chemical shift for cis and trans isomers of compound VI is shown in Table 4 and for compound X is shown in Table 5.

TABLE 4

$^{13}$C (50 MHz) and $^1$H (200 MHz) NMR ASSIGNMENTS FOR
N,N-DIETHYLFLUOROMETHYLTAMOXIFEN (VI) in CDCL$_3$

| Atom | $^1$H (±0.02 ppm) Trans | $^1$H (±0.02 ppm) Cis | No. of protons Trans/Cis | $^1$H (multiplicity) J$_{HH}$ (Hz) Trans | $^1$H (multiplicity) J$_{HH}$ (Hz) Cis | No. of carbons | $^{13}$C (ppm) J$_{HH}$ (Hz) Trans | $^{13}$C (ppm) J$_{HH}$ (Hz) Cis |
|---|---|---|---|---|---|---|---|---|
| Ar | 7.25 | 7.23 | 10H | m | m | 6C | 130–157 | 130–157 |
| | | | | | | 10C | 126–132 | 126–131 |
| a | 6.79 | 7.10 | 2H | d(6.8) | m | 1C | 113.5 | 114.2 |
| b | 6.56 | 7.00 | 2H | d(6.8) | m | 1C | 113.5 | 114.2 |
| 3 | 4.42 | 4.38 | 2H | dt(7.3) (6.1) | dt(47.3) (6.10) | 1C | 85.2 (d;165) | 83.5 (d;165) |
| 5 | 3.91 | 3.99 | 2H | t(6.4) | t(6.37) | 1C | 66.3 | 66.6 |
| 4 | 2.79 | 2.80 | 2H | t(6.4) | t(6.37) | 1C | 51.7 | 51.9 |
| 6 | 2.56 | 2.57 | 4H | m | m | 2C | 47.8 | 47.9 |
| 1 | 2.55 | 2.76 | 2H | m | m | | 31.6 (d;5.5) | 31.5 (d;5.5) |
| 2 | 1.8 | 1.79 | 2H | m | m | 1C | 29.8 (d;44.3) | 29.9 (d;19.5) |
| 7 | 1.03 | 1.01 | 6H | t(7.2) | t(7.2) | 2C | 11.8 | 11.8 |

TABLE 5

$^{13}$C (50 MHz) and $^1$H (200 MHz) NMR ASSIGNMENTS FOR
N,N-DIETHYLFLUOROMETHYLTAMOXIFEN (X) in CDCL$_3$

| Atom | $^1$H (±0.02 ppm) Trans | $^1$H (±0.02 ppm) Cis | No. of protons Trans/Cis | $^1$H (multiplicity) J$_{HH}$ (Hz) Trans | $^1$H (multiplicity) J$_{HH}$ (Hz) Cis | No. of carbons | $^{13}$C (ppm) J$_{HH}$ (Hz) Trans | $^{13}$C (ppm) J$_{HH}$ (Hz) Cis |
|---|---|---|---|---|---|---|---|---|
| Ar | 7.40 | 7.20 | 10H | m | m | 6C | 135–157 | 135–157 |
| | | | | | | 10C | 126–131 | 126–131 |
| a | 6.76 | 7.10 | 2H | d(8.8) | m | 1C | 113.37 | 114.3 |
| b | 6.54 | 7.00 | 2H | d(8.8) | m | 1C | 113.37 | 114.3 |
| 5 | 3.90 | 4.06 | 2H | t(6.4) | t(6.4) | 1C | 66.16 | 66.64 |
| 4 | 3.02 | 3.04 | 2H | t(7.1) | t(7.0) | 1C | 51.59 | 51.85 |
| 3 | 2.78 | 2.88 | 2H | t(6.4) | t(6.4) | 1C | 6.38 | 6.19 |
| 6 | 2.50 | 2.70 | 4H | m | m | 2C | 47.77 | 47.89 |
| 1 | 2.50 | 2.70 | 2H | m | m | 1C | 37.05 | 37.06 |

TABLE 5-continued $^{13}$C (50 MHz) and $^1$H (200 MHz) NMR ASSIGNMENTS FOR
N,N-DIETHYLFLUOROMETHYLTAMOXIFEN (X) in CDCL$_3$

| | $^1$H (±0.02 ppm) | | No. of protons | $^1$H (multiplicity) J$_{HH}$ (Hz) | | No. of carbons | $^{13}$C (ppm) J$_{HH}$ (Hz) | |
|---|---|---|---|---|---|---|---|---|
| Atom | Trans | Cis | Trans/Cis | Trans | Cis | | Trans | Cis |
| 2 | 1.86 | 1.86 | 2H | pent (7.4) | pent (7.4) | 1C | 32.92 | 32.92 |
| 7 | 1.02 | 1.02 | 6H | t(7.1) | t(7.1) | 2C | 11.77 | 11.95 |

EXAMPLE 12

RADIOSYNTHESIS OF [$^{18}$F] FLUOROMETHYLTAMOXIFEN AND [$^{131}$I] ODOMETHYLTAMOXHFEN FROM FLUOROMETHYL TAMOXIFEN AND IODOMETHYL TAMOXIFEN

[$^{18}$F]Fluoride was produced at the University of Texas Health Science Center, Cyclotron Facility, by proton irradiation of [$^{18}$O]water (99.4% isotopic enrichment, ISOTEC INC., Miamisburg, Ohio) in a small volume silver target. Aliquots containing 200–400 mCi of $^{18}$F activity were combined with kryptofix-2,2,2 (26 mg) and anhydrous potassium carbonate (4.6 mg) heated under reduced pressure to remove [$^{18}$O] water, and dried in a vacutainer tube by azeotropic distillation with dry acetonitrile (3×1.5 ml). The trans tosyl analog of tamoxifen (5 mg) was dissolved in acetonitrite (1.5 ml), added to the kryptofix/[$^{18}$F]fluoride complex, and then heated at 95° C. for 10 min. After cooling, the reaction mixture was passed through a silica gel packed column (SPE-500 mg) (Whatman Lab, Clifton, N.J.) and eluted with ether/petroleum ether/triethylamine, 5:5:1 (3×1.5 ml). The [$^{18}$F]-displacement reaction produced 100–130 mCi (47-62% yield, decay corrected) of the product. The solvent was evaporated under N$^2$; the resulting mixture was hydrolyzed with 2N HC1 (1 ml) for 10 min to remove unreacted starting material and then made basic (pH 10) with 2N NaOH (1 ml). After extraction with methylene chloride (CH$^2$Cl$^2$, 1 ml), the mixture was purified by passage through a silica gel column (SPE-500 mg) and elusion with ether/petroleum ether/triethylamine, 5:5:1 (4×1.5 ml). Once the solvent was evaporated, a yield of 58–100 mCi of product wa isolated (30–40% yield, decay corrected) at end-of-synthesis (EOS) 60–70 min.

HPLC wa performed on a C-18 Radial-Pak column, 8×100 mm, with 1% triethylamine in acetonitrile/water, 85:15, using a flow rate of 1.5 ml/min. The no-carrier-added product corresponded to the retention time (5.6 min) of the unlabeled fluoro analogue under similar conditions.

[$^{18}$F] FLUOROMETHYLTAMOXIFEN

In a typical procedure, potassium [$^{18}$F]fluoride (from azeotropic evaporation of $^{18}$F (H$_2$$^{18}$O) in acetonitrile in the presence of K$_2$ (03 and Kryptofix 2,2,2)(3 mCi, 200 μl) was transferred to a reaction vessel with the tosylmethyl analog of tamoxifen (compound IX N,N-dimethyl-O-tosylmethyltamoxifen) (1 mg). Tosylmethyl analog was prepared essentially as described in Example 6. The vessel was sealed and warmed at 100° C. for 20 minutes, treated with 6 N HCl (200 μl), heated for an additional 10 min, and then spotted on a silica gel coated TLC plate for separation (ether/petroleum ether/triethylamine; 1/1/10% or chloroform/methanol; 9/1).

Authentic non-labeled fluorotamoxifen was used to confirm the presence of F-18 labeled compound. The TLC plate was cut into 0.5 cm zones for counting the activity. Using a Davidson multichannel analyzer fitted with a well type NaI crystal with appropriate shielding. The radiochemical yield was determined as 60%. The reaction mixture was passed through a silica Sep-Pak eluted with 10% triethylamine in ether/petroleum ether (1/1). The radiochemical purity was examined using HPLC (C-18 Radial-Pak column, 8×100 mm, 1% triethylamine in acetonitrile/water [85/15], flowrate of 1.5 mi/min). The retention time of compound VI (N,N-diethylfluoromethyltamoxifen) was 5.60 min. Radiochemical purity was >99%. A typical batch had a specific activity of approximately 4–6 Ci/μmol.

[$^{131}$I] IODOMETHYLTAMOXIFEN

For a typical $^{131}$I displacement experiment, Na$^{131}$I (1mCi) was added to a vial containing tosyimethyltamoxifen (IX)(2 mg) in acetone. The reaction was heated at 100° C. for 30 min. and 6 N HCl was added. After 20 minutes, the vial was cooled and the reaction mixture was chromatographed on a silica-gel Sep-Pak column eluted with 1% triethylamine in ether:petroleum ether (1:1). The purity of the [131-I] labeled tamoxifen analog was assessed by HPLC and compared to authentic compound. The HPLC retention time for Compound X was 22 minutes (Acetonitrile:water:triethylamine [85:15:1]).

EXAMPLE 13 in vitro ESTROGEN RECEPTOR BINDING WITH TAMOXIFEN DERIVATIVES

The present example demonstrates the utility of the described fluorotamoxifen and iodotamoxifen derivatives for binding estrogen receptors in vitro and to demonstrate the utility of employing these tamoxifen derivatives in vivo in various diagnostic and therapeutic applications involving imaging of estrogen receptor-containing tissues.

The relative binding affinity of the tamoxifen derivatives synthesized in Examples 1–8 and of native tamoxifen (Compound I) to estrogen receptor was determined. A previously reported procedure was modified by the inventors and used for this purpose.[10,11] TEA buffer was used by the Inventors for tissue preparation.

Briefly, uteri (90 gm) were obtained from immature domestic swine (15 kg) was homogenized in Tris buffer (10 mM, pH 7.4) (1 uterus/180 ml), which contained EDTA (1.5 mM) and sodium Azide (3 mM). The homogenate was centrifuged at 100,000 g for 1 hour at 4° C. Uteri cytosol (contains 2% of protein from corresponding uterus tissue) were then pretreated with dextran-coated charcoal as described.[10] Protein concentrations were determined according to the method of Lowry et al.[12]

To investigate the nature of the interaction of estradiol with the estrogen receptor site, a saturation curve (FIG. 2) was obtained for [$^3$H]estradiol ($10^{-5}$ M to $10^{-10}$ M) in the presence or absence of excess estradiol ($2 \times 10^{-5}$ M). Uteri cytosol (2 mg protein/tube) were incubated at 4° C. for 2 h with [$^3$H]estradiol (5 nM/tube) and competitor [ranging from $10^{-4}$ M to $10^{-8}$ M ("specific") or with $10^{-5}$ M estradiol (non-specific)].

Figure 3:
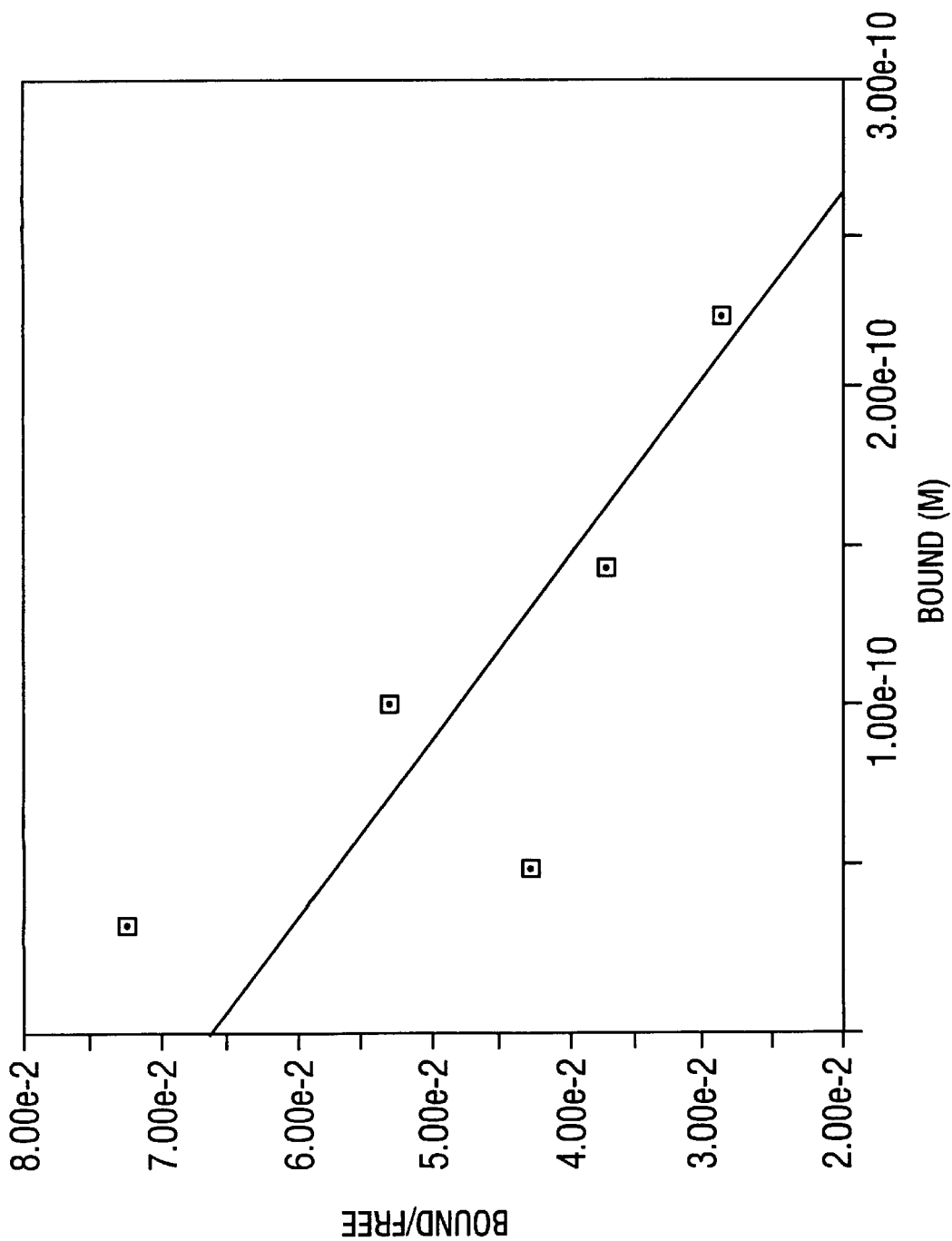
FIG. 3 Estrogen receptor Scatchard plot analysis. This is to demonstrate that estradiol has competitive reversible binding. The receptor density of pig uterus and affinity constant (Kd) were determined.

A Scatchard analysis indicated a single class of binding sites with a mean $K_d$ of 5 nM (n=9) and a mean $B_{max}$ of 376 fmol/mg protein with a Hill coefficient of 0.982 (FIG. 3).

Various tamoxifen derivatives were then tested for their ability to displace the [$^3$H]estradiol (5 nM) bound to estrogen receptors in this in vitro pig uterus system. From these experiments, the concentration of test compounds which decreased 50% of specific radioligand binding ($IC_{50}$) and the inhibition constant ($K_i$) were determined[9] for various tamoxifen derivatives and the results summarized in Table 5.

Tamoxifen (I) (i.e., the fluorotamoxifen derivative) binds to the estrogen receptor with high affinity as tamoxifen ($K_i$=15,000 nM) (Table 6). The affinity of the trans isomer of N,N-diethylfluorotamoxifen (IV) for the estrogen receptor is two and a half times that of tamoxifen. In addition, the trans isomer has a higher binding affinity than the cis isomer. Increasing the side chain by one carbon resulted in the formation of fluorinated compound VI, which showed a 6-fold (cis) and 30-fold (trans) higher affinity for the estradiol binding site than tamoxifen. The iodinated compound (X) showed 10–15 fold higher estrogen receptor affinity than native tamoxifen.

TABLE 6

STRUCTURES AND RELATIVE BINDING AFFINITIES OF TAMOXIFEN DERIVATIVES

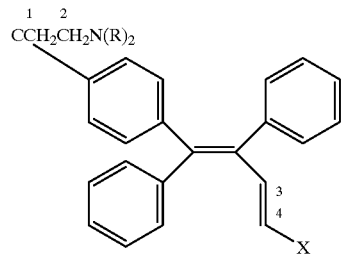

| Compound | R | X | RBA* | $IC_{50}$(M) | $K_i$(nM) |
|---|---|---|---|---|---|
| I (Tamoxifen) | $CH_3$ | H | 100 | $3 \times 10^{-5}$ | 15,000 |
| II | $C_2H_5$ | OH | | | |
| III | | | | | |
| (Cis) | $C_2H_5$ | $CH_2OH$ | 300 | $1 \times 10^{-5}$ | 5,000 |
| (trans) | | | 400 | $7 \times 10^{-6}$ | 3,500 |
| IV | | | | | |
| (Cis) | $C_2H_5$ | F | 100 | $3 \times 10^{-5}$ | 15,000 |
| (trans) | | | 250 | $1.2 \times 10^{-5}$ | 6,000 |
| V | $CH_3$ | OH | | | |
| VI | | | | | |
| (Cis) | $C_2H_5$ | $CH_2F$ | 600 | $5 \times 10^{-6}$ | 2,500 |
| (trans) | $C_2H_5$ | $CH_2F$ | 3,000 | $1 \times 10^{-6}$ | 500 |
| VII (trans) | $CH_3$ | F | 100 | $3 \times 10^{-5}$ | 15,000 |
| VIII | $C_2H_5$ | O-tosyl | — | — | — |
| IX | $C_2H_5$ | $CH_2O$- | | | |

TABLE 6-continued

STRUCTURES AND RELATIVE BINDING AFFINITIES OF TAMOXIFEN DERIVATIVES

| Compound | R | X | RBA* | $IC_{50}$(M) | $K_i$(nM) |
|---|---|---|---|---|---|
| X | | tosyl | | | |
| (cis) | $C_2H_5$ | $CH_2I$ | 1,000 | $3 \times 10^{-6}$ | 1,500 |
| (trans) | | | 1,500 | $2 \times 10^{-6}$ | 1,000 |
| Estradiol | | | 15,000 | $2 \times 10^{-7}$ | 100 |

*The relative binding affinity (RBA) for the pig uteri estrogen receptor is the ratio between the concentration of unlabeled tamoxifen and the competitor (× 100) (i.e., tamoxifen is 100 as the standard) required to decrease the amount of bound [$^3$H]estradiol by 50%. Incubation was done at 4° C. The data was reproduced in triplicate. The protein concentration was determined to be 1 mg per tube.

EXAMPLE 14 in vitro ESTROGEN RECEPTOR BINDING—COMPARISON OF HALOGENATED TAMOXIFEN DERIVATIVES The present example demonstrates the estrogen binding activity of various halogenated tamoxifen analogs. The particular halogenated tamoxifen analogs employed in the present study include:

chloromethyltamoxifen (CMTX);
bromomethyltamoxifen (BrMTX);
fluoromethyltamoxifen (FMTX);
iodomethyltamoxifen (IMTX)

The estrogen receptor binding assay used in the present example was essentially the same on described in Example 13.

Non-radiochemical forms of the fluoromethyltamoxifen and the iodomethyltamoxifen were prepared by reacting tosylmethyltamoxifen with KF/kryptofix or NaI resulting in 65% and 47% yields, respectively. The radiochemical yields for [$^{18}$F]FMTX and [$^{131}$I]IMTX were 48% and 40%.

The chloromethyltamoxifen and bromomethyltamoxifen analogs were prepared by treatment of hydroxytamoxifen precursor with $SOCl_2$ or $CBr_4$ resulting in 87% and 50% yields, respectively.

The $IC_{50}$'s for fluoromethyl, chloromethyl, bromomethyl and iodomethyl (F, Cl, Br, I and TX) were 1, 0.4, 0.2, 2 and 30 $\mu$M, respectively. These data demonstrate that halogenated tamoxifen analogs, as described herein, compete with [$^3$H]estradiol (5 nM) in binding estrogen receptors.

Bromomethyl tamoxifen, as demonstrated in Table 7, binds to estrogen receptors with greater affinity than the other halogenated tamoxifen analogs tested. These alkyl halogenated tamoxifen analogs, particularly the bromo analogs, are thus expected to be particularly efficacious in the mapping estrogen receptors.

TABLE 7

EFFECT OF HALO ALKYL (METHYLATED) TAMOXIFEN ANALOGS ON ESTROGEN RECEPTOR BINDING[1]

| Compound | $IC_{50}$ (uM)[2] | RBA[3] |
|---|---|---|
| F trans | 1 | 30 |
| Cis | 5 | 6 |
| Cl trans | 0.4 | 75 |
| Cis | 4 | 7.5 |
| Br trans | 0.2 | 150 |
| Cis | 0.8 | 37.5 |
| I trans | 2 | 15 |
| Cis | 3 | 10 |
| Tamoxifen trans | 30 | 1 |
| OH trans | 7 | 4 |
| Cis | 10 | 3 |

[1] Each value shown for $IC_{50}$ and RBA represents the average of three experiments. In each experiment, triplicate samples were tested.
[2] $IC_{50}$: Concentration required to decrease the amount of bound [$^3$H] estradiol by 50%.
[3] RBA: Relative binding affinity is the $IC_{50}$ ratio between tamoxifen and competitor (× 100).

EXAMPLE 15

INHIBITION OF BREAST TUMOR CELL GROWTH IN VITRO BY HALOGENATED TAMOXIFEN ANALOGS

The present example demonstrates the in vitro effect of fluoro, chloro, bromo and iodo-alkyl halogenated tamoxifen analogs on human breast tumor cell growth. This in vitro test demonstrates also the utility of these halogenated tamoxifen analogs for the in vivo treatment of estrogen-dependent cancers, such as human breast and uterine cancers. An additional object of this example was to establish the utility of using the described radiolabeled, alkyl halogenated tamoxifen derivatives as imaging agents for imaging estrogen receptor positive tumors in vivo and to demonstrate the applicability of using the described alkyl halogenated tamoxifen analogs as anti-cancer agents in vivo. It is anticipated that the presently described halogenated tamoxifen analogs will be useful in the treatment of estrogen-dependent breast and uterine cancers, as well as other estrogen-dependent cancer cell growths.

The aliphatically halogenated tamoxifen derivatives described herein (FIG. 1 and Examples 1–12) were used together with an in vitro breast tumor cell system to identify which of these agents might offer advantages over other agents currently in use for the treatment and diagnosis of estrogen receptive tumors.

The MCF7 cell line is a human tumor cell line. This cell line was cultured in MEM (Eagles) media in a 5% $CO^2$ atmosphere with 10% fetal calf serum that had been washed twice with dextran coated charcoal to reduce endogenous estrogen levels. The media was supplemented with 1 mM sodium pyruvate and 100 μm non-essential amino acids. The cell line was screened routinely for myoplasma contamination using the GenProbe kit (Fisher). Cells were trypsinized and plated at a density of 5,000 cells/well in 96 well microtiter plates and allowed to attach and recover for 24 hours.

The media was removed by aspiration and replaced with filter sterilized drug (concentration from $10^{-4}$M to $10^{-5}$M) in media. The cells were incubated for 72 hours and then stained using the mTT tetrazolium dye assay of Mosmann[36] except that after the media was removed, the blue formazan product was solubilized in 50 μl/well DMSO. Plates were shaken for 1 minute and read on a Dynatech MR600 microplate reader within an hour at a transmission wavelength of 570 nm and reference wavelength of 630 nm.

Compound III (N,N-diethylhydroxymethyltamoxifen), IV (N,N-diethylfluorotamoxifen), VI (N,N-diethylfluoromehtyltamoxifen), VII (fluorotamoxifen), X (N,N-diethyliodomethyltamoxifen), XI (N,N-diethylbromomethyltamoxifen), and XII (N,N-diethyl-chloromethyltamoxifen) were prepared substantially as described in Examples 1–10.

The results of the 72 hour exposure of MCF7 tumor cell line to tamoxifen or analogs are summarized in Table 8. cis N,N-diethylfluoromethyltamoxifen was 3-fold more potent than tamoxifen control against this tumor cell line. In addition, both cis N,N-diethyl-fluoro, fluoromethyl- and iodomethyl isomers appear to be more potent than the trans isomers.

These results demonstrate that the described fluorotamoxifen derivatives, particularly compounds IV (cis), VI (cis and trans) and X (cis and trans) are effective as inhibiting a breast tumor cell line, and further support the reasonable expectation that these highly specific derivatives would be effective as an anti-cancer agent in treating human breast cancer.

In summary, this study demonstrates that halogenated tamoxifens with the halogen atom placed on the aliphatic chain bind to estrogen receptors in vitro and can be labeled with $^{18}$F and $^{131}$I, thus reflecting a utility for imaging estrogen receptors by PET and SPECT. Also, the data obtained from in vitro receptor assays suggested that the disclosed tamoxifen derivatives, particularly N,N-diethylfluoromethyltamoxifen and N,N-diethyliodomethyltamoxifen, may be potential ligands for mapping the estrogen receptor by PET and SPECT.

TABLE 8

EFFECT OF HALOGENATED TAMOXIFEN ANALOGS ON HUMAN BREAST TUMOR CELL GROWTH in vitro[1]

| Compound | $IC_{50}$ Dose (μM)[2] | RP[3] |
|---|---|---|
| trans-tamoxifen (control) | 1.0 (14.6) | 100 |
| (III) OH | | |
| (Cis) | 16.7 | 66 |
| (trans) | 22.0 | 50 |
| (IV) F | | |
| (Cis) | 4.1 | 268 |
| (trans) | 13.4 | 82 |
| (VI) FM | | |
| (Cis) | 4.5 | 244 |
| (trans) | 11.8 | 93 |
| (VII) FTX | | |
| (Cis) | 4.5 | 224 |
| (trans) | 11.8 | 93 |
| (X) IM | | |
| (Cis) | 2.36 | 466 |
| (trans) | 6.3 | 175 |
| (XI) BrM | | |
| (Cis) | 0.62 | 2355 |
| (trans) | 4.9 | 298 |

TABLE 8-continued

EFFECT OF HALOGENATED TAMOXIFEN ANALOGS ON
HUMAN BREAST TUMOR CELL GROWTH in vitro[1]

| Compound | IC$_{50}$ Dose ($\mu$M)[2] | RP[3] |
|---|---|---|
| (XII) ClM | | |
| (Cis) | 4.36 | 335 |
| (trans) | 10.0 | 146 |

[1]·Cell line used was MCF7. Data represents average of three experiments.
[2]·IC$_{50}$ indicates the concentrations required to inhibit 50% of MCF$_7$ cells growth.
[3]·Relative potency (RP) indicates the IC$_{50}$ ratio between tamoxifen and competitor.

EXAMPLE 16 in vivo BIODISTRIBUTION IN RATS OF ADMINISTERED N,N-DIETHYL-[$^{18}$F] FLUOROMETHYLTAMOXIFEN VI)

The present example is presented to demonstrate the particular biodistribution characteristics of an alkyl halogenated tamoxifen derivative administered in an in vivo system.

Four groups of rats (150–200 gm, N=4/group) were anesthetized with ketamine (10–15 mg/rat). Pure N,N-diethyl-$^{18}$[F]fluoromethyltamoxifen (specific activity>6 Ci/$\mu$mol) was reconstructed in 5% ethanol-saline solution, and 10 $\mu$C of this tracer was given (i.v., tail-vein) into estrogen-primed female Sprague-Dawley rats ("primed"=60 $\mu$g estradiol, s.c., 3 days). Tissue uptake of $^{18}$F-tracer was determined at 2 and 4 hours (h). To ascertain whether the $^{18}$F-tracer uptake was mediated by a receptor-process, one group of rats was given $^{18}$F-tracer without priming with estradiol; and another group of rats was given unlabeled estradiol (30 $\mu$g/rat) together with $^{18}$F-tracer. The amount of unlabeled estradiol given to rats should occupy estrogen receptors and chase out the $^{18}$F-tracer's radioactivity from uterus.

TABLE 9

BIODISTRIBUTION OF N,N-DIETHYL-
[$^{18}$F]FLUOROMETHYLTAMOXIFEN
% OF INJECTED DOSE/GRAM OF TISSUE WEIGHT
OF RAT (N = 4)
(PRIME WITH 60 $\mu$g OF ESTRADIOL FOR 3 DAYS)

| | 2 h | 4 h | 2 h (BLOCK)[1] | 2 h* |
|---|---|---|---|---|
| BLOOD | 0.033 ± 0.0059 | 0.045 ± 0.0003 | 0.048 ± 0.0066 | 0.033 ± 0.0109 |
| LIVER | 4.540 ± 0.5053 | 4.205 ± 0.4397 | 4.451 ± 1.1559 | 3.849 ± 0.4069 |
| KIDNEY | 0.742 ± 0.0756 | 0.796 ± 0.0300 | 0.742 ± 0.1451 | 0.530 ± 0.0752 |
| UTERUS | 0.426 ± 0.0177 | 0.400 ± 0.0312 | 0.297 ± 0.0356 | 0.248 ± 0.0535 |
| MUSCLE | 0.151 ± 0.0203 | 0.183 ± 0.0015 | 0.145 ± 0.0446 | 0.109 ± 0.0218 |
| BONE | 0.653 ± 0.1348 | 0.802 ± 0.0556 | 0.576 ± 0.1268 | 0.644 ± 0.0656 |
| INTESTINE | 0.917 ± 0.3058 | 1.101 ± 0.5986 | 0.742 ± 0.458 | 0.504 ± 0.1784 |
| UTERUS/ BLOOD | 13.5 ± 2.97 | 9.1 ± 1.34 | 6.3 ± 1.62 | 6.6 ± 0.29 |
| UTERUS/ MUSCLE | 2.9 ± 0.43 | 2.2 ± 0.16 | 2.2 ± 0.62 | 2.5 ± 0.37 |

[1]Rats were co-injected with estradial (30 $\mu$g) and F-18 tracer in the blocked group.
*Without prime with estradiol (control); rats weighted about 175 gm.

The uterus to blood ratio at 2 h in rats without priming with estradiol group was 6.6 ±0.29, which changed to 13.5±2.97 in rats primed with estradiol. This increased uptake was blocked by co-injection of estradiol and $^{18}$F-tracer, where the ratio was 6.3±1.62. The data suggest that the uterus uptake by $^{18}$F-fluoro analogue of tamoxifen is mediated by an estrogen receptor process.

PROPHETIC EXAMPLE 17

PROPOSED HUMAN USE OF ALKYL HALOGENATED TAMOXIFEN AND DERIVATIVES AS LIGANDS FOR IMAGING ESTROGEN RECEPTOR POSITIVE TUMORS

The present prophetic example is provided to outline a procedure for the potential utility of the disclosed tamoxifen analogs in imaging estrogen-receptor positive tumor cells in humans. More specifically, the present prophetic example is aimed at outlining a method by which the described lower alkyl halo tamoxifen derivatives molecules may be used to image estrogen receptor positive tumors in vivo, most particularly those which typically occur in breast tissue and uterine tissue.

In a most preferred embodiment of the proposed method, the lower alkyl halotamoxifen derivative, trans-N,N-diethylfluoromethyltamoxifen (compound VI), trans N,N-dieththyl iodomethyltamoxifen (compound X), or bromomethyltamoxifen are the radiopharmaceuticals of choice to be used as the estrogen receptor imaging agent in a standard PET (positron emission tomography) and SPECT analysis. Of these, bromomethyltamoxifen produced the most superior results in animal studies presented by the Inventors.

The procedure for conducting estrogen receptor mapping would be substantially the same as that outlined by Minton et al.[4] The most significant modification of this procedure, among others, is that the estradiol-based derivatives described by Minton would not be used. The more specific aliphatic chain substituted tamoxifen derivatives of the claimed invention would be used.

Briefly stated, the most preferred method for imaging estrogen receptors in breast tumor tissue of a patient, wherein a radiolabeled alkyl-halogenated tamoxifen derivative (such as N,N-diethyl[$^{18}$F]fluoromethyltamoxifen, N,N-diethyl [$^{131}$I]iodomethyltamoxifen, N,N-diethylcloromethyltamoxifen or N,N-diethylbromomethyltamoxifen) is employed as the imaging agent, comprises the following steps: administering to the patient a sufficient amount (about 10 mCi) of radiolabeled alkyl-halogenated tamoxifen derivative to the breast tissue of the patient. The patient is then to be placed in a supine position in the PET device, at which time an emission scan of the chest at the level of the breast mass is to be performed.

The technique for performing an emission scan of the chest is well known to those of skill in the art, and the general procedure for this technique is described by Mintun et al.,4 which reference is specifically incorporated herein for this purpose.

Most preferably, the emission consecutive transaxial scan is to be performed for a 15 minute duration and most preferably about 110 minutes after the injection of the radiolabeled alkyl halogenated taruoxifen derivative. Most preferably, the tumor location is to be confirmed by palpation of the tissue after the patient is in the described supine position. The μCi/ml/pixel of tumor uptake will then be determined.

The PET images obtained are then to be evaluated for the presence or absence of focally increased uptake of the radiolabeled alkl halogenated tamoxifen fluorotamoxifen ligand in the breasts and in the axillae as these were included in the field of view of the PET scanner. Those sites determined from the PET images to have demonstrated potential uptake are to be designated as accordingly abnormal foci uptake of the radiolabeled alkyl halogenated tamoxifen derivative.

The most preferred radiolabeled alkyl halogenated tamoxifen derivative to be used in the mapping and imaging of estrogen receptors in human tissue is N,N-diethylbromomethyltamoxifen.

PROPHETIC EXAMPLE 18

PROPOSED USE OF ALKYL HALOGENATED TAMOXIFEN AND DERIVATIVES IN TREATING CANCER

The present prophetic example is provided to outline a procedure which could be employed for the potential utility of the described alkyl-halogenated tamoxifen derivatives in a treatment regimen for cancer in an animal.

While all of the aliphatic chain substituted tamoxifen derivatives described herein are expected to be useful in an animal treatment regimen, the lower alkyl halotamoxifen derivatives are most preferred. Among the lower alky halogen tamoxifen derivatives described herein, N,N-diethylfluoromethyltamoxifen is most particularly referred.

The methods are postulated to be effective in the treatment of cancers which are estrogen-receptor positive, such as estrogen receptor positive breast cancers. The frequency and dosage amount of the disclosed tamoxifen derivatives would be optimized according to standard techniques, which are well known to those skilled in the art.

EXAMPLE 19

RADIOSYNTHESIS OF [$^{131}$I]-IODO ANALOG OF TAMOXIFEN AND BIODISTRIBUTION

The present example demonstrates the synthesis and biodistribution characteristic of $^{131}$I-iodotamoxifen in mammary tumor.
Synthesis of $^{131}$I-Iodo Analogue of Tamoxifen The transosyl analogue of tamoxifen (10 mg) was dissolved in acetone (1 ml). Na$^{131}$I (3.15 mCi in 0.2 ml borate buffer, pH 8.5) was added. The reaction mixture was heated at 100° C. for 2 h. Acetone was then evaporated under N$_2$. The unreacted tosyl analogue was hydrolyzed with 2N HCl (1 ml) at 110° C. for 15 minutes. The mixture was basified with 2N NaOH (1.5 ml). The product was extracted from CH$_2$Cl$_2$ (2 ml) and purified from a silica gel packed column (SPE 500 mg, Waters, Cliffton, N.J.). The column was eluted with 10% triethylamine in ether: petroleum ether (1:1) (4×1.5 ml). The solvent was evaporated and the final product was reconstituted in 0.05 M citric acid (10 ml). The product isolated was 690 μCi. Radio-thin layer chromatogram indicated one peak which corresponded to unlabeled iodo analogue of tamoxifen with Rf=0.65 from 10% triethylamine in either:petroleum ether (1:1) (J Pharm Sci. 81:622–625, 1992).

In animal tissue distribution studies, each rate was given 8.9 μCi (0.15 ml) tracer intravenously. The tumor-bearing rats were killed at 1, 3, 6 and 24 h. To demonstrate uptake of $^{131}$I-iodotamoxifen is from an estrogen receptor mediated process, a group of rats was pretreated with diethylstilbestrol (DES, 1.2 mg) 1 hour prior to giving tracer. The amount of DES given should occupy tumor estrogen receptor sites. The methods for inducing tumors in rats was as described by those of skill in the art (radiology).
Results of Biodistribution of $^{131}$I-iodotamoxifen The uptake of tumor-to-blood ratios is shown to increase as a function of time in the present studies. The best tumor uptake value was at 24 h postinjection. Thyroid uptake increased only slightly. In blocking studies, both tumor and uterus uptake can be blocked suggesting $^{131}$I-iodotamoxifen uptake in tumor is via a receptor mediated process. Also, other data generated in the inventors laboratory indicate that the tumor dissected from tumor-bearing rat has an estrogen receptor density of 7.5 fmol/mg cytosol protein.

This data validates the use of our animal model for breast tumor uptake studies.

TABLE 10

BIODISTRIBUTION OF $^{131}$I-IODOTAMOXIFEN IN MAMMARY TUMOR-BEARING RATS[1]
(Percent of Injected Dose Per Gram Weight)
(N = 3/Time Interval)

| Tissue | 1 Hour | 3 Hours | 6 Hours | 6 Hours[2] | 24 Hours |
|---|---|---|---|---|---|
| Blood | 0.158 ± 0.0403 | 0.121 ± 0.0925 | 0.124 ± 0.0497 | 0.072 ± 0.0504 | 0.001 ± 0.0001 |
| Lungs | 3.951 ± 0.9932 | 3.709 ± 0.2592 | 2.836 ± 0.6607 | 2.173 ± 0.4207 | 0.512 ± 0.3584 |
| Liver | 5.599 ± 0.5212 | 5.997 ± 0.6861 | 4.630 ± 0.1235 | 4.682 ± 0.7573 | 2.471 ± 0.2074 |
| Kidney | 1.883 ± 0.1116 | 2.372 ± 0.4375 | 1.362 ± 0.1201 | 1.296 ± 0.2317 | 0.381 ± 0.0150 |
| Spleen | 3.379 ± 0.9201 | 3.311 ± 0.5046 | 2.331 ± 0.4077 | 2.366 ± 0.4154 | 0.688 ± 0.1005 |
| Uterus | 0.414 ± 0.0683 | 0.546 ± 0.0666 | 0.408 ± 0.0547 | 0.325 ± 0.0629 | 0.151 ± 0.0110 |
| Muscle | 0.201 ± 0.0296 | 0.253 ± 0.0284 | 0.204 ± 0.1217 | 0.172 ± 0.0548 | 0.005 ± 0.0079 |
| Thyroid | 0.393 ± 0.1209 | 0.748 ± 0.0757 | 0.776 ± 0.1108 | 0.640 ± 0.2137 | 0.493 ± 0.1223 |
| Tumor | 0.181 ± 0.0620 | 0.229 ± 0.1518 | 0.261 ± 0.1659 | 0.217 ± 0.0591 | 0.267 ± 0.0160 |

[1]13762 cell line was inoculated to rats (s.c. 10,000 cells/rat). When tumor size reached 1–2 cm, each rat was administered SuCi tracer.
[2]In blocking studies, each rat was pretreated with DES (1.2 mg i.v.) 1 hr prior to giving tracer.

EXAMPLE 20

BIODISTRIBUTION, PET IMAGING AND TOXICITY OF [$^{18}$F] FLUORO ANALOG OF TAMOXIFEN (FTX) in vivo The present example demonstrates the in vivo biodistribution of $^{18}$F-FTX in mammary tumor-bearing rats. The example is also submitted to demonstrate the further utility of tamoxifen derivative for analysis of human mammary tumor. In addition, the present example demonstrates the estrogen rich tissue specific in vivo distribution of [$^{18}$F] FTX. The pig is employed as an exemplary model for this tissue specific uptake in vivo, and is submitted to demonstrate the utility of these derivatives as radiodiagnostic tools in humans.

Radiosynthesis of [$^{18}$F]Fluoro Analogue of Tamoxifen ($^{18}$F-FTX)

[$^{18}$F] FTX was prepared as described in Example 12.

in vivo Biodistribution of $^{18}$F-FTX in Mammary Tumor-Bearing Rats

Female Fisher 344 rats (250–275 g) (Harlan, Inc., Indianapolis, Ind.) were inoculated with mammary tumor cells using 13762 tumor cell line (s.c. $10^5$ cells/rat). This tumor cell line is specific to Fischer rats. After 14 days, a tumor size was 1–2 cm was observed (see FIG. 15). Four groups of rats (N=3/group) were anesthetized with ketamine (10–15 mg/rat). The trans $^{18}$F-FTX reconstituted in 0.05 M citrate was given to 3 out of the 4 groups of rats (10 μCi/rat, i.v.) and tissue distribution was studied at 30 min. 2 h and 4 h intervals. To ascertain whether tracer uptake occurred via receptors, the fourth group of rats was given diethylstilbestrol (DES 1.2 mg/rat, blocks estrogen receptor sites) for 1 h, followed by 10 μCi of tracer, and tissue distribution studied after 2 hr.

Estrogen receptor assay was performed on tumor tissue (16 g) dissected from 13762 mammary tumor-bearing female rats. The tissue was homogenized in Tris buffer (15 ml) as described previously (Yang et al. (1992) J. Pharm. Sci., 81:622–625), then centrifuge at 100,000 g to prepare a tumor tissue cytosol. This tissue cytosol was then pretreated with dextran-coated charcoal before assay. A saturation curve was obtained for [$^3$H]estradiol ($10^{-5}$–$10^{-10}$ M) in the presence and absence of estradiol ($10^{-5}$M). Scatchard analysis was performed to determine the receptor affinity and density. Protein concentrations were determined according to the method of Lowry.[12]

PET Imaging of Pig Uterus and Ovaries with [$^{18}$F]FTX

The present study is provided to demonstrate the utility of the tamoxifen derivatives for PET imaging of uterus and ovaries, as well as other estrogen receptor-rich tissues.

PET imaging was performed on four domestic female pigs (30 lb) with a positron camera (Positron Corporation, Houston, Tex). Each pig was supine in the scanner so that the detector rings would span the entire pelvic region. Prior to scanning, the position of the uterus and ovaries was determined by hysterosalpingography. Fifteen milliliters of radiopaque (Renografin 76 Squibb Diagnostic, New Brunswick, N.J.) was injected through the vagina into the uterus via a 5 Fr catheter with the balloon inflated by 1 ml of air. Radiographs of the pelvis in the anterior-posterior projection were taken. The location of the uterus was marked permanently on the skin of each pig for positioning in the PET camera. A 20 min attenuation scan was performed with a 4 mCi $^{68}$Ge-ring source prior to tracer injection. After each pig received 10 mCi of [$^{18}$F]FTX, either consecutive 10 min scans were acquired. There was a 5 min wait between scans for data transfer. The total number of counts collected per scan was in the range of 15–30 million. In order to examine the blood clearance profile of [$^{18}$F]FTX, venous blood samples (0.5 ml) were collected every minute for the first ten minutes, followed by every ten minutes up to two hours. Serial transaxial images of the pelvic region were performed in order to view the uterus. The tomograph has a field-of-view of t42 cm on transverse and 12 cm on coronal planes. The axial resolution on the reconstructed plane is 1.2 cm. Twenty-one transaxial slices separated by 5.2 mm were reconstructed and displayed in standard uptake values (SUV) which measures the ratio of tissue [$^{18}$F]FTX uptake to that of the whole body uptake for each scan. To demonstrate that the [$^{18}$F]FTX uptake in the uterus and ovaries occurred via estrogen receptors, each pig was given DES (50 mg) (Miles Inc., West Haven, Conn.) or tamoxifen (10 mg) 30 min before intravenous injection of [$^{18}$F]FTX (10 mCi).

PET Imaging of 13762 Mammary Tumor-Bearing Rat

Rats with tumors 1–2 cm in diameter in lumbar area were given 500 μCi of $^{18}$F-FTX and imaged. The 13762 tumor cell line was originally derived from 7–12-dimethylbenz(a) anthracene (DMBA)-induced rat mammary tumors which have been reported to have estrogen receptors (Kallio et al. (1986) Cancer Chemother. Pharmacol., 17:103–108). In estrogen receptor-positive (ER+) breast cancer patients, receptor positivity was defined equal to or greater than 10 fmol/mg cytosol protein. Levels between 5 and 10 were considered equivocal (Fernandes et al. (1991) CJS, 34:349–355). The data presented herein indicates that the rat tumors have estrogen receptor density of 7.5 fmol/mg of cytosol protein, which is considered at ER(+) level. A serial fifteen minute transaxial image of the rats for one hour by the positron camera was performed.

Animal Acute Toxicity Studies

Acute toxicity studies were performed in BALB/c female mice with doses tested at 20, 50 and 200 mg/kg (i.v., n=5 mice per dose). The fluoro analogue of tamoxifen was prepared in a 5% ethanol solution and 0.1 ml was injected per mouse.

RESULTS

Radiosynthesis

Figure 19:
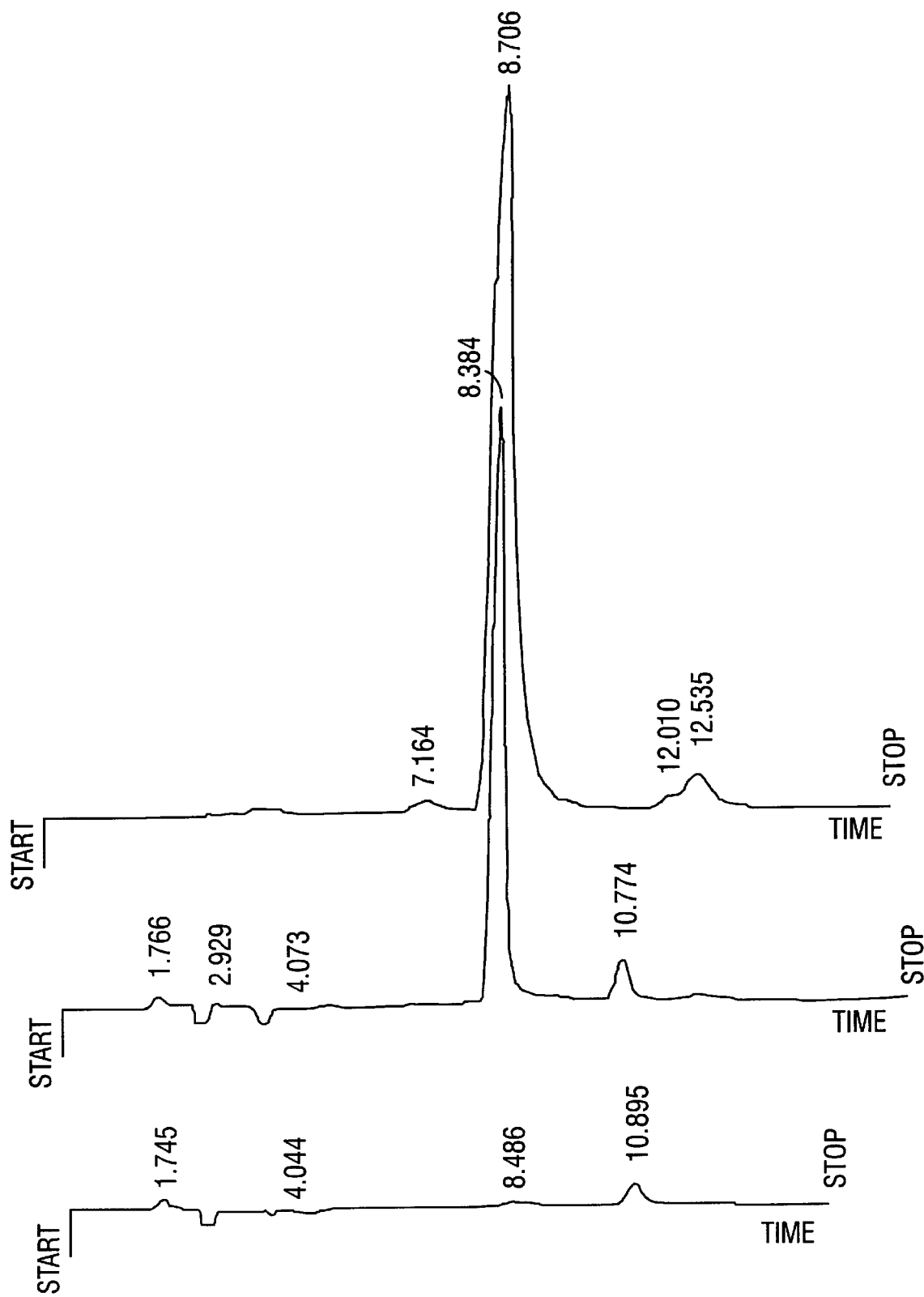
FIG. 19 HPLC CHROMATOGRAM OF THE trans-isomer of the trans-fluoro analog of tamoxifen (A: radiochemical purity, B: unlabeled fluoro analog of tamoxifen (4 μg), C: chemical purity).
Figure 20:
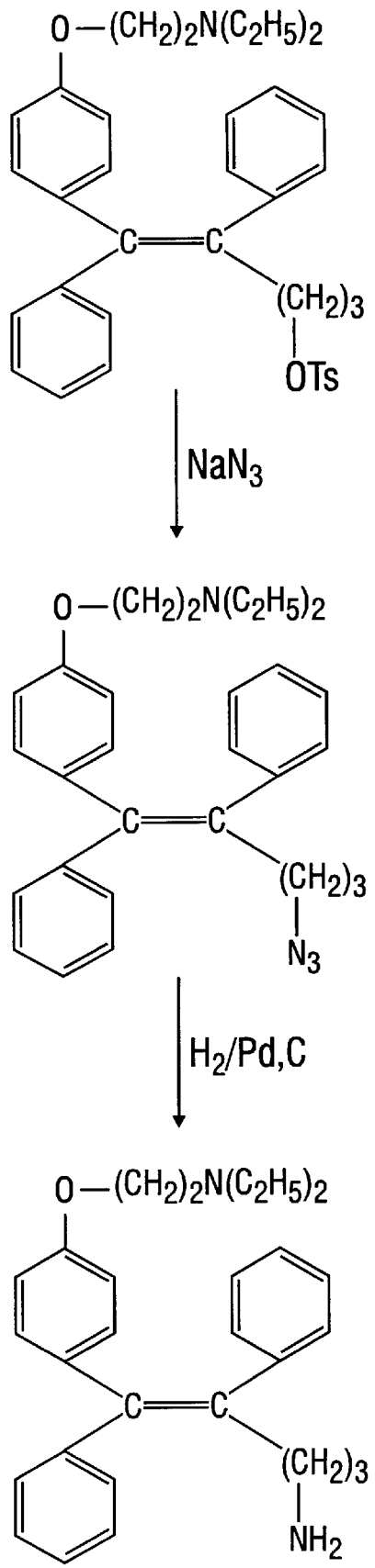
FIG. 20 Synthesis of amino tamoxifen analogs.

Following Standard procedures (Hama Cher et al. (1986), J. Nucl. Med., 27:235–238), the fluorination reaction was achieved easily to give the fluoromethyl analogue of tamoxifen in a 30–40% yield (60–70% mins, EOS). HPLC analysis of the transisomer is shown in FIG. 19. As can be seen, the fluoro compound was resolved from the unlabeled reaction and gave a high specific activity product in a reasonable yield. In this no-carrier-added synthesis, the specific activity was determined to be greater than 6 Ci/μmol with a radiochemical purity of 99%. An authentic non-radiolabeled fluoro analogue of tamoxifen was co-injected to confirm the identity of the $^{18}$F-labeled compound.

In Vivo Tissue Distribution

The biodistribution of the [$^{18}$F]fluoro analogue of tamoxifen in rats is shown in Table 11. The tumor-to-blood ratio of [$^{18}$F]-tracer in the 2 hr group was 3.5±0.27. This increased uptake can be blocked by pretreatment of diethylstilbestrol, which reduced this ratio to 2.4±0.10. Tumor uptake appears to be mediated through an estrogen receptor uptake process. From the a Scatchard analysis in the estrogen receptor assay, the 13762 tumor cell-induced tumors have estrogen receptor density (Bmax) of 7.5 fmol/mg of cytosol protein and a receptor binding affinity (Kd) of 33 nM. Protein concentrations were determined to be 400 μg/ml. The data indicate that 13762 mammary tumor-bearing rat is a suitable animal model for ER(+) studies.

TABLE 11

BIODISTRIBUTION OF [$^{18}$F]FLUOROMETHYL-N,N-DIETHYL-TAMOXIFEN IN MAMMARY TUMOR-BEARING RATS[1]
(% of Injected Dose Per Gram of Tissue Weight)

| Tissue | 30 min. | 2 h | 2 h (Blocking)[2] | 4 h |
|---|---|---|---|---|
| Blood | 0.169 ± 0.0240 | 0.114 ± 0.0148 | 0.102 ± 0.0097 | 0.069 ± 0.0091 |
| Lung | 3.817 ± 0.4202 | 3.498 ± 0.8205 | 2.084 ± 0.2384 | 1.314 ± 0.4525 |
| Liver | 6.360 ± 0.8438 | 6.930 ± 1.8194 | 7.242 ± 1.3283 | 6.496 ± 0.6342 |

TABLE 11-continued

BIODISTRIBUTION OF [$^{18}$F]FLUOROMETHYL-N,N-DIETHYL-
TAMOXIFEN IN MAMMARY TUMOR-BEARING RATS[1]
(% of Injected Dose Per Gram of Tissue Weight)

| Tissue | 30 min. | 2 h | 2 h (Blocking)[2] | 4 h |
|---|---|---|---|---|
| Kidney | 1.712 ± 0.2215 | 2.077 ± 0.4021 | 1.241 ± 0.1764 | 0.652 ± 0.0637 |
| Bone | 0.264 ± 0.0379 | 0.482 ± 0.0268 | 0.278 ± 0.0546 | 0.258 ± 0.1068 |
| Muscle | 0.183 ± 0.0369 | 0.234 ± 0.0617 | 0.131 ± 0.0090 | 0.093 ± 0.0093 |
| Uterus | 0.536 ± 0.0930 | 0.649 ± 0.0796 | 0.435 ± 0.0659 | 0.364 ± 0.0667 |
| Tumor | 0.256 ± 0.0266 | 0.405 ± 0.0787 | 0.244 ± 0.0173 | 0.284 ± 0.0179 |
| Tumor/Blood | 1.5 ± 0.19 | 3.5 ± 0.27 | 2.4 ± 0.10 | 4.2 ± 0.58 |
| Tumor/Muscle | 1.5 ± 0.39 | 1.8 ± 0.41 | 1.9 ± 0.20 | 3.1 ± 0.18 |

[1]Each rat received 10 µCi of $^{18}$F-FTX; data represents the mean of three rats per group per time point.
[2]Rats were pretreated with DES (1.2 mg) 1 h prior to giving $^{18}$F-tracer.

PET Imaging Studies

Figure 11A:
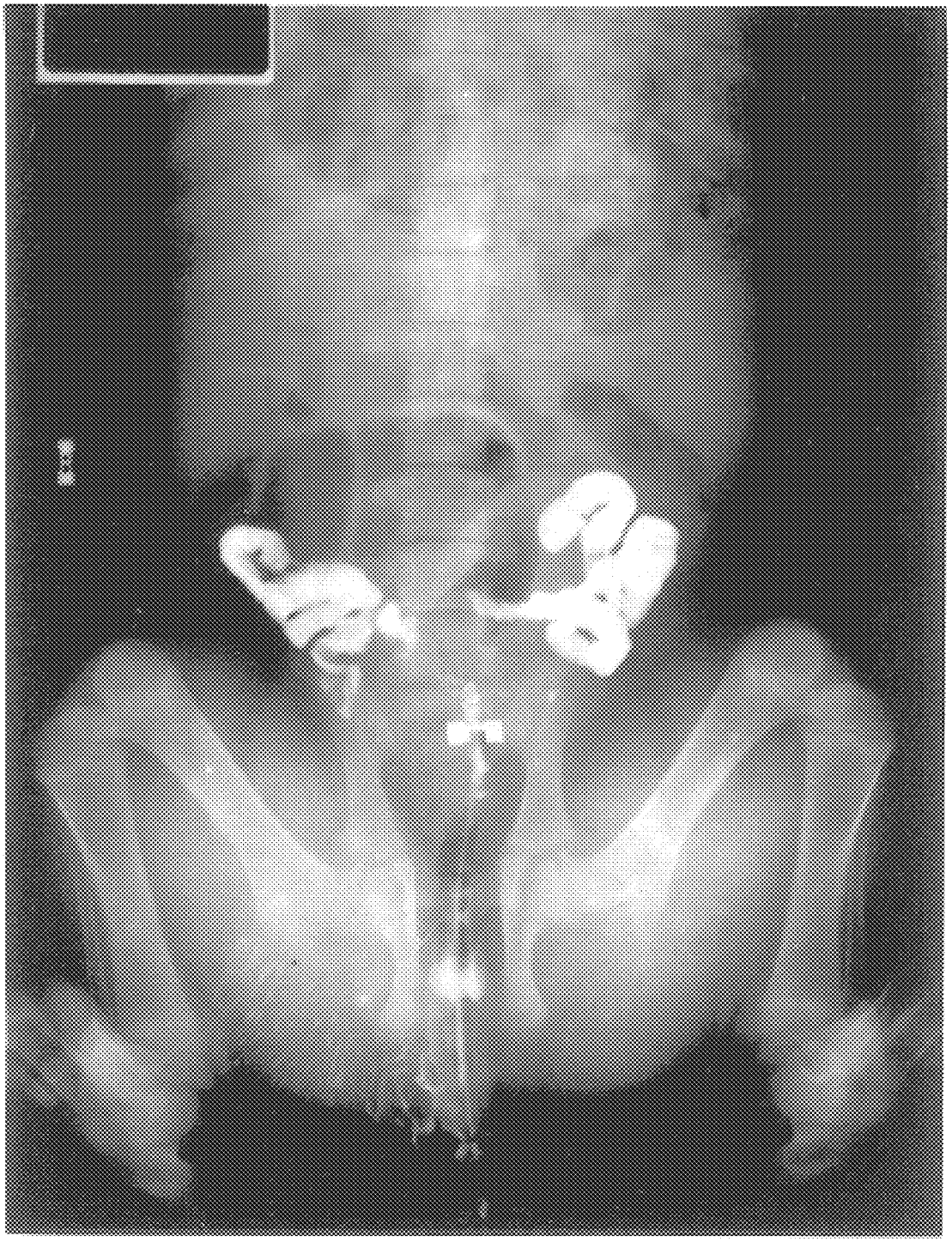
FIG. 11 Hysterosalpingography (11A–11B) of a pig. The opacified regions are the uterus and ovaries.
FIG. 11C shows the actual size of a pig uterus and ovaries.
Figure 11B:
Figure 11C:
Figure 12A:
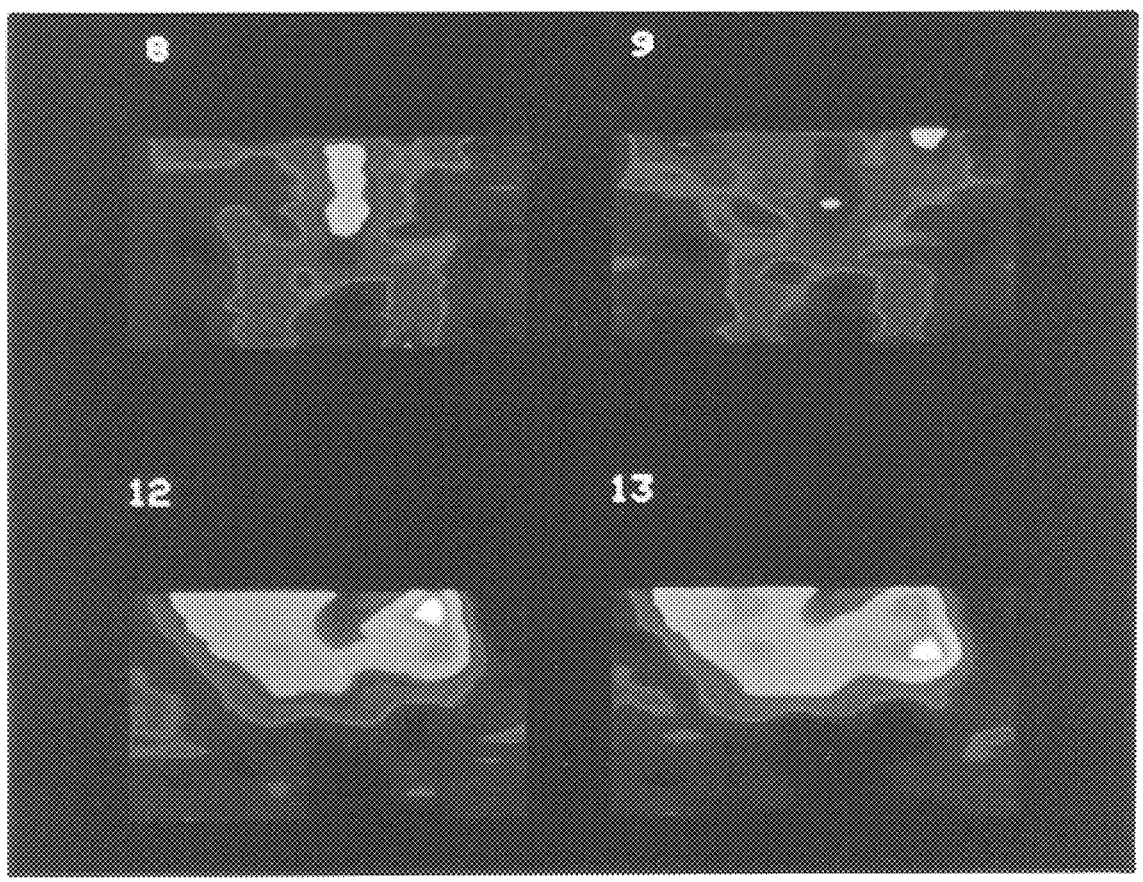
FIG. 12 PET image (A: coronal; B: sagittal) of the pelvic region of a pig receiving [$^{18}$F]FTX (10 mCi). The images correlate to hysterosalpingogram.
Figure 12B:
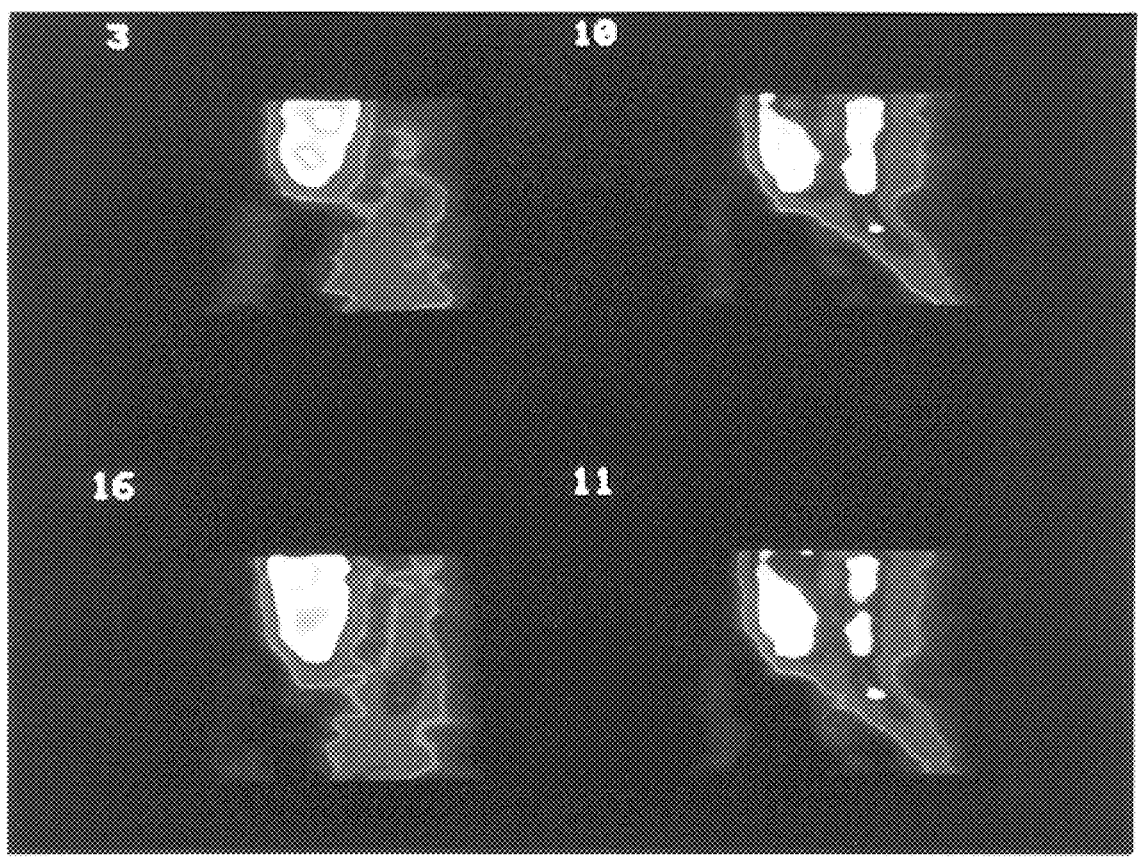
Figure 13:
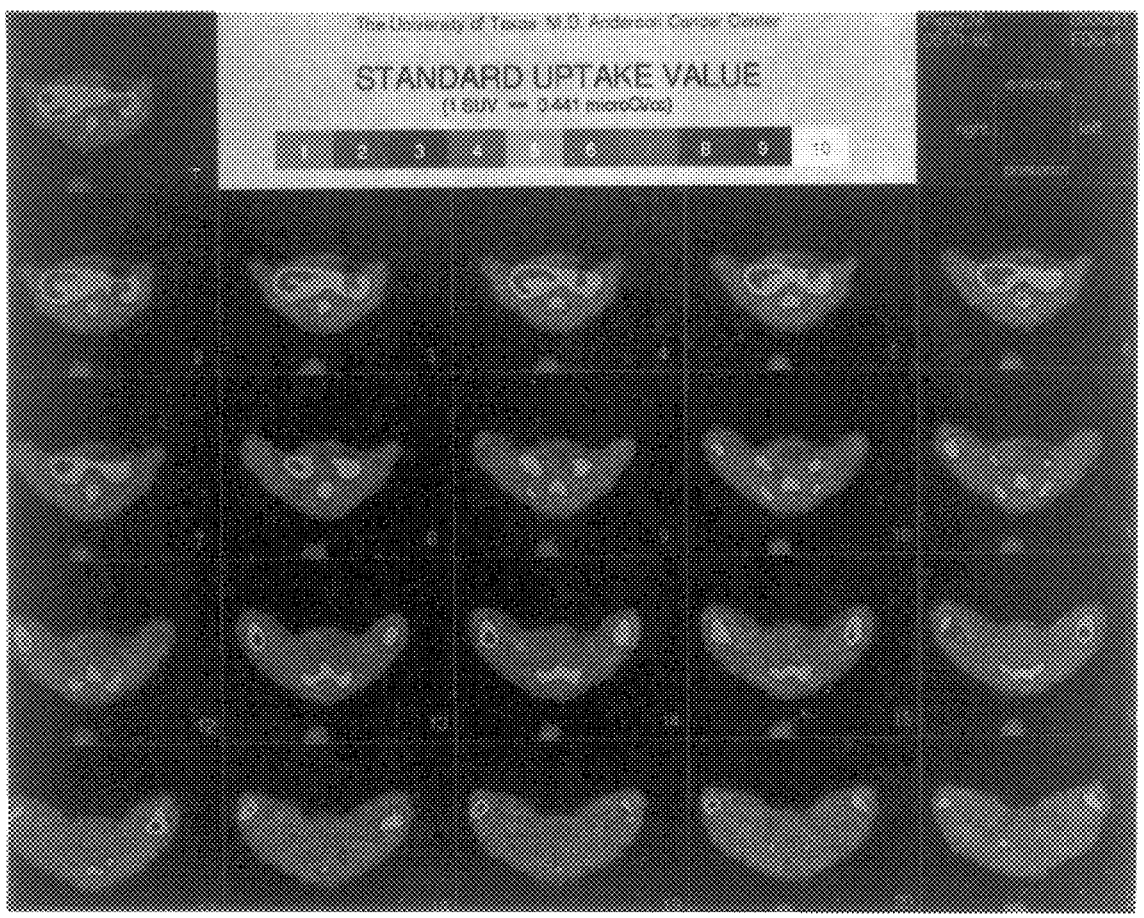
FIG. 13 PET image (transaxial) of the pelvic region of a pig receiving [$^{18}$F] fluoro analog of tamoxifen [$^{18}$F] (FTX (10 mCi i.v.)) 1 hour postinjection. The pig was positioned supine and scanned from cranial to caudal. Twenty-one slices per scan were collected. From slices 1–7, the image demonstrates increased uptake in the uterus ($10^5$ cell/rat).

The position of the uterus and ovaries in the pelvis of pigs is shown in FIGS. 11A–11C. The PET image correlated with the findings observed in the hysterosalpingogram. The coronal and sagittal views of a PET image of the pelvis of a pig 1 hr after administration of [$^{18}$F]FTX is shown in FIGS. 12A and 12B. The pig was scanned from a cranial to caudal direction. The transaxial image showed increased uptake in uterus (FIG. 13). This increased uptake could be blocked after pretreatment with DES (50 mg) (FIG. 14) followed by [$^{18}$F]FTX at 1 hour postinjection. This data suggests that the uptake of [$^{18}$F]FTX in the uterus and ovaries is mediated via an estrogen receptor.

Figure 16:
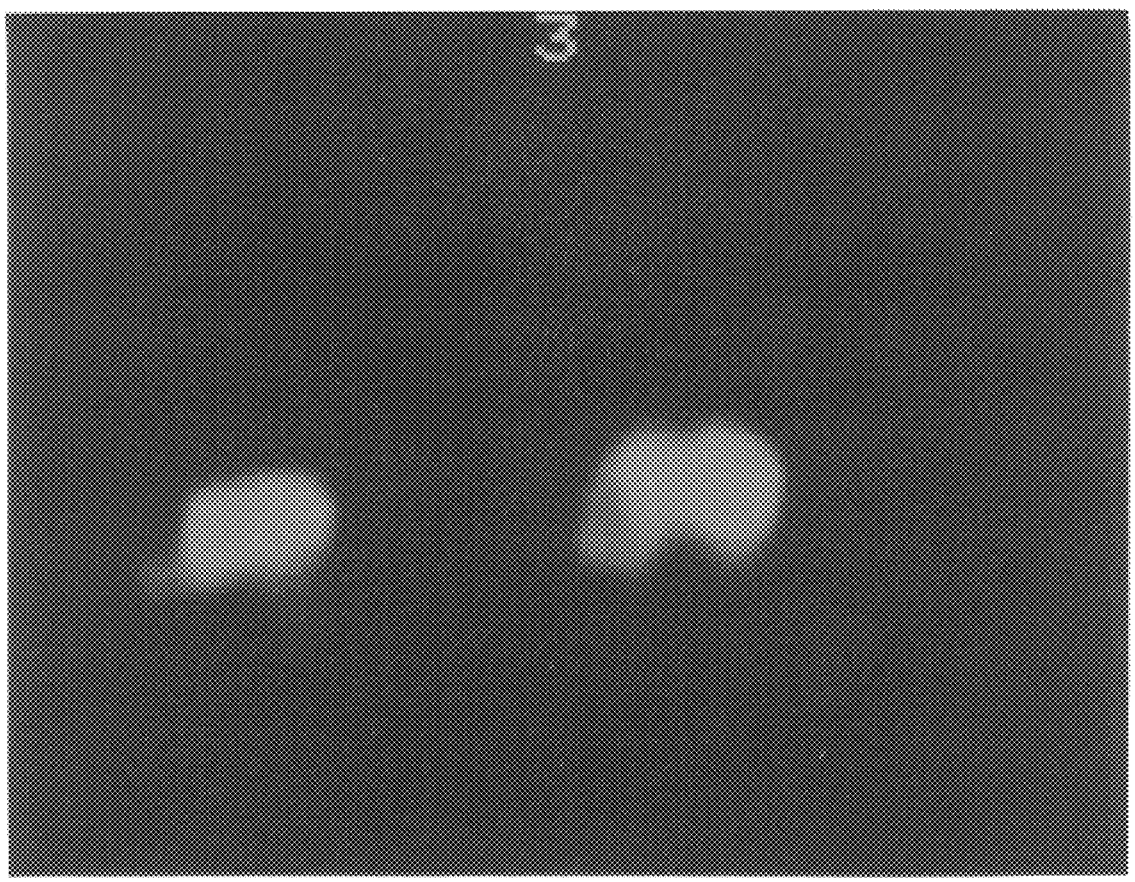
FIG. 16 PET image of mammary tumor-bearing rats demonstrates that a tumor can be visualized at 1 hour postinjection of [$^{18}$F] fluoro analog of tamoxifen (400 μCi, i.v.). The arrow indicates the site of the tumor.

PET imaging of 13762 mammary tumor-bearing rats indicate that the tumor can be visualized at one hour postinjection of [$^{18}$F]FTX (FIG. 16).

Figure 17:
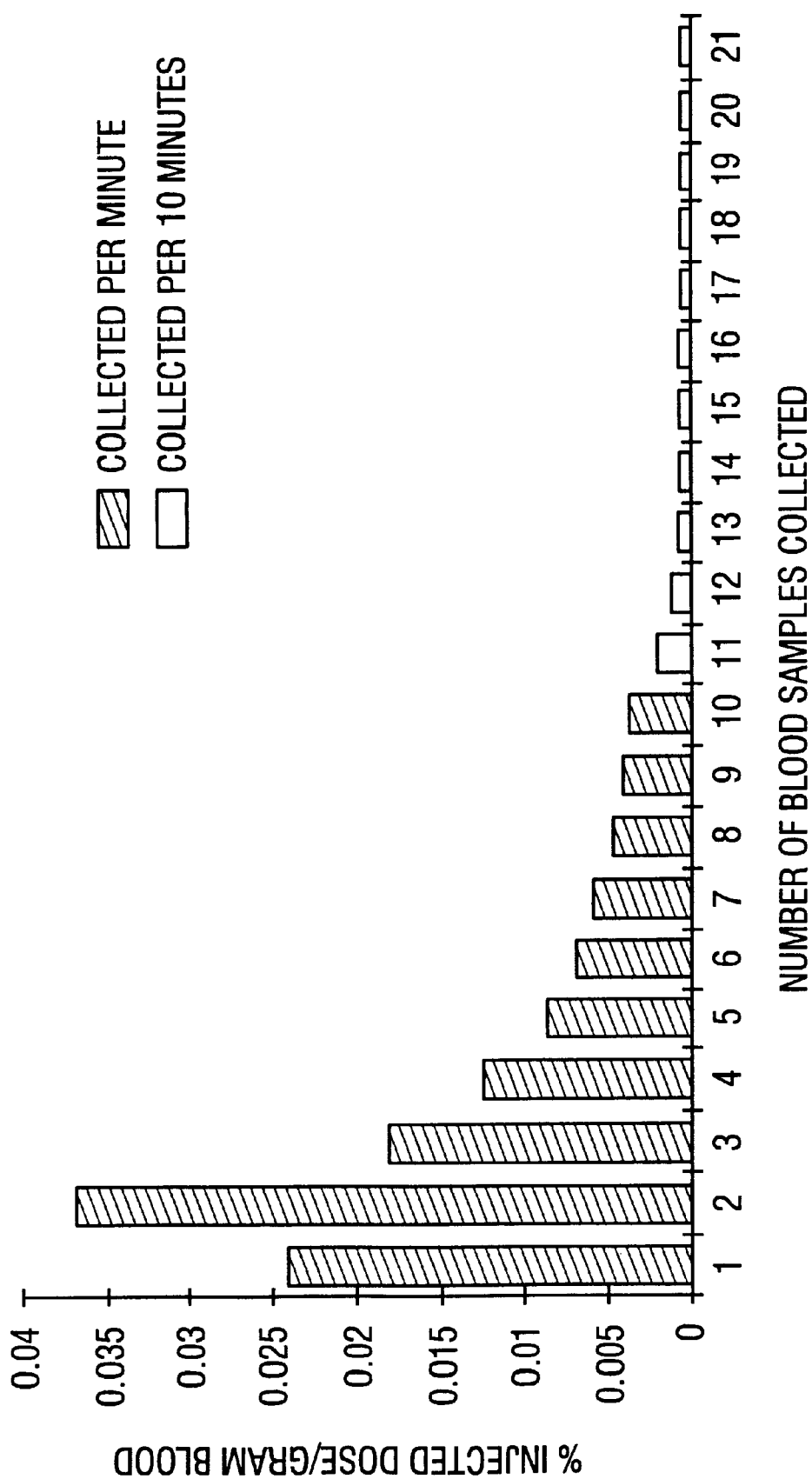
FIG. 17 Blood clearance profile after intravenous administration of [$^{18}$F]FTX (10 mCi) to pig.

A [$^{18}$F]FTX blood clearance profile of a female pig is shown in FIG. 17. The data demonstrates that [$^{18}$F]FTX is cleared from the blood stream within 10 minutes and the target organ binding is constant after 30 minutes to 2 hours post-administration of [$^{18}$F]FTX.

Animal Toxicity Studies

Toxicity studies showed that all doses tested of the F-TX were well tolerated, including 200 mg/kg. The fluoro analogue of tamoxifen also showed no acute or chronic toxicity during a one month follow-up period.

PET is able to demonstrate the uptake of [$^{18}$F] fluoromethyl-N,N-diethyltamoxifen in uterus and ovaries. The in vivo blocking studies with $^{18}$F-tamoxifen provided herein show that tamoxifen uptake in the uterus and ovaries can be blocked with DES. Thus, the fluoro analogue of tamoxifen has a potential use in diagnosing breast tumors as well as imaging tumors with functioning estrogen receptors (e.g. meningiomas) (Pollack et al. (1990) *Cancer Research*, 50:7134–7138).

EXAMPLE 21

Synthesis of Amino Tamoxifen Derivatives

The present example is provided to demonstrate the synthesis of the amino tamoxifen derivatives of the present invention.

Synthesis of Hydroxyethylmercaptomethyl-N,N-diethyltamoxifen

Cis or trans chloro analogue of tamoxifen (0.213 g, 0.476 mmol) dissolved in dimethylformamide (DMF, 25 ml) was added NaH (17 mg, 0.57 mmol) and mercaptoethanol (44.5 mg, 0.57 mmol). The reaction was heated at 80° C. for 2 h. DMF was then distilled and CHCl$_3$ (50 ml) was added. The mixture was washed with water (4×20 ml). The CHCl$_3$ layer was dried over MgSO$_4$, filtered and evaporated to dryness. The crude product was reconstituted in CHCl$_3$, loaded on a silica gel packed column and eluted with 10% triethylamine in ether:petroleum ether (1:1). The product was isolated, cis (200 mg, 86.2%) or trans (150 mg, 64.7%). M$^+$=489 (cis(, $^1$H-NMR of cis and trans products are attached. Anal. Cis (C$_{31}$H$_{39}$NO$_2$S: ½ H$_2$O) C,H,N,S. calc. C: 73.34, H: 8.14, N: 2.76, S: 6.30; Found,: 74.12, H.7.70, N: 2.72, S: 5.77.

Radiolabeling of Hydroxyethylmercapto Analogue of Tamoxifen

Hydroxyethylmercapto analogue of tamoxifen (1 mg) was dissolved in acetone (1 ml). $^{99m}$Tc-pyrophosphate (with SnCl$_2$) (140 µCi) was added and the reaction was reacted at room temperature for 10 min. Three TLC solvent systems were used to prove the product. These systems are acetone, saline and ether:petroleum ether:triethylamine (PET) (1:1:10%). All free $^{99m}$Tc will migrate to solvent front in these systems, however, $^{99m}$Tc-labeled the product will remain at origin. $^{99m}$Tc-pyrophosphate will migrate in saline system. The $^{99m}$Tc-labeled product isolated is ranging from 20–40% yield.

Synthesis of Thiomethyl-N,N-diethyltamoxifen

The cis or trans tosylmethyl analogue of tamoxifen (0.58 g, mmol) was added to a solution of potassium ethylxanthogenate (0.24 g, 1.5 mmol) in acetone (300 ml). The mixture was refluxed for 2 days. The precipitated potassium salt was filtered and the solvent was evaporated as described (Synthesis 1974, 425–426).

The crude xanthogenic ester was decomposed by stirring it for 4 h in the presence of ethylenediamine (30 ml). The crude mixture was then chromatographed on a silica gel-packed column eluted with 10% triethylamine in ether:petroleum ether (1:1) to yield 150 mg of cis or trans isomers (20%). The $^1$HNMR assignment is attached.

Preparation of Tamoxifen Azide (TX-N$_3$)

Into a suspension of NaN$_3$ (260 mg, 4 mmol) in 4 ml dry DMF was added 150 mg tamoxifen tosylate (TX-OTs) (0.25 mmol). The reaction mixture was stirred at 90° C. overnight. To terminate the reaction, the vxn mixture was poured into cold water and extracted with ethyl ether (3×50 ml). The organic layers were combined and washed with H$_2$O (2×50 ml). The ether layer was then dried over magnesium sulfate and evaporated. Further purification by flash chromatography (ether/petroleum ether/triethyl amine=5/5/1) yielded pure TX-N$_3$. Yield 50% IR: 2150 cm$^{-1}$ (Azide).

Preparation of Amino Tamoxifen (TX-NH$_2$)

100 mg TX-N$_3$ was dissolved in 10 ml ETAC. 5% on carbon was used as a catalyst. Hydrogenation reaction was conducted at room temperature for 4 hrs. After filtration to remove Pd/C, ExAc was evaporated to give amino tamoxifen. Yield 80%. NMR, and mass are attached as Figures.

These amino tamoxifen derivatives may also be advantageously employed in the therapy of ER$^+$ tumors, in PET imaging of estrogen receptors in vitro and estrogen receptor rich tissues in vivo with high tissue specificity, and also as targeting agents conjugated to, for example, microcapsules, to visualize estrogen rich tissues. The conjugated forms of these derivatives may also provide for sustained tamoxifen release agents in vivo.

EXAMPLE 22

In Vivo Tissue Distribution of [$^{18}$F]-FTX in Rats and Toxicity Studies of F-FTX in Mice The [$^{18}$F] fluoride was prepare as described herein. Other methods for preparing [$^{18}$F] fluoride known by those of skill in the art may also be employed with equal efficacy in conjunction with the specific teachings provided herein.

In Vivo Tissue Distribution

The inventors first determined the in vivo tissue distribution of [$^{18}$F-FTX] in rats. Specifically, four groups of female Sprague-Dawley rats (N=4/group, 200–250 gm; obtained from Harlan Inc., Indianapolis, Ind.) were anesthetized with ketamine (10–15 mg/rat). (trans)[$^{18}$F]Fluoromethyl-N,N-diethyltamoxifen was reconstituted in 0.05 M citrate buffer, and 5 μCi of this tracer was intravenously injected into rats primed with estradiol (60 μg, s.c., 3 days). To ascertain whether the $^{18}$F-tracer uptake occurred via receptors, one group of rats was given $^{18}$F-tracer with estradiol (30 μg/rat) for 30 minutes, followed by $^{18}$F-tracer (5 μCi). The amount of estradiol given concurrently with the tracer was expected to occupy estrogen receptors and to displace radioactivity from the rat uteri and ovaries. The tissue distribution was studied at 2 hour and 4 hour intervals.

In Vivo Tissue Distribution

The biodistribution of the [$^{18}$F]fluoro analogue of tamoxifen in rats is shown in Table 11. the uterus to blood ratio of [$^{18}$F]-tracer in the 2 hour group was 13.5±2.97 with estradiol priming, respectively. This increased uptake in estradiol-priming group can be blocked by pretreatment of estradiol, which yielded a ratio of 6.3±1.62. The data suggest that the uterus uptake is mediated through an estrogen receptor uptake process. The bone uptake was increased from 0.65% to 0.80% of the injected dose at 4 hour postinjection. This increased uptake could be caused by uptake of $^{18}$F tracer into bone marrow.

TABLE 12

INJECTED DOSE/GRAM OF TISSUE WEIGHT (RATS PRIMED WITH 60 μg OF ESTRADIOL FOR 3 DAYS (N = 4/GROUP))

|              | 2 h            | 4 h            | 2 h (blocked)[1] | 2 h[2]         |
|--------------|----------------|----------------|------------------|----------------|
| Blood        | 0.033 ± 0.0059 | 0.045 ± 0.0003* | 0.048 ± 0.0066  | 0.033 ± 0.0109 |
| Liver        | 4.540 ± 0.5053 | 4.205 ± 0.4397 | 4.451 ± 1.1559   | 3.849 ± 0.4069 |
| Kidney       | 0.742 ± 0.0756 | 0.796 ± 0.3000 | 0.742 ± 0.1451   | 0.530 ± 0.0752 |
| Uterus       | 0.426 ± 0.0177 | 0.400 ± 0.0312 | 0.297 ± 0.0356*  | 0.248 ± 0.0535* |
| Muscle       | 0.151 ± 0.0203 | 0.183 ± 0.0015 | 0.145 ± 0.0446   | 0.109 ± 0.0218 |
| Bone         | 0.653 ± 0.1348 | 0.802 ± 0.0556 | 0.576 ± 0.1268   | 0.644 ± 0.0656 |
| Intestine    | 0.917 ± 0.3058 | 1.101 ± 0.5986 | 0.742 ± 0.0458   | 0.504 ± 0.1784 |
| Uterus/Blood | 13.5 ± 2.97    | 9.1 ± 1.34     | 6.3 ± 1.62*      | 6.6 ± 0.29*    |
| Uterus/Muscle | 2.9 ± 0.43    | 2.2 ± 0.16     | 2.2 ± 0.62       | 2.5 ± 0.37     |

[1]Pretreatment of estradiol (30 μg) 30 minutes, followed by $^{18}$F-tracer (5 μCi). An asterisk * indicates significantly different (p < 0.005) from the 2 h group value.
[2]Not primed with estradiol.

In Vivo Biodistribution of $^{18}$F-FTX in Mammary Tumor-Bearing Rats—Estrogen Primed The biodistribution of $^{18}$F-tracer in tumor bearing rats is shown in Table 12. The increased uptake in the tumor and uterus can be blocked by pretreatment with diethylstilbestrol (DES). The data suggest that uptake of tracer in the tumor and uterus is mediated by estrogen receptors and is not due to in vivo defluoridation based on free fluoride uptake in the bladder.

Pet Studies

The PET image correlated with the findings on the hysterosalpingogram. The pig was scanned in a cranial to caudal direction. The studies showed an increased uptake in uterus and ovaries. This increased uptake could be blocked after pretreatment with diethylstilbestrol (DES, 10 mg) followed by $^{18}$F-tracer at 1 hr postinjection. The PET data indicate that the uptake of $^{18}$F-tracer in the uterus and ovaries is mediated via an estrogen receptor.

Animal Toxicity Studies

Animal toxicity studies are summarized in Table 13. In BALB/c Female rats, the dosage tested for unlabeled fluoro analogue of tamoxifen was from 20 mg/kg to 200 mg/kg as a single-dose (i.v.). All rats tolerated various doses of the drugs without toxicity on longer follow-up periods. Of all of the halogenated tamoxifen F, I, Fr and Cl, only the trans-form of Iodotamoxifen had toxicity. The lethal effect of trans ITX was observed in 3 out of 4 mice studied at 20 mg/kg dose.

The fluoro analogue of tamoxifen which will be used in this study showed no acute or chronic toxicity in mice. Dosages up to 200 mg/kg are well tolerated by mice.

TABLE 13

HALOGEN-TAMOXIFEN ANALOGUES:
IMMEDIATE TOXICITY FOLLOWING I.V. INJECTION
Recipient mice: BALB/c, female, approx. 20 g weight
Inoculum volume of 0.1 ml, in 5% ethanol (vehicle alone had no effect)

| Analogue | Maximum dose tolerated |
|---|---|
| cis-CITX | 50 mg/kg (12.5 mg/ml) |
| trans-CITX | 20 mg/kg (5 mg/ml) |
| cis-ITX | 50 mg/kg (12.5 mg/ml) |
| trans-ITX | 8 mg/kg (2 mg/ml) |
|  | (3/4 mice died at 20 mg/kgl) |
| cis-$^{18}$F-FTX | 50 mg/kg (12.5 mg/ml) |
| trans$^{18}$F-FTX | 200 mg/kg (50 mg/ml) |
| cis-BTX | 50 mg/kg (12.5 mg/ml) |
| trans-BTX | 50 mg/kg (12.5 mg/ml) |

N.B. for cis- and trans-BTX, 1 mouse was injected with a higher dose, 1.5 ml of the 12.5 mg/ml dilution, and the mice survived.
The lethal effects of trans-ITX were immediate; mice that survived the initial injection showed no long-term effect. All other isomers tested showed no toxicity in these studies at all dose levels evaluated in the above table.
In the second set of injections (trans-$^{18}$F-FTX, higher concentrations), the vehicle was 15% ethanol, which was well tolerated.

$^{18}$F-fluorodeoxyglucose ($10^{-7}$ or $10^{-6}$ mg total dose) is routinely used at M. D. Anderson Cancer Center at doses which are not sufficiently concentrated to evoke a histamine response. These doses are considered tolerable for radiodiagnostic tests and no reports of toxicity are found in the literature.

In large animal studies, the $^{18}$F-FTX blood clearance profile is shown in FIG. 17. The data shows that $^{18}$F-FTX is cleared from blood stream with 10 min. The target organ binding is constant after 30 minutes to 2 hours post-administration of $^{18}$-FTX. As illustrated in FIG. 17, the first ten blood samples was collected by 1 min interval. From 10 to 21, the blood samples were collected at 10 min interval.

PROPHETIC EXAMPLE 23

Proposed use of Radiolabeled Tamoxifen Derivatives for Radiodiagnosis in Humans

The present prophetic example is provided to demonstrate a proposed method whereby the tamoxifen derivatives of the invention may be used diagnostically in humans. Most specifically, the present example will outline a proposed use of ($^{18}$F-FTX) derivative for use in humans as an exemplary tamoxifen derivative. However, other of the tamoxifen derivatives described herein may be used with equal efficacy for the present methods.

Dose Estimates for Human

From the data obtained for in vivo tissue distribution of $^{18}$F-tracer in animals (Tables 11 and 12), dosimetry was calculated for humans as shown below.

| Target Organ | Total Dose mGy/MBq | rad/mCi |
|---|---|---|
| small intestine | 0.0720 | 0.2660 |
| kidney | 0.0360 | 0.1360 |
| liver | 0.1570 | 0.5810 |
| uterus | 0.0149 | 0.0551 |

In a phase I study, $^{18}$F-FTX will be evaluated at different dose levels starting with 2 mCi which will contain 067 mg of tamoxifen. Three patients will be imaged at each dose level, and dose escalation will be 100% in first two dose levels; subsequently 50% dose escalation will be done.

The stable compound to be used as an imaging agent in this proposal (0.6 to 6 mg) is considerably less than doses tested (20–200mg/kg) in regard to the animal toxicity results described in Example 22 and shown to have no toxicity in mice. For comparison, clinical trials of tamoxifen as a chemotherapeutic agent for breast cancer patients use 20 mg b.i.d.

Patient Eligibility

The following criteria will be used in selecting eligible patients for the present study.
1. Female patients ±21 years of age with a biopsy proven primary and/or metastatic breast cancer which is estrogen receptor-positive (±10 fmol/mg protein).
2. Disease evaluable by conventional radiological studies.
3. Adequate hepatic function with a bilirubin of 1.5 mg %, and should have adequate renal function defined as a serum creatinine ±1.5 mg %.
4. Adequate bone marrow function defined as absolute granulocyte count 1500 mm$^3$, and platelet count >100,000 mm$^3$.
5. Not on any additive or ablative endocrine therapy.

Exclusion criteria

Patients with childbearing potential must not be pregnant at time of this study.

Treatment Plan

Three eligible patients will be entered in this study at each dose level. The starting dose will be 2 mCi.

To assure sterility, each batch of product will be tested using culture vials with aerobic and anaerobic materials (NR6 and NR7) Becton Dickinson Diagnostic Instrument Systems, Towson, Md.). Drug solution (0.3 ml) will be incubated with Bactec culture vials for 7 days at 37° C. Sterility will be assayed by visualizing the cloudiness of the solution.

To test for pyrogens, a LAL manufacture kit (Whittaker Bioproduct, Walkerville, Md.) will be used. The drug solution (0.26 ml) will be incubated for 1 hour at 37° C. in a vial using a LAL kit. Two additional standard samples (positive 0.125 Eµ/ml and negative) will be used as control. The positive sample forms a gel and the negative sample is clear. The sensitivity for the LAL test is 0.125 Eµ/ml. Six samples will be tested. All samples should be sterile and pyrogen-free.

High pressure liquid chromatographic (HPLC) analysis of each batch will be performed. A C-18 reverse-phase Radial-Pak column (8×100 mm) will be used. The HPLC is equipped with both an ultra-violet detector and a radioactive-flow detector. The radioactive product should have a retention time of 6.7 min. The radiochemical purity should be greater than 96% and the specific activity should be greater than 6 Ci/µmol.

Dosage escalation shall follow the schema below:

| Group | Pt | Dose of $^{18}$F-FTX | Stable Fluorotamoxifen |
|---|---|---|---|
| 1 | 3 | 2 mCi | 0.67 mg |
| 2 | 3 | 4 mCi | 1.33 mg |
| 3 | 3 | 8 mCi | 2.67 mg |
| 4 | 3 | 12 mCi | 4.00 mg |
| 5 | 3 | 18 mCi | 6.00 mg |

If the preceding dose level has not been associated with toxicity in any patient, dosage escalation will proceed.

Dose escalation will not be done in the same patient. Each patient will have only one study at the given dose level.

Imaging Studies

Eligible patients will receive $^{18}$F-FTX in 4 ml of solution through a heparin-lock. After the injection, the heparin lock will be flushed with 5–10 ml of the saline.

Prior to injection of $^{18}$F-FTX, an attenuation scan (20–30 min) will be done to measure body attenuation for gamma radiation. After injection, patients will be imaged continuously in 10 minute data collection intervals for 90 minutes. The commercially available PET camera used for imaging is a POSICAM 6.5 available in the Department of Nuclear Medicine at M. D. Anderson Cancer Center in Houston, Tex. Imagine will be taken at the known sites of metastatic disease and any other areas of abnormality. The image will be reconstructed and displayed in standard uptake values (SUV) which measures the ratio of tissue tamoxifen uptake to that of the whole body uptake (normalizes for body weight and injected dose). This information will be used to calculate whether uptake in the tumor correlates with the degree of estrogen receptor positivity.

All patients will be fasting for 4 hr prior to PET scanning and studied as an outpatient.

After injection of the $^{18}$F-FTX, 1½ to 2 ml of venous blood will be drawn every 15 minutes for 90 minutes for $^{18}$F-FTX clearance. The blood tamoxifen clearance will be compared to the tumor uptake. This will establish vascularity of the tumor as well as estrogen receptor sites.

Pretreatment Evaluation

A complete history and physical examination, to include performance status, the size of the primary tumor if in the breast, and size of the regional nodes if involved with the tumor, will be documented. Laboratory studies will include CBC, differential, platelet count, SMA and appropriate radiological or radioisotopic studies to document the extent of metastatic disease.

Estrogen receptor and progesterone receptor assays will be done on the tumor in the breast or on the metastatic tumor. The tumor should be estrogen receptor-positive. Pharmacokinetics studies will include 6 blood samples of 1½ to 2 ml of blood drawn for the determination of the clearance of $^{18}$F-FTX from the blood. These will be drawn through a heparin-lock.

TABLE 14

EVALUATIONS BEFORE AND DURING THERAPY

| | PRE-STUDY | DURING STUDY |
|---|---|---|
| History | X | |
| Physical | X | |
| Tumor Measurements | X | |
| CBC | X | |
| Differential | X | |
| Platelet Count | X | |
| SMA-100 | X | |
| Pregnancy test* | X | |
| X-rays* | X | |
| Estrogen & Progesterone Receptor | X | |
| $^{18}$F-FTX Pharmacokinetics Studies | | X |
| Pet Imaging Studies | | X |

Criteria for Evaluation of Imaging Studies and Toxicities

Tumor sites will be documented prior to entering the study and no antitumor responses are expected with this study. Comparisons of conventional radiographs and radio-isotopic studies will provide an objective method for determination of what dose of $^{18}$F-FTX is appropriate for imaging. Toxicities will be documented according to our criteria as shown in Table 15, and will be graded according to a standard human grading system. Life-threatening toxicities should be reported to the study chairman.

Statistical Consideration

Major objective of this study is to determine whether $^{18}$F-FTX can identify the site of primary and metastases in patients with estrogen receptor positive breast cancer. All patients entered on the study will be evaluable for toxicity.

TABLE 15

TOXICITY CRITERIA

| ALLERGY | Grade 1 | Grade 2 | Grade 3 | Grade 4 |
|---|---|---|---|---|
| ALLERGY | | | | |
| Acute Allergic Reaction | Transient rash, Drug fever <38 C./100.4 F. | Urticaria, Drug fever >38 C./100.4 F., mild bronchospasm | Serum sickness, bronchospasm, req parenteral meds | Anaphylaxis |
| Fever with Drug | 37.1–38.0 C. 98.7–100.4 F. | 38.1–40.0 C. 100.5–104.0 F. | >40.0 C.>104.0 F. for less than 24 h. | >40.0 C. (104.0 F.) for more than 24 hr. or fever accp. by hypotension |
| CARDIOVASCULAR | | | | |
| Cardiac Symp. | Mild or transient | Symptoms on exertion | Symptoms at rest, persistent | Severe symptoms, non response to RX |
| Cardiac Funct. | Asymptomatic, decline of resting ejection fract. by less than 20% of baseline value or EF 60–64% | Asymptomatic, decline of resting ejection fraction by more than 20% of baseline value or EF 50–59% | Mild CHF, responsive to therapy or EF 40–49% | Severe or refractory CHF or EF <40% |
| Cardiac Biopsy | 0.5 | 1.0 | 1.5 | >1.5 |
| Dysrhythmia | Asymptomatic, transient, requiring no therapy. Resting sinus tach, PAC's, <1 PVC hr abn, 1st deg AV block | Recurrent or persistent no therapy required. Sustained atrial arrhyth, 1–9 PVC/hr. Mobitz type I incompl or rate-related bundle branch block | Requires treatment 10–29 PVC/hr, multifox PVCs, couplets, 3–5 consec PVC and salvos Mobitz type II, Bundle branch of bifascic block requires treatment | Requires monitoring; or hypotension, or ventricular tachycardia, or fibrillation. >30 PVC 6 consed PVC, 3rd deg AV block |
| Hypertension | Asymptomatic, transient inc. by >20 mm Hg(d) or to >150/100 if prev. WNL. No RX required | Recurrent or persist. increase by >20 mm Hg (D) or to >150/100 if prev. WNL. No RX rqd. | Required RX. | Hypertensive crisis |
| Hypotension | Changes req. no RX (10–20% dec systol) | Req. fluid replacement or other RX, no hosp. (21–30% dec systol) | Req. RX & hospitalization, resolves in 48 hr. after stopping agent (31–40% dec systol) | Req. rx & hospitalization for .48 hrs after stopping agent (>40% dec systol, not resps to pressors) |
| Ischemia | Non-specific ST or T-wave flattening | Asymptomatic, ST and T wave changes suggesting ischemia | Angina w/o evidence of infarction | Acute myocardial infarction |
| Pericardial | Asymptomatic effusion, no intervention reqd. | Pericarditis (rub, check pain, ECG changes) | Symptomatic effusion; drainage required | Tamponade, drainage urgently required |
| Periph Capillary | Min ankle pitting | Ankle pitting | Periph edema, wt | Anasarca, sev |

TABLE 15-continued

TOXICITY CRITERIA

| ALLERGY | Grade 1 | Grade 2 | Grade 3 | Grade 4 |
|---|---|---|---|---|
| Leakage Syndr | edema | edema & wt gain <10 lbs | gain >9.9 lbs, pleural eff. w/no pul fx deficit | pleural effusion w/pul fx deficit, ascites |
| CNS | | | | |
| Cerebellar | Slight incoordination dysdiadokinesis | Intention tremor, dysmetria, slurred speech, nystagmus | Locomotor ataxia | Cerebellar necrosis |
| Constipation | Mild | Moderate | Severe | Ileus >96 hrs. |
| Cortical | Mild somnolence, agitation, or confusion | Mod somnolence agitation or confusion | Sev. somnolence, agitation, confusion, disorientation, hallucin | Coma, seizures toxic psycosis |
| Headache | Mild | Moderate or severe but transient | Unrelenting and severe | — |
| Mood | Mild anxiety or depression | Mod anxiety or depression | Severe anxiety or depression | Suicidal ideation |
| Motor | Subj. weakness, no obj. findings | Mild obj. weakness w/o sig. impairment or funct. | Obj. weakness with impairment of funct. | Paralysis |
| Ototoxicity | Asympt. hearing loss on audiometry only, mild or transient tinnitus | Mod tinnitus, interferes with hearing | Hearing loss interferon w/function, correctable with hearing aid | Deafness, not correctable |
| Sensory | Mild paresthesia, loss of DTR's | Mild or mod obj. sensory loss, mod paresthesia | Severe obj. sensory loss or paresthesis that interfere with function | — |
| Vision Abnormality | — | — | Symptomatic subtotal loss of vision | Blind |
| COAGULATION | | | | |
| Fibrinogen | 0.99–0.75 × N | 0.74–0.50 × N | 0.49–0.25 × N | </=0.24 × N |
| Partial Thrombo-plastin Time | 1.01–1.66 × N | 1.67–2.33 × N | 2.34–3.00 × N | >3.00 × N |
| Prothrombin Time | 1.01–1.25 × N | 1.26–1.50 × N | 1.51–2.00 × N | >2.00 × N |
| DERMATOLOGIC | | | | |
| Alopecia | Mild hair loss | Pronounced or total hair loss | — | — |
| Cheilitis | Chapping | fissures | Bleeding | Necrosis |
| Conjuctivitis | Mild | Moderate | Severe | — |
| Hand Foot Syndrome | Redness of palms of hands and soles of feet | Pain with redness and swelling of hands and feet | Despuamation of skin with pain, redness and/or swelling, nails fall off | |
| Skin Reaction | Scattered macular or papular eruption or erythema that is asympt, pruritis alone, dry skin | Scattered macular or papular eruption or erythremia with pruritus or other assoc. symptoms | Generalize sympt. macular, papular, or vesicular eruption | Exfoliative dermatitis or ulcerating dermatitis |
| GASTROINTESTINAL | | | | |
| Anorexia | Able to eat reasonable intake | Intake sig. decreased but can eat | No sig. intake | — |
| Diarrhea | Increase of 2–3 stools/day over pre-Rx | Increase of 4–6 stools/day, or noct. stools or moderate cramping | Increase of 7–9 stools/day, or incontinence or severe cramping | Increase of >/=10 stools/day or grossly bloody diarrhea, or need for parenteral support |
| Dysgeusia | Able to eat reasonable | Intake sig. decreased but can eat | No sig. intake | — |
| Nausea | Ableto eat reasonable intake | Instake sig. decreased but can eat | No sig. intake | — |
| Stomatitis | painless ulcers, erythema, or mild soreness | Painful erythema edema or ulcer, can eat | Painful erythema or ulcers cannot eat | Req. parenteral support |

TABLE 15-continued

TOXICITY CRITERIA

| ALLERGY | Grade 1 | Grade 2 | Grade 3 | Grade 4 |
|---|---|---|---|---|
| Vomiting | 1 episode in 24 hrs | 2–5 episodes in 24 hrs | 6–10 episodes in 24 hrs | >10 episodes in 24 hrs or req. parental supp. |
| Xerostoma | Transient | Persistent | — | — |
| GENERAL | | | | |
| Arthralgia | Mild | Moderate | Severe | — |
| Bone Pain | Mild | Moderate | Severe | — |
| Chills | Mild | Moderate | — | — |
| Fatigue | Zubrods 1 | Zubrods 2 | Zubrods 3 | Zubrods 4 |
| Local | Pain | Pain and swelling with inflammation or phlebitis | Ulceration | Plastic surgery indicated |
| Myalgia | Mild | Moderate | Severe | — |
| Weight Loss | 5.0–9.9% | 10.0–19.9% | >/=20% | — |
| HEMATOLOGIC | | | | |
| Anemia | 10.0 to norm. | 8.0–9.9 | 6.5–7.9 | <6.5 |
| Granulocytopenia | 1.5–1.9 | 1.0–1.4 | 0.5–0.9 | <0.5 |
| Hemorrhage | Petechiae, min blood loss, no trans req. | Blood loss req. 1–2 U trans | Blood loss req. 3–4 U trans | Blood loss req. >4 U trans |
| Leukopenia | 3.0–3.9 | 2.0–2.9 | 1.0–1.9 | <1.0 |
| Lymphocytopenia | 1.5–1.9 | 1.0–1.4 | 0.5–0.9 | <0.5 |
| Thrombocytopenia | 75–00 | 50–74 | 25–49 | <25 |
| HEPATIC | | | | |
| Alk Phos Increase | </=2.5 × N | 2.6–5.0 × N | 5.1–20.0 × N | >20.0 × N |
| Bili Increase | — | <1.5 × N | 1.5–3.0 × N | >3.0 × N |
| Hepatic Symptoms | — | — | Precoma | Hepatic coma |
| Transaminase increase | </=2.5 × N | 2.6–5.0 × N | 5.1–10 × N 5.1–20.0 × N | >10 × N >20.0 × N |
| INFECTION | | | | |
| infection | FUO, or mild infection | Moderate infection | Severe organ infection | Life-threatening or Disseminated, multilobular infection |
| METABOLIC | | | | |
| Amylase | <1.5 × N | 1.5–2.0 × N | 2.1–5.0 × N | >5.1 × N |
| Hyperglycemia | 116–160 | 161–250 | 251–500 | >500 OR ketoacidosis |
| Hypercalcemia hypertri- | 8.4–7.8 | 7.7–7.0 | 6.9–6.1 | </=6.0 |
| Glyceridemia | 200–400 | 401–600 | 601–800 | >800 |
| Hypoglycemia | 55–64 | 40–54 | 30–39 | <30 |
| Hypomagnesemia | 1.4–1.2 | 1.1–0.9 | 0.8–0.6 | </=0.5 |
| PULMONARY | | | | |
| Pul Function Abnormality | FVC 70–80% pred, FEVI or DLCO 60–80% pred, 15–25% dec from abn baseline | FVC 50–69% pred, FEVI or DLCO 40–59% pred, 26–50% dec from abn baseline | FVC <50% pred, FEVI or DLCO <40% pred, >50% dec from abn baseline | Unable to perform test due to resp distress |
| Respiratory Symptoms | Mild or transient | Dyspnea on significant exertion | Dyspnea at normal level of activity | Dyspnea at rest |
| RENAL | | | | |
| Bun Increase | | | | |
| Creat. Increase | <1.5 × N | 1.5–3.0 × N | 3.1–6.0 × N | >6.0 × N |
| Dysuria | Mild | Moderate | Severe | Unacceptable |
| Hematuria | 6–10 RBC/HPF | 11–50 RBC/HPF | Gross, >50 RBC/HPF | Clots, obstructive |
| Proteinurea | 1+, <0.3 g %, <3 g/L | 2–3+, 0.3–1.0 g %, 3–10 g/L | 4+, >1.0 g %, >10 g/L | Nephrotic syndrome |

PROPHETIC EXAMPLE 24

Proposed Uses of Amino Tamoxifen Derivatives for Imaging of Estrogen-Receptor Rich Tissues The present prophetic example is provided to describe a proposed method for using the amino tamoxifen derivatives described herein. It is anticipated that the amino derivatives will have equal, if not superior efficacy in the image of tissues and tumors rich in estrogen receptor, to those fluoro, iodo, bromo and chloro tamoxifen derivatives already described herein.

Synthesis of Amino Tamoxifen

Amino tamoxifen was prepared according to the protocol outlined in Example 21.

Radiolabeling of Amino Tamoxifen

An amino analogue of tamoxifen was radiolabeled with $^{11}CH_3I$ (t½=20 min.). Briefly, the amino group is protected with benzylchloroformate and reacted with $^{11}CH_3I$ (from $^{11}CO_2$+HI+Liaeh4). The radiochemical yield was 80%.

Radiodiagnostic Use of Amino Tamoxifen

The amino analogue of tamoxifen may be conjugated to radiopaque materials (e.g. iopanoic acid, diatrizoic acid). Such a conjugated product would be useful for the detection of ER(+) tumors with CT. The scheme for preparing the amino analog of tamoxifen and radiopaque material conjugates is outlined in Table 16.

EXAMPLE 25

In Vivo Human Tumor Inhibition

In vivo Human Tumor Inhibition

In vivo tumor inhibition with tamoxifen derivatives ten patents have been imaged with ER+ breast tumors using $^{18}$F-labeled tamoxifen ligand (2–12 mCi, iv) by positron emission tomography (PET). The transaxial view showed that both primary and metastatic breast tumors could be diagnosed by $^{18}$F-labeled tamoxifen ligand. This example describes a ligand for imaging ER (+) breast tumors by positron emission tomography (PET) or single photon emission computed tomography (SPECT). [$^{18}$F]-Labeled tamoxifen analogue ([$^{18}$F]FTX) was prepared in 30–40% yield and [$^{131}$I]-labeled tamoxifen analogue ([$^{131}$I]ITX) was prepared in 20–25% yield. In mammary tumor-bearing rats, the biodistribution of [$^{18}$F]FTX at 2 h showed a tumor uptake value (% injected dose/gram tissue) of 0.41±0.07; when rats were pretreated with diethylstilbestrol (DES), the value changed to 0.24±0.017. [$^{131}$I]ITX at 6 h showed a tumor uptake value of 0.26±0.166; when rats were pretreated with DES, the value changed to 0.22±0.044. Priming tumor-bearing rats with estradiol, a tumor uptake value for [$^{131}$I] ITX was increased to 0.48±0.107 at 6 h. In the [$^{3}$H] estradiol receptor assay, tumors had a mean estrogen receptor density of 7.5 fmol/mg of protein. In gamma scintigraphic imaging studies with [$^{131}$I]ITX, the rabbit uterus uptake can be blocked by pretreatment with DES. Both iodotamoxifen and tamoxifen reduced ER(+) breast tumor growth at the dose of 50 μg in tumor-bearing mice. The findings indicate that tamoxifen analogue uptake in tumors occurs via an ER-mediated process. Both analogues should have potential for diagnosing functioning ER(+) breast cancer.

PET Imaging of Breast Tumors With [$^{18}$F]FTX

PET imaging was performed on three breast cancer patients (age 54±3) (ER+) with a positron camera (Positron Corporation, Houston, Tex.). Each patient was positioned supine in the scanner so that the detector rings would span the entire breast cancer region. A 20-min attenuation scan was performed with a 4 mCi [$^{68}$Ge]-ring source prior to [$^{18}$F]FTX. After each patient received 4 mCi of {$^{18}$F]FTX, six consecutive 20 min scans were acquired. Serial transaxial images were performed. The tomograph has a field-of-view of 42 cm on transverse and 12 cm on coronal plans. The axial resolution on the reconstructed plan is 1.2 cm. Twenty-one transaxial slices separated by 5.2 mm were reconstructed and displayed in standard uptake value (SUV) which measures the ratio of tissue [$^{18}$F]FTX uptake to that of the whole body uptake (normalized for bodyweight and injected dose) for each scan. The SUV value is generated using a dedicated computer.

PET Imaging of Breast Tumors With [$^{18}$F]FTX

In PET imaging studies with [$^{18}$F]FTX, breast tumors of all three patients showed uptake. The SUV value was between 2–5. FIG. 3 showed that the primary and metastatic breast tumors could be detected. The image was obtained at 2 hours postinjection.

In vivo autoradiographic studies of [$^{131}$I]ITX and PET imaging in humans suggest that these analogues are useful in diagnosing breast tumors and imaging tumors with ERs (e.g. meningiomas) (22).

In human using PET with [$^{18}$F]FTX, the results appear encouraging because [$^{18}$F]FTX can detect primary and metastatic breast tumors. However, liver and lung uptakes were high at 2 hours postinjection. Labeling TX with I-131 could determine the optimal time to image estrogen receptor sites and evaluate breast tumor response to tamoxifen therapy In summary, we have prepared halogenated analogues of tamoxifen with higher specific activity and greater estrogen receptor affinity. *In vivo* imaging studies suggest that both halogenated analogues of tamoxifen may be good candidates for radiodiagnostic imaging of estrogen-responsive tissues.

Three patients, whose tumors had uptake of $^{18}$F-labeled tamoxifen, showed positive response to tamoxifen therapy. During 2 hours of image requisition, high uptake in the liver and lung was observed, which affected the image of tumors in the vicinity of the liver and lung. Others have reported that liver and lung have uptake of tamoxifen during 3 or 14 days of therapy (nothing noted to put in between parenthesis) (3). In view of the inventors data, either delayed images or a hydrophilic tamoxifen ligand would be desired to clear the high uptake in the liver and lung. The present inventors experience with $^{131}$I-labeled tamoxifen indicates that the tumor/blood count density ratio is optimal at 24 hours postinjection.

Figure 21:
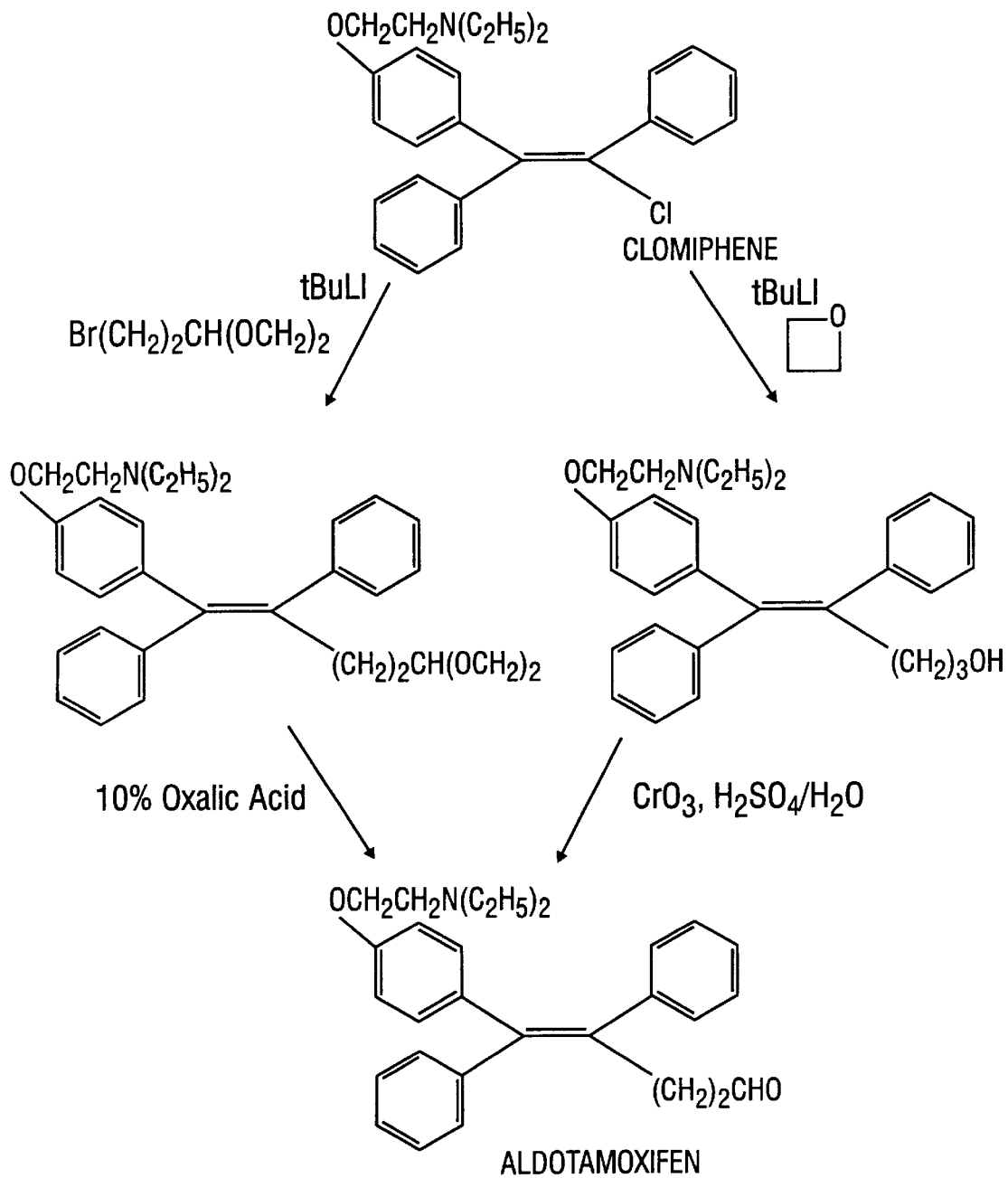
FIG. 21 Synthesis of Aldotamoxifen.
Figure 22:
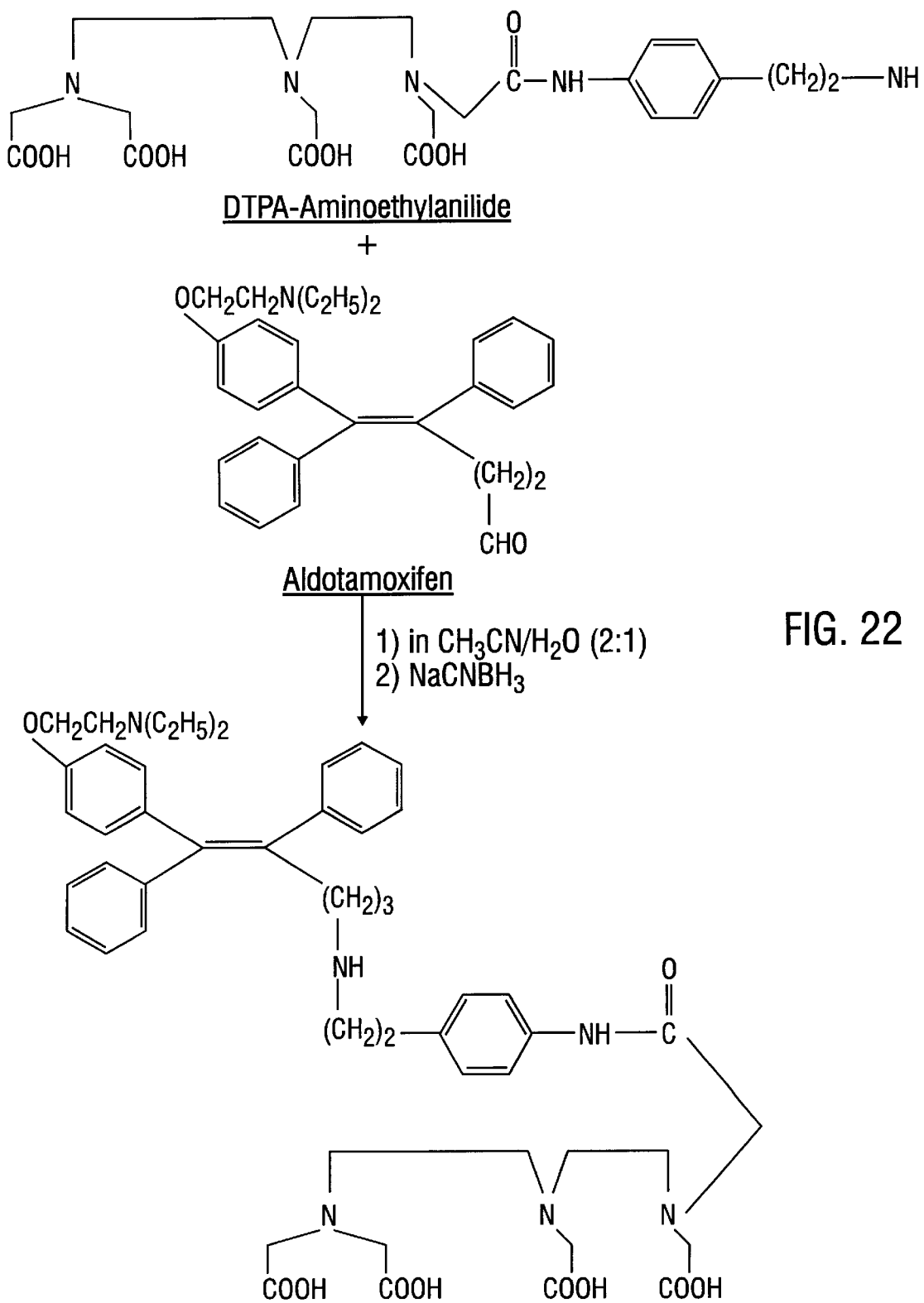
FIG. 22 Synthesis of DTPA—Tamoxifen conjugate.
Figures 24A, 24B:
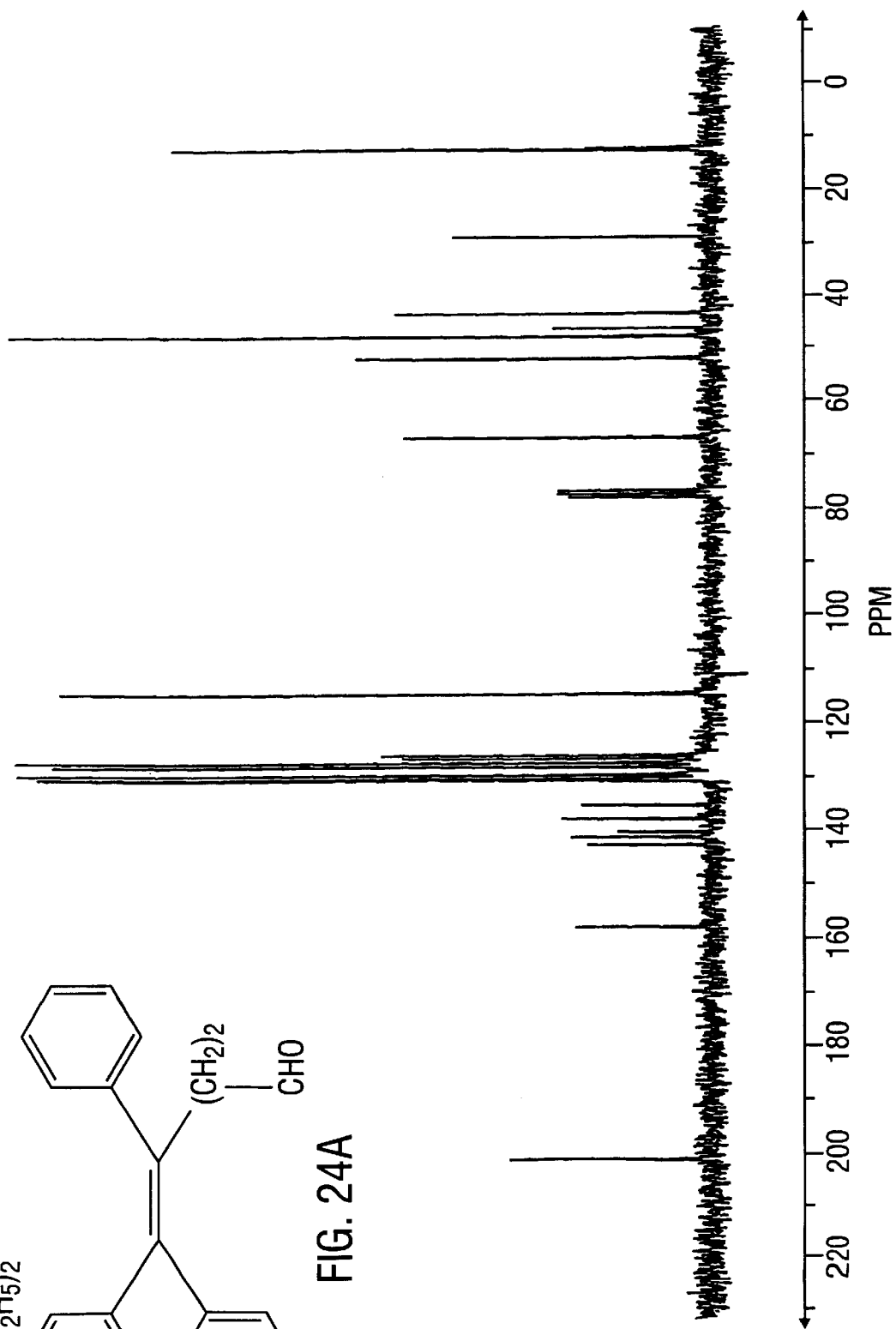
FIG. 24 $^{13}$C-NMR of Aldotamoxifen.

A clinical iodotamoxifen protocol proposed for use in conjunction with the present invention is as follows: (inventor). Efficient synthesis of a new tamoxifen-diethylenetriaminepentaacetic acid (DTPA-TX) ligand is also demonstrated by the present inventors. This ligand is more hydrophilic than tamoxifen. Additionally, this DTPA-TX conjugate can be chelated with In-111 for SPECT evaluation of ER(+) lesions. Other applications of this DTPA-TX conjugate would be chelated with gadolinium, iron or manganese for MRI diagnosis of ER(+) lesions. The synthetic scheme of DTPA-TX conjugate is shown in FIG. 21 and FIG. 22.

TABLE 16

Summary of PET Results, Receptor Assays and Response

| Patient (no) | Age (yr) | Lesion location | Visual interpr. | SUV* | Receptor ER† (fmol/mg cytosol) | assay PR‡ of protein) | Response of TX treat. | Comment |
|---|---|---|---|---|---|---|---|---|
| 1 | 55 | left breast spine | –  ± | 1.6 6.2 | 125 | 87 | poor | died 7 months later |

TABLE 16-continued

Summary of PET Results, Receptor Assays and Response

| Patient (no) | Age (yr) | Lesion location | Visual interpr. | SUV* | Receptor ER† (fmol/mg cytosol) | assay PR‡ of protein) | Response of TX treat. | Comment |
|---|---|---|---|---|---|---|---|---|
| | | sternum | ± | 4.2 | | | | |
| | | left axilla | − | 0.7 | | | | |
| 2 | 58 | mediastinum | − | 1.8 | 95 | <10 | poor | died 5 months later |
| 3 | 52 | left breast | + | 2.6 | 173 | 286 | good | improvement of bone and liver lesions on CT |
| | | right breast | + | 1.6 | | | | |
| | | right axilla | + | 2.2 | | | | |
| | | left axilla | + | 2.6 | | | | |
| | | spine | + | 3.0 | | | | |
| 4 | 56 | right axilla | − (TN) | 1.3 | 30 | 113 | poor | |
| 5 | 66 | lung | ± | 3.3 | 185 | 105 | good | improvement of lung lesion |
| 6 | 65 | left axilla | + | 2.9 | 19 | 256 | not done | surgical remove after PET study |
| 7 | 54 | skull | − | 0.9 | 54 | 273 | poor | |
| 8 | 62 | neck | − (TN) | 2.4 | 39 | 11 | not done | FAC(5FU,Adriamycin cytoxan) |
| 9 | 63 | scapula | − (TN) | 1.3 | 1132 | 970 | poor | no evidence of metastases on biopsy |
| 10 | 68 | spine | + | 6.3 | 54 | — | good | CEA down improvement of pain |

True Positive Ratio: patients 5/7 (71.4%)
Lesion: 10/14 (71.4%)
*SUV = standardized uptake ratio
‡PR = progesterone receptor
†ER = estrogen receptor
TN = true negative

EXAMPLE 26

DTPA Tamoxifen Synthesis

The present example is provided to demonstrate a preferred method for preparing the DTPA-derivatives of the invention.
Synthesis of Aldotamoxifen Clomiphene (E/Z;55/45)(4.05 g,10 mmol) was dissolved in THF and cooled at −78° C., tBuLi 1.7M (6 mL, 10 mmol) was added slowly over a period of 5 min. Bromoethyldioxolane (1.18 mL, 10 mmol) was added dropwise at −78° C. over a period of 10 min. The color of the mixture reaction which changed from brown to yellow was left to slowly return to room temperature, and then stirred for an additional 5 hours. The reaction mixture was diluted with chloroform (20 mL), and washed with water, dried over anhydrous sodium sulfate, filtered, and evaporated to dryness to yield 5.5 g of crude product. This residual crude product was purified by chromatography column on silica gel (etherpetrolium ether-triethylamine: 10:10:1) to afford the desired dioxolane compound as a syrup in the trans form (580 mg, 1.23 mmol), and cis form (560 mg, 1.19 mmol) as evidenced by 1H and 13C NMR.

Figure 4:
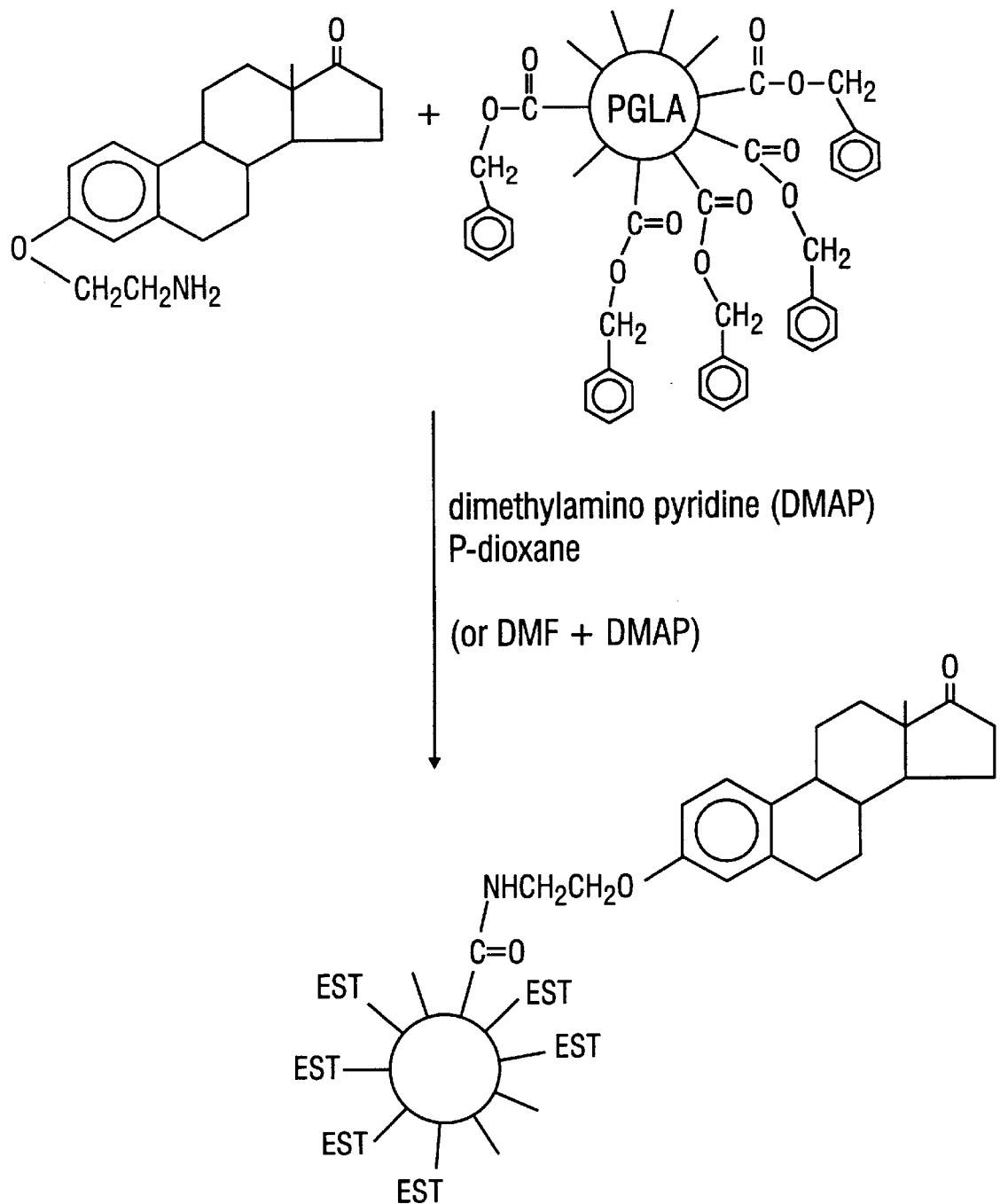
FIG. 4 Diagram of the coupling reaction between estrone (or tamoxifen) and polyglutamate (PGLA).
Figure 5:
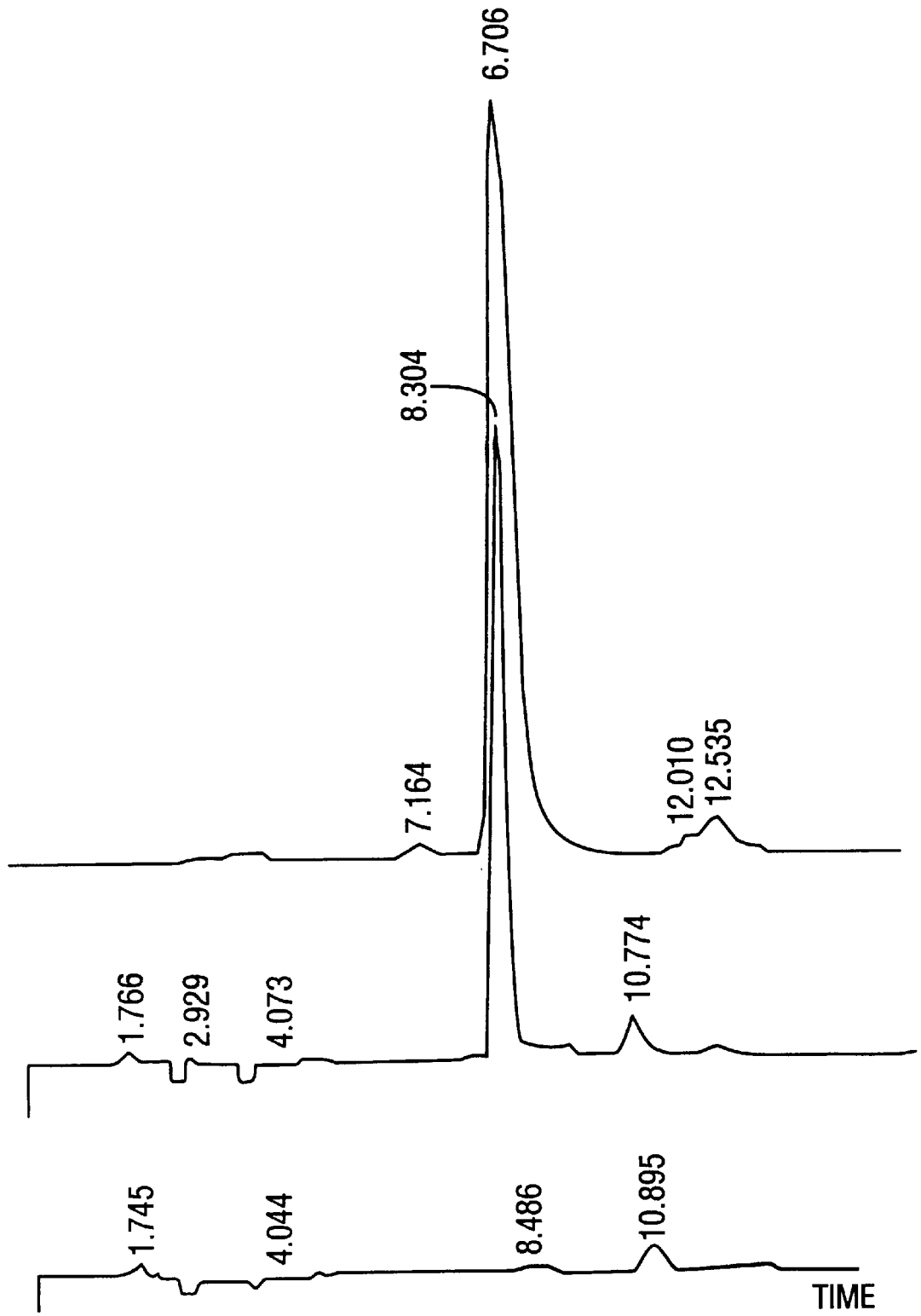
FIG. 5 HPLC Chromatogram of (trans) fluorotamoxifen.
Figure 7B:
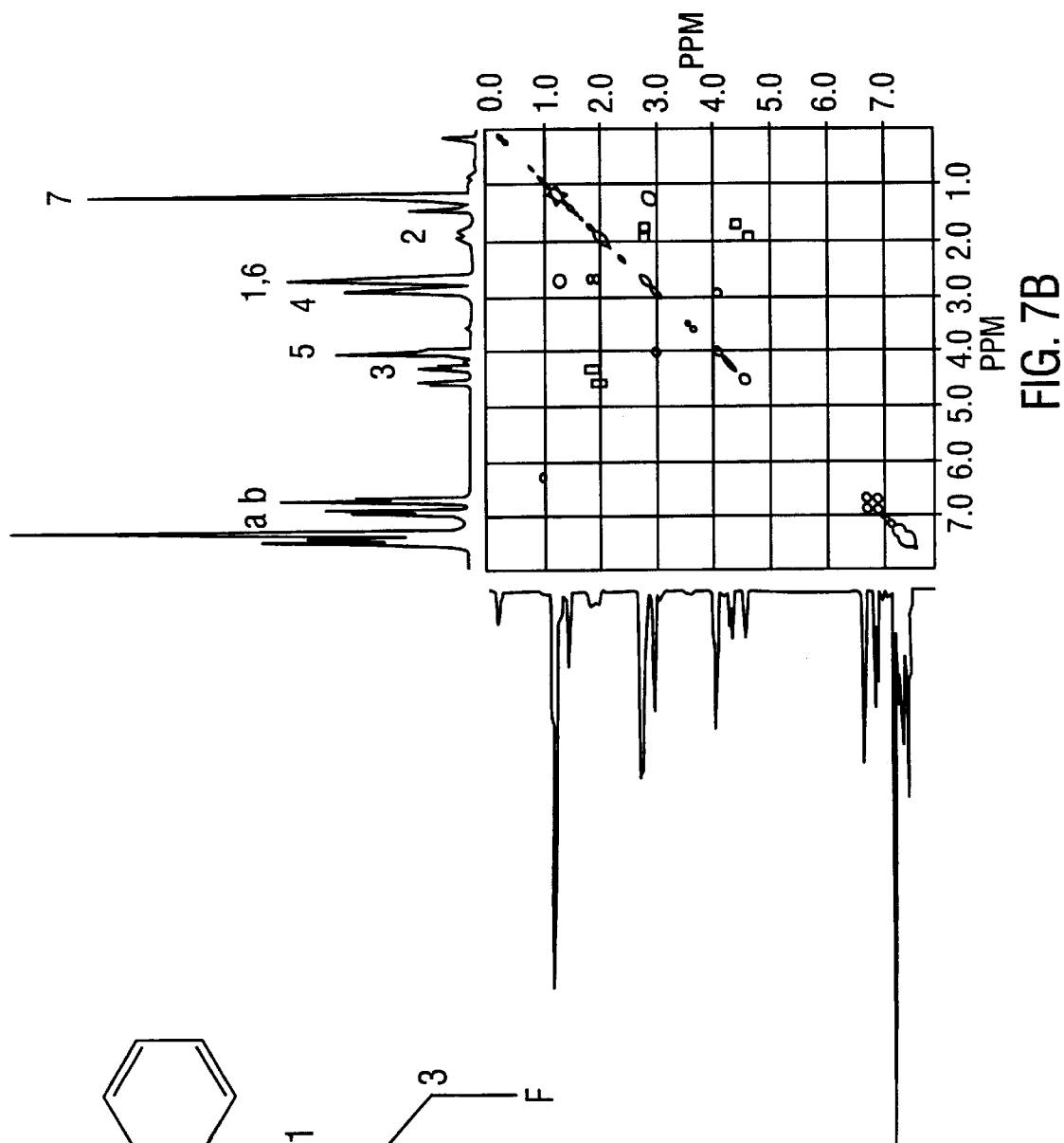
FIG. 7 (trans) fluorotamoxifen Scatchard plot analysis. Notice the presence of the ab "quartet". This quartet is only found in the trans isomer.
Figure 7A:
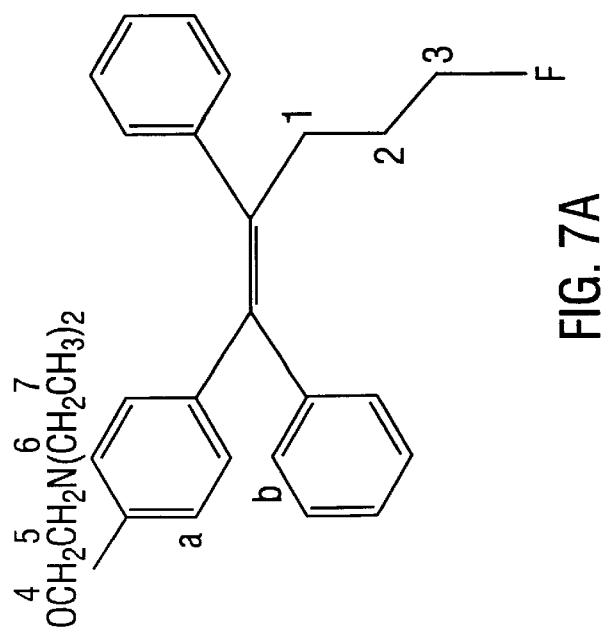
Figure 8B:
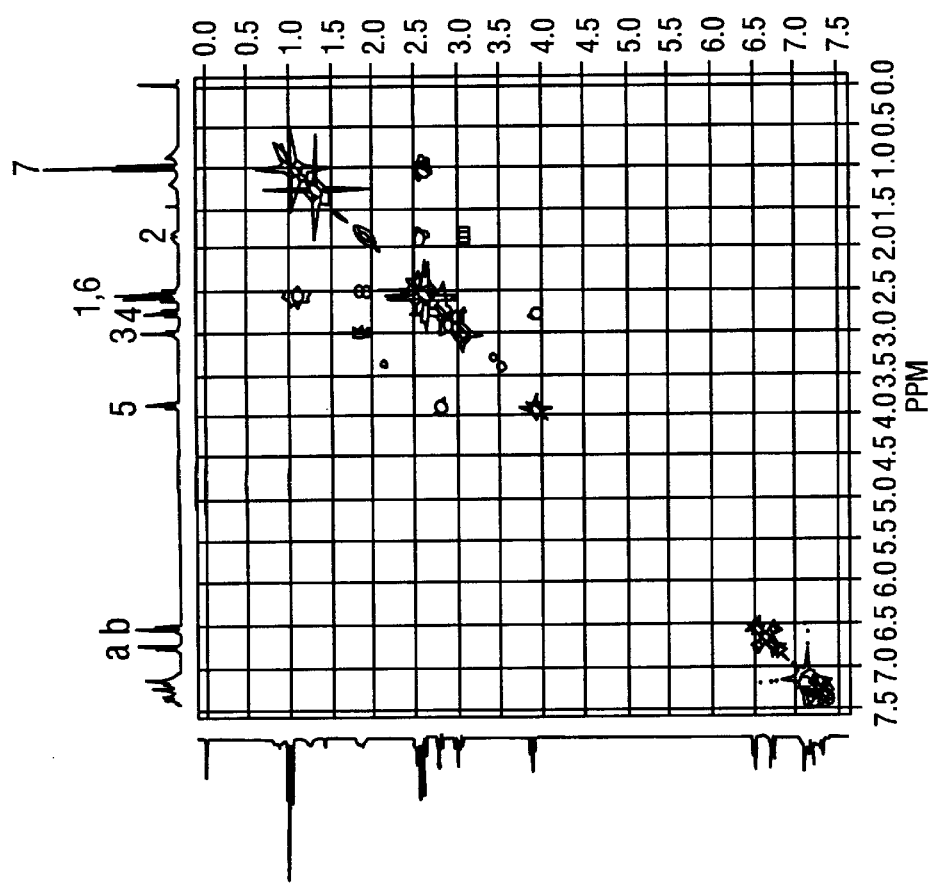
FIG. 8 (trans) iodotamoxifen Scatchard plot analysis. Notice the presence of ab "quartet".
Figure 8A:
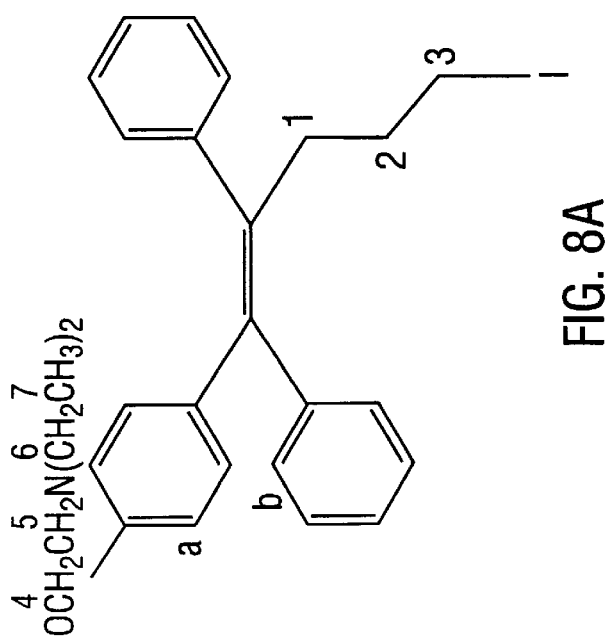
Figure 9B:
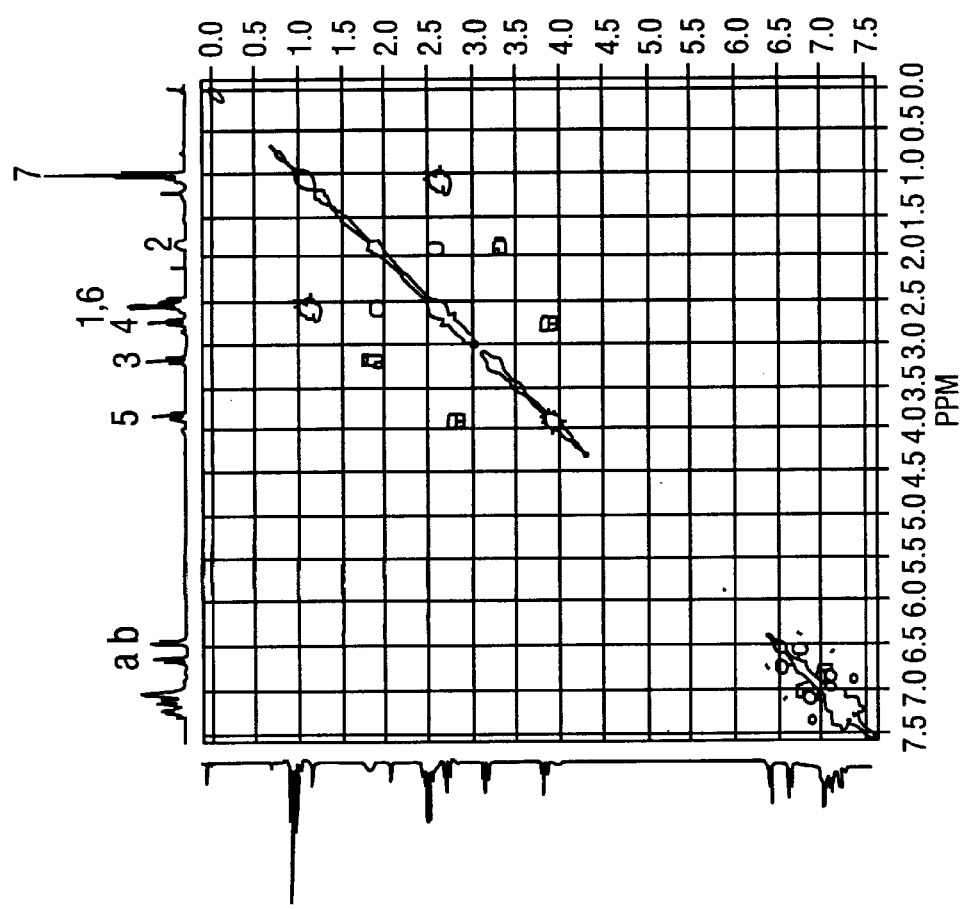
FIG. 9 (trans) bromotamoxifen. Scatchard plot analysis. Notice the presence of the ab "quartet".
Figure 9A:
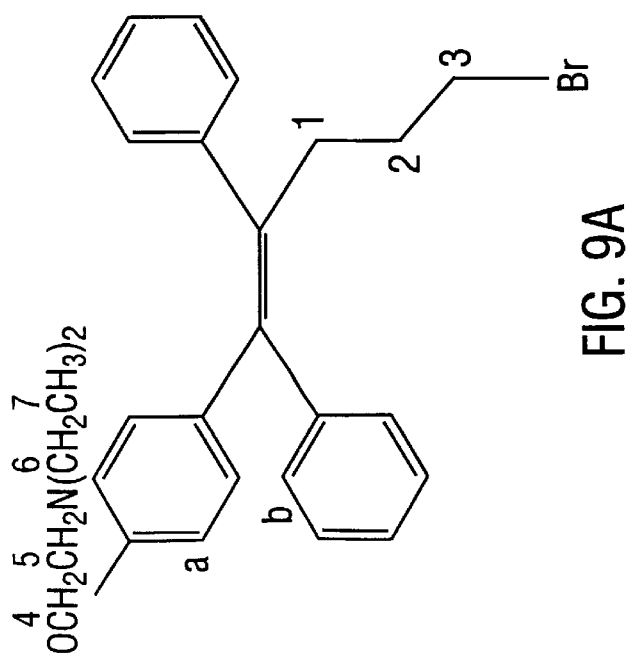
Figure 10B:
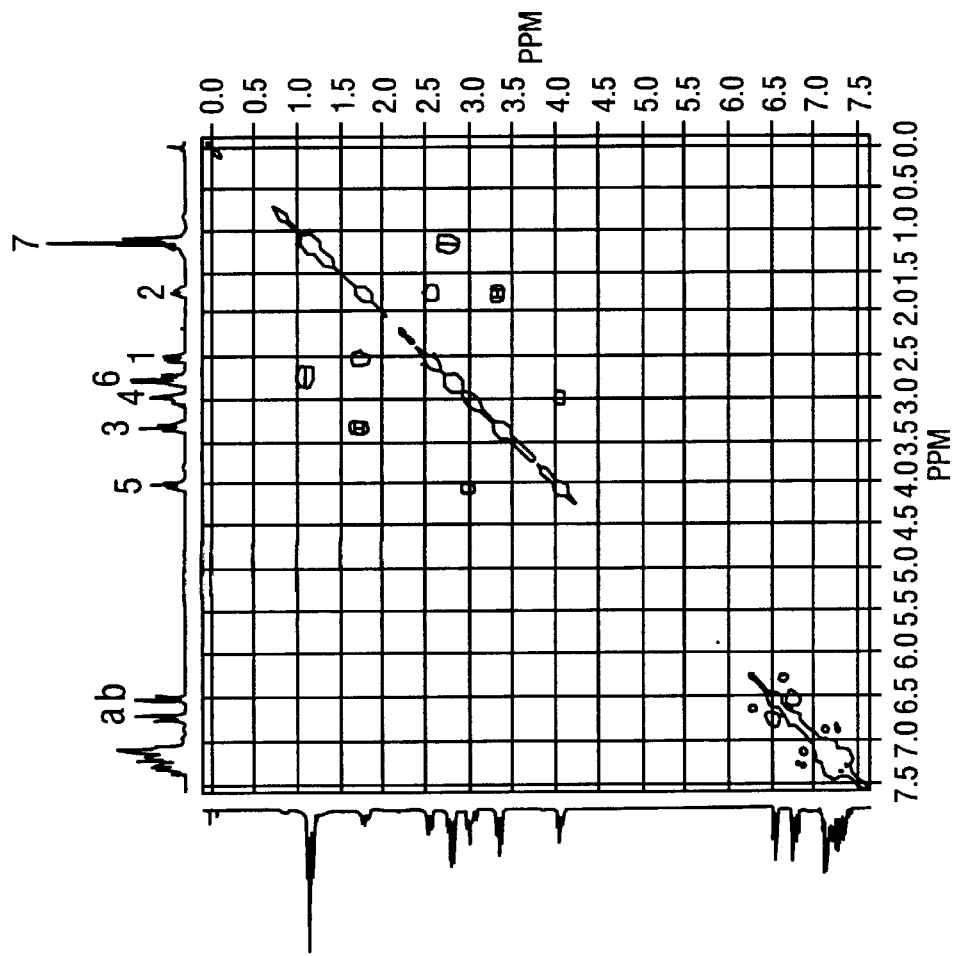
FIG. 10 (trans) bromotamoxifen. Scatchard plot analysis. Notice the presence of the ab "quartet".
Figure 10A:
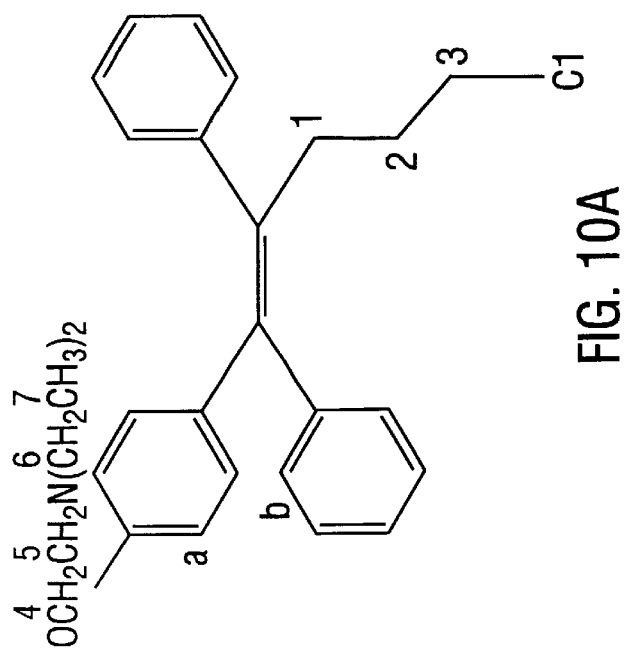

The trans dioxolane obtained previously (580 mg) was added to an aqueous solution of 10% oxalic acid (10 mLK). After 30 min of stirring, the acid was neutralized by addition of saturated solution of sodium bicarbonate. The aldehyde product was extracted with ether. The ether layer was dried over MgSO4, filtered and evaporated to dryness, yielded 500 mg (95%,1.17 mmol). The structure is determined by NMR and Mass Spectrometry. (Shown in FIG. 3, FIG. 4, and FIG. 5). 1HNMR: 9.6 (bs,1H,CHO), 7.35–7.15 (m,10,ArH), 6.75 (d,J=8.2 Hz,2H,ArH 3,5), 6.55 (d,J=8.2 Hz,2H,ArH2,6), 4.05 (t,J=6.4 Hz,2H,OCH2CH2N), 2.9–2.85 (m,4H, CHCHO and CH2CH2CHO), 2.65 (q,J=7.2 Hz,4H, NCH2CH3), 2.5 (t,J=6.4 Hz,2H,OCH2CH2N), 1.1 (t,J=7.2 Hz,6H,CH3). 13 NMR: 201.5(CHO), 158–135 (6Car), 125–130.5(10CHar), 113.5 (Ca,Cb), 66.4 (C4), 51.6 (C5)m, 47.7(C6), 43(C1), 28.4(C2), 11.8 (C7), m/z: 428(M+1, 100%), 384 (40%), 283, (30%).

The cis aldehyde isomer was obtained using the same procedure as described for the trans isomer; 1HNMR: 9.65 (bs, 1H, CHO), 7.35–7.15 (m, 10, ArH), 6.95 (d, J-8.2 Hz, 2H, ArH3, 5), 6.9(d, J=8.2 Hz, 2H, ArH2, 6), 4.(t, J-6.4 Hz, 2H, OCH2CH2N), 2.95–2.85 (m, 4H, CH2CHO and CH2CH2CHO), 2.65 (q, J=7.2 Hz, 4H, NCH2CH3), 2.5 (t, J=6.4 Hz, 2H, OCH2CH2N), 1.1 (t, J-7.2 Hz, 6H, CH3). 13 NMR: 201.3(CHO), 158–135 (6 Car), 125–130.5 (10CHar), 114.5 (Ca,Cb), 66.4 (C4), 51.8 (C5), 47.8 (C6), 43 (C1), 28.5 (C2), 11.8 (C7). m/z: 428 (M+1, 100%), 384 (45%), 283 (35%).

Synthesis of DTPA-Tamoxifen Conjugate

Figure 25:
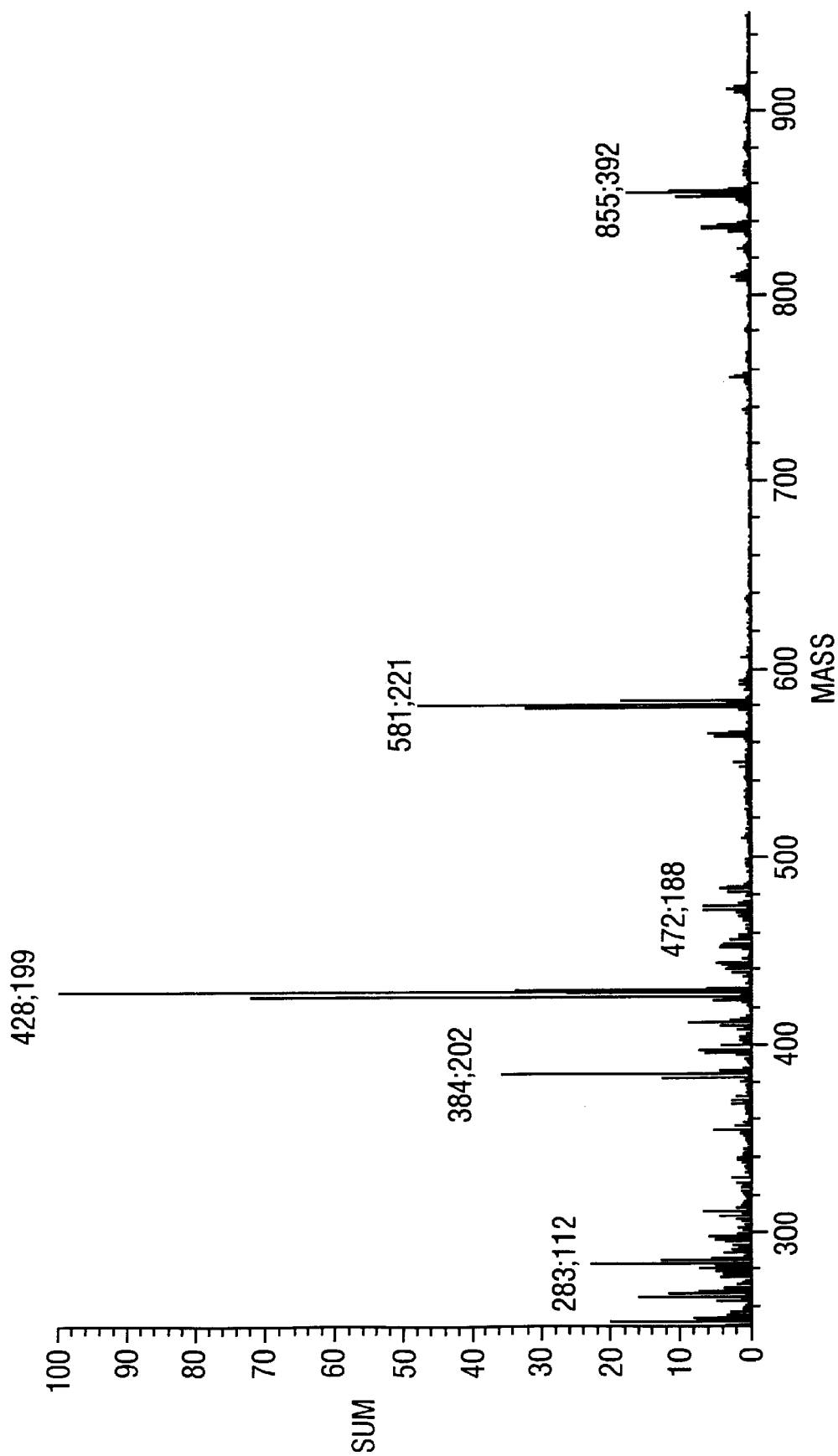
FIG. 25 Mass spectrometry of Aldotamoxifen.
Figure 26:
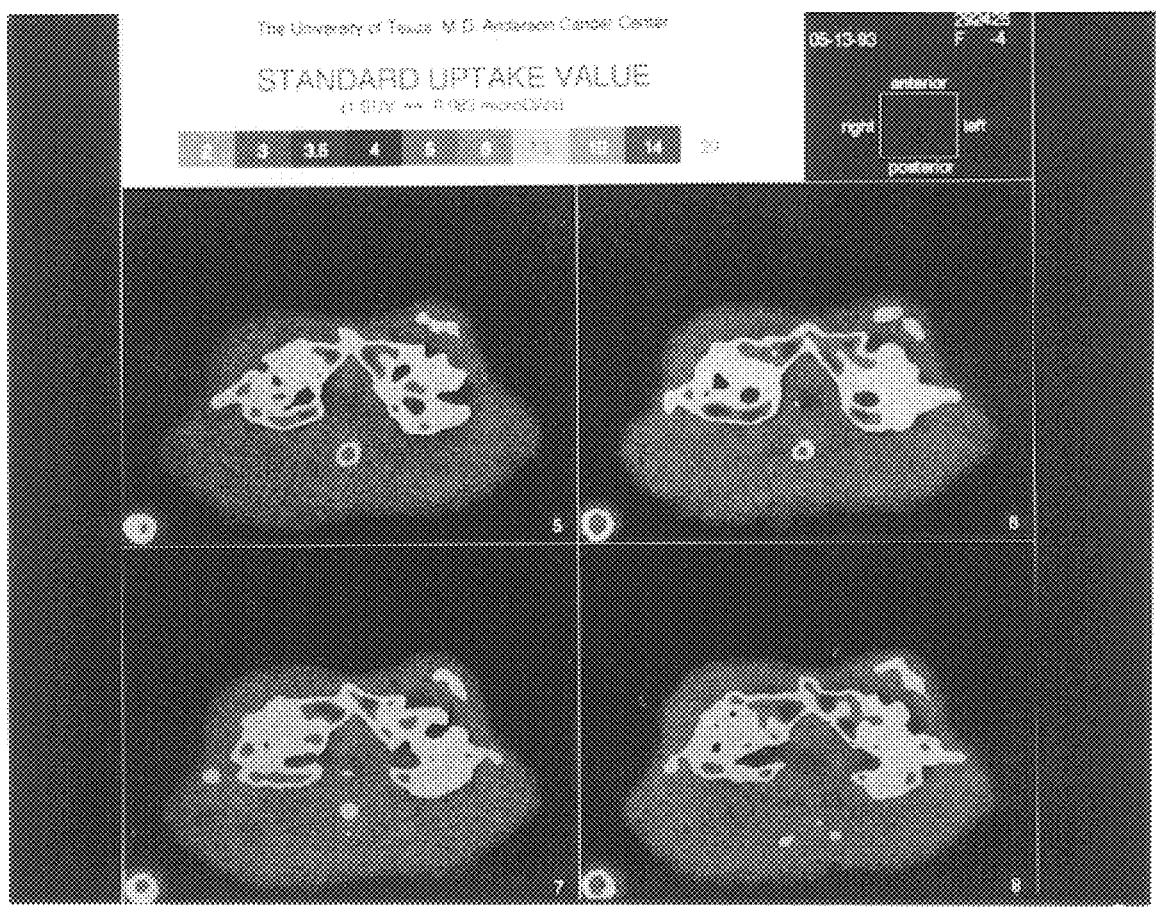
FIG. 26 PET-[$^{18}$F]FTX (4 mCi,iv) images of a patient indicated that primary (left breast) and metastatic (right lymph node) breast tumors could be detected at 2 hours postinjection. The lesions were also confirmed by tumor biopsy. The image represents one of three patients.
Figure 28:
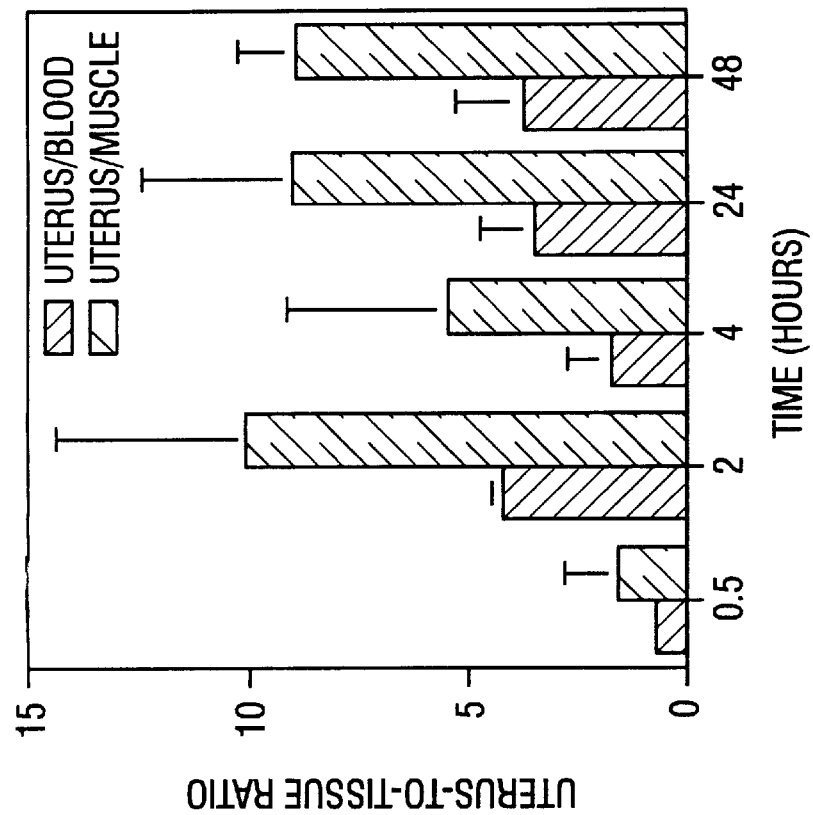
FIG. 28 In$^{111}$ DTPA Tamoxifen Biodistribution
tumor/blood
tumor/muscle
Figure 27:
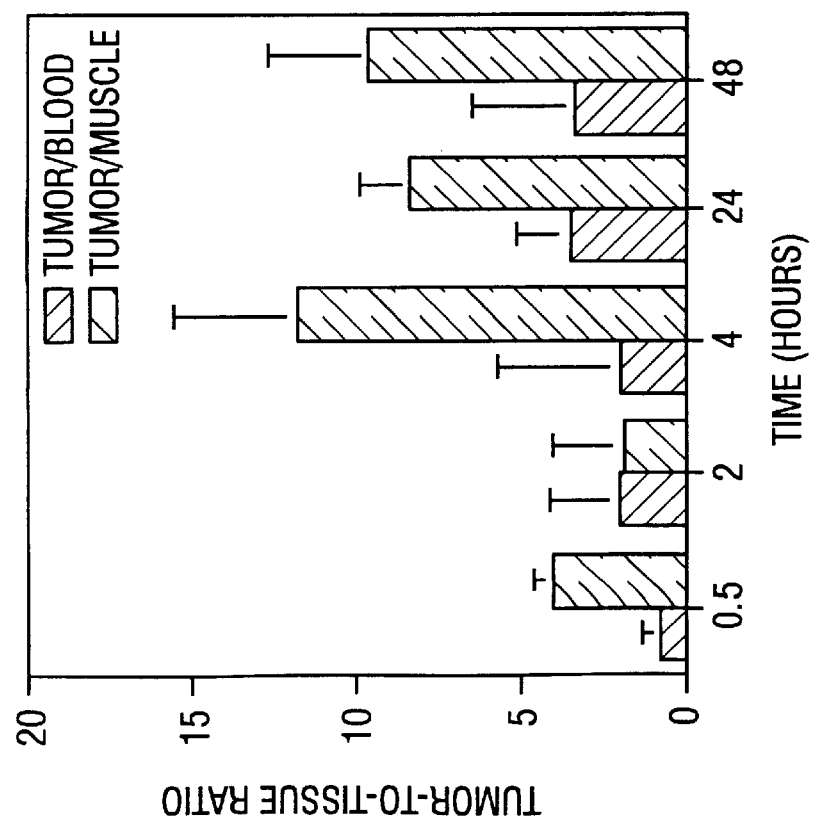
FIG. 27 In$^{111}$ DTPA Tamoxifen Biodistribution
tumor/blood=0.69–3.74
tumor/muscle=4–10
Figure 29:
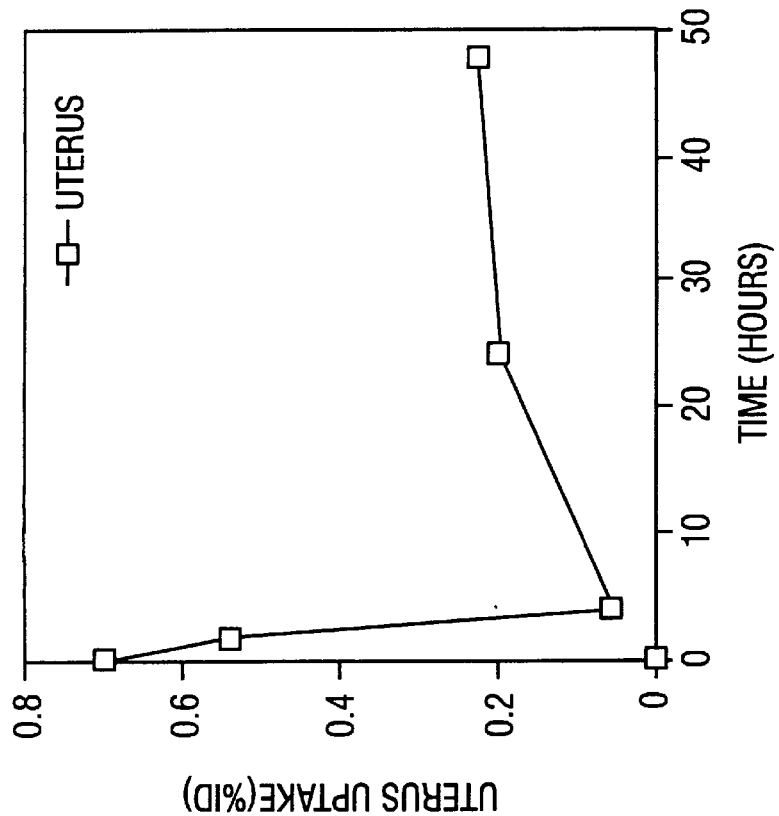
FIG. 29 In$^{111}$ DTPA Tamoxifen Biodistribution (tumor uptake (% ID) v. Time).
Figure 30:
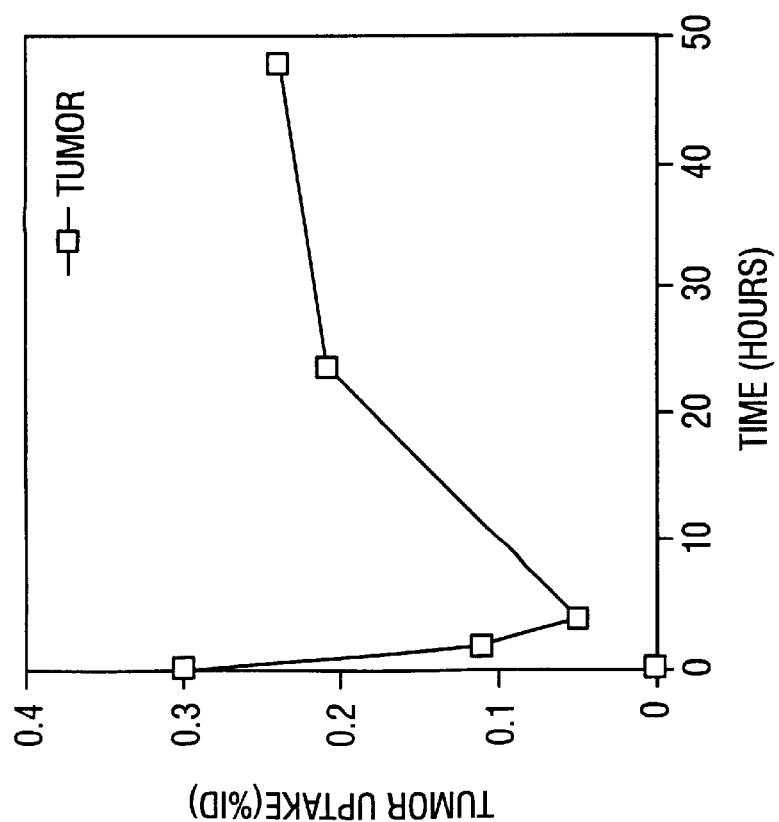
FIG. 30 In$^{111}$ DTPA Tamoxifen Biodistribution (uterus uptake (% ID) v. Time).
Figure 32:
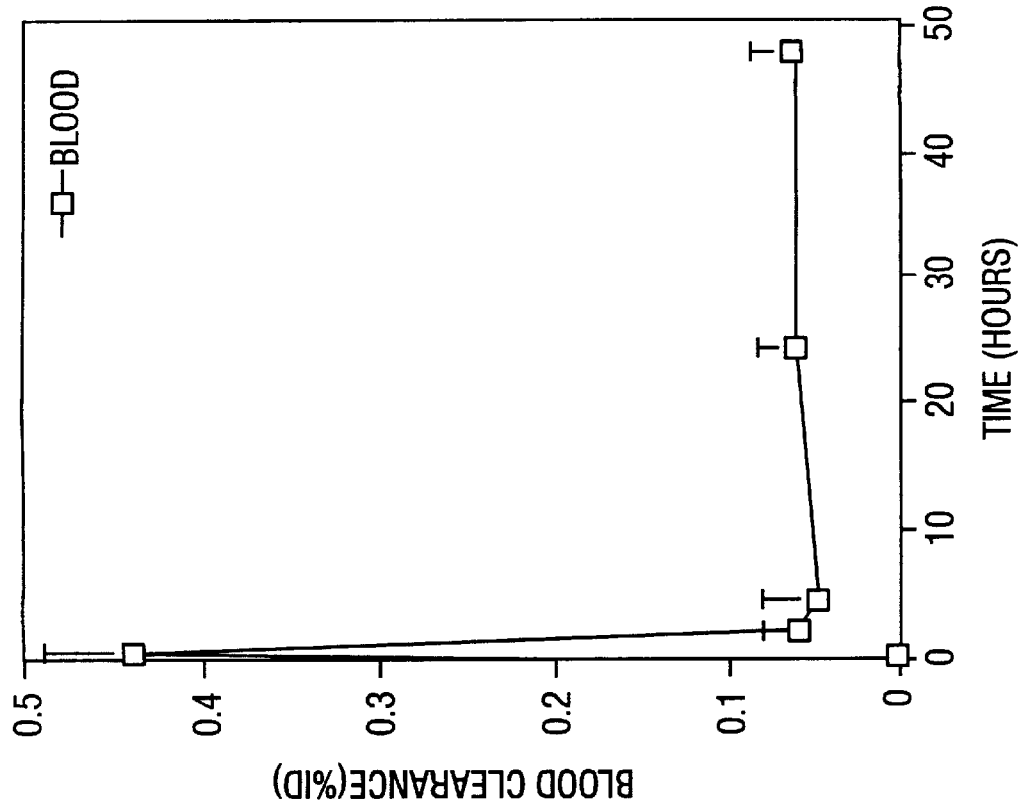
FIG. 32 In$^{111}$ DTPA Tamoxifen Biodistribution (blood clearance (ID %) v. Time)
Figure 31:
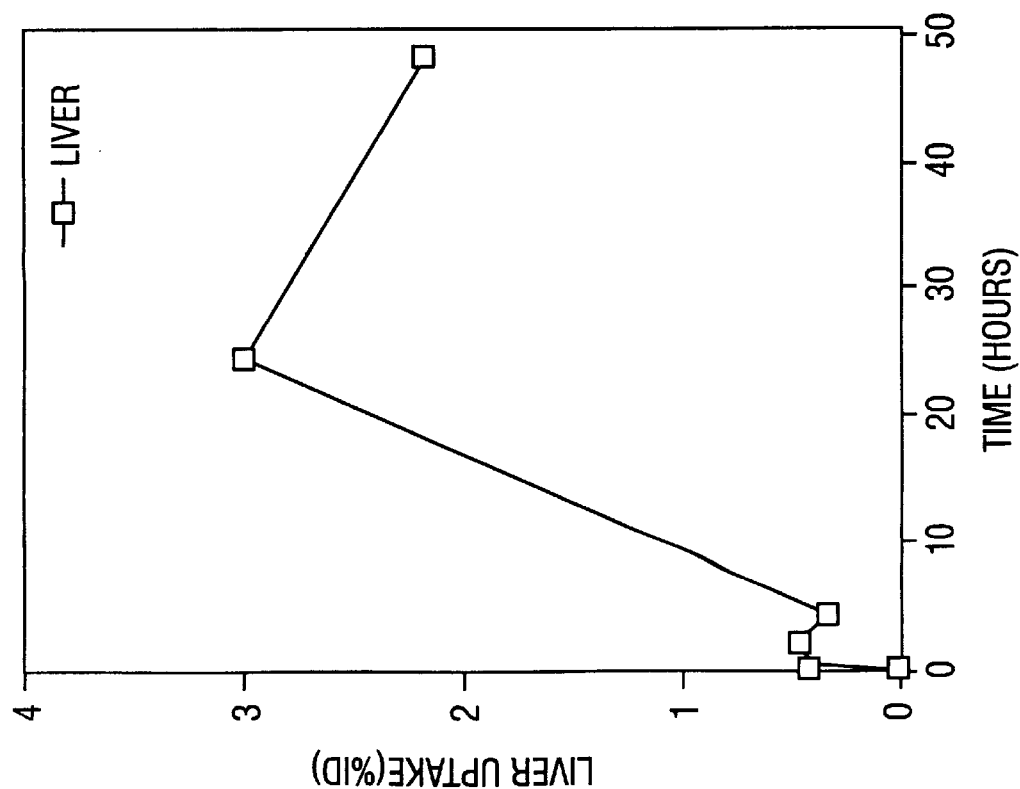
FIG. 31 In$^{111}$ DTPA Tamoxifen Biodistribution (uterus uptake (% ID) v. Time).
Figure 33A:
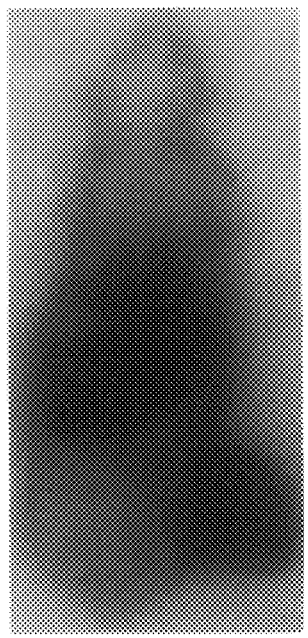
FIG. 33 $^{111}$In DTPA-TX Autoradiograms in breast tumor-bearing rats (300 μCi/rat, i.v.). Autoradiograms from 30 min., 2 hours, and 4 hours.
Figure 33B:
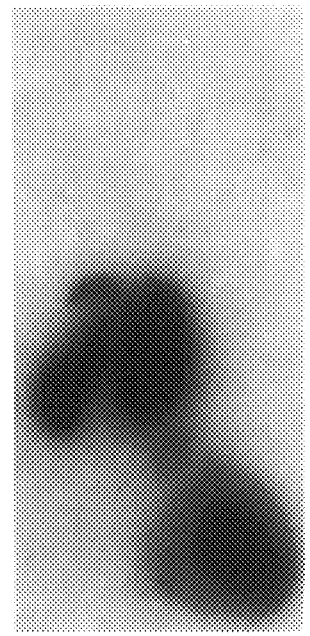
Figure 33C:
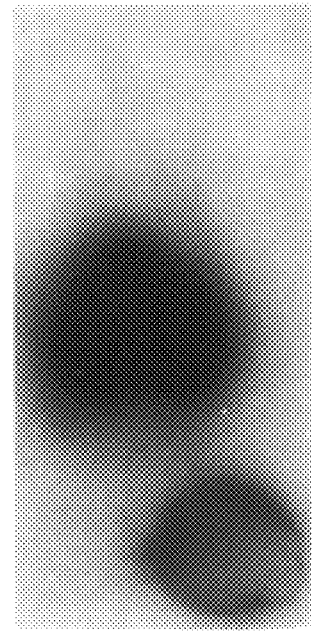
Figure 34A:
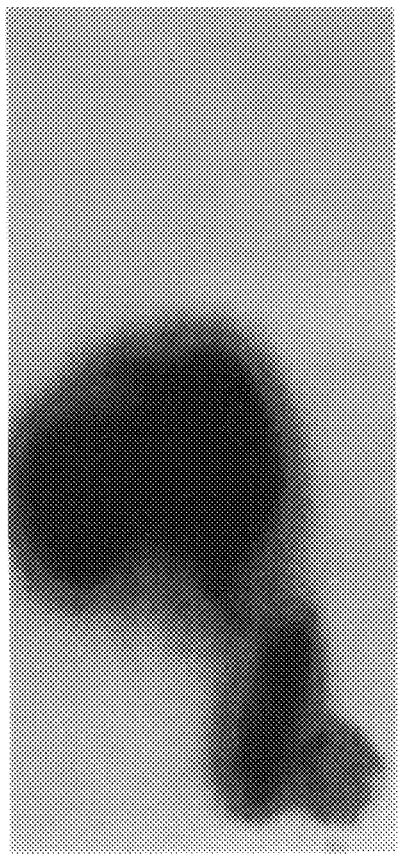
FIG. 34A and FIG. 34B $^{111}$In-DTPA-TX autoradiograms in tumor-bearing rats (300 μCi/rat, i.v.). Autoradiograms from 24 hours (FIG. 34A) and 48 hours (FIG. 34B).
Figure 34B:
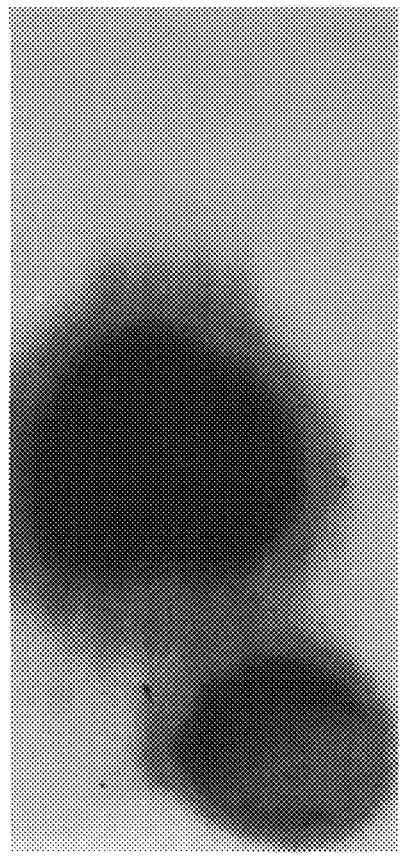
Figure 35A:
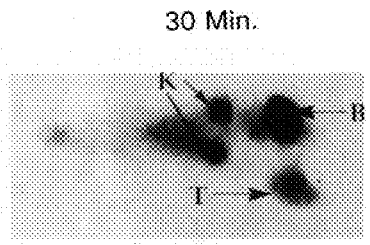
FIG. 35A, FIG. 35B, FIG. 35C. $^{111}$In-DTPA-TX -γ-scintigraphy. Anterior view of breast tumor-bearing rats receiving $^{111}$In-DTPA-TX (300 μCi, i.v.) showed increased uptake in the tumor as a function of time 1=tumor; 2=bladder; 3=liver, 4=kidneys
FIG. 35A=30 minutes.
Figure 35B:
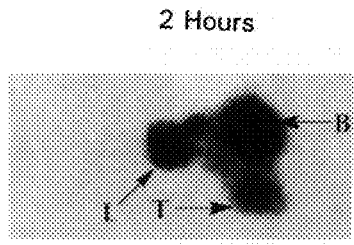
Figure 35C:
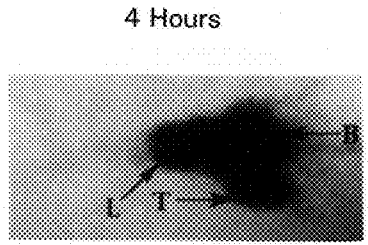
Figure 36A:
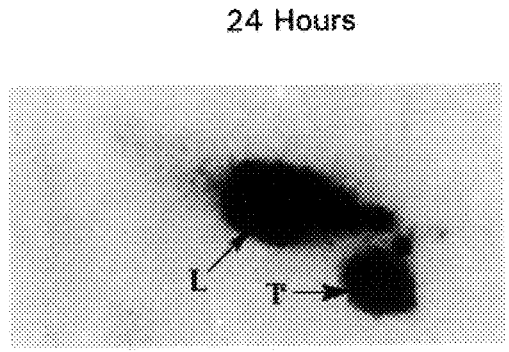
FIGS. 36A–36B Anterior view of breast tumor-bearing rats receiving $^{111}$In-DTPA-TX (300 μCi, i.v.) showed increased uptake in the tumor as a function of time.
Figure 36B:
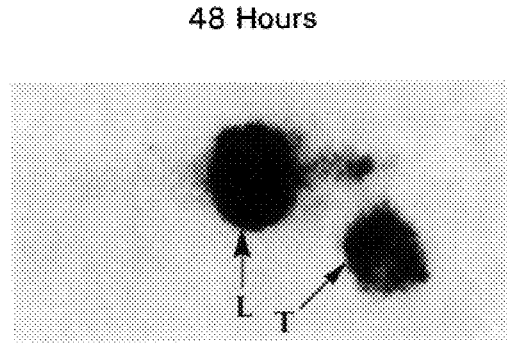
Figure 37:
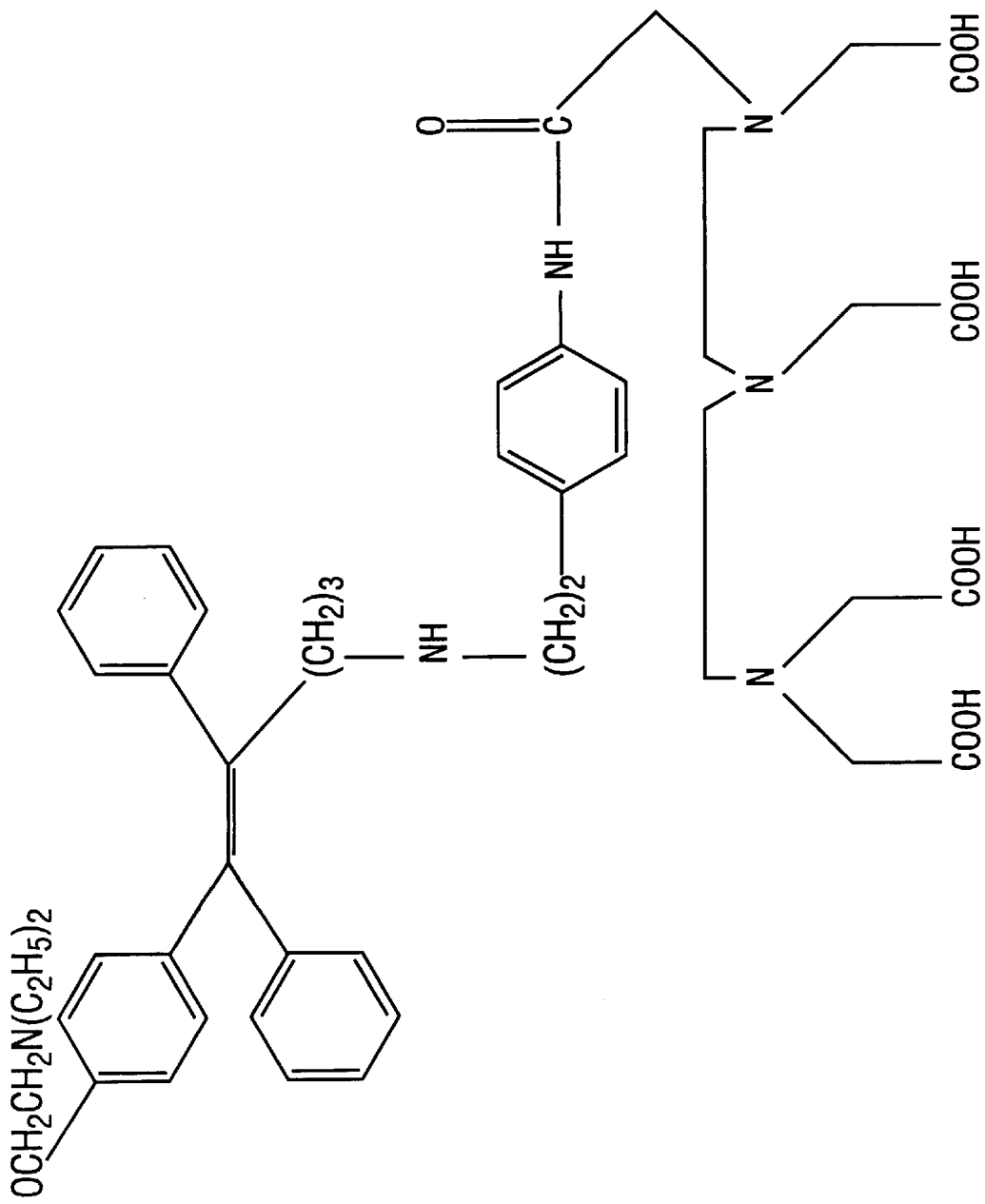

A stirred solution of aminoethylanilide-DTPA (100 mg, 0.195 mmol) (4) and aldotamoxifen (83.3 mg, 1 equiv, 0.195 mmol) in CH3CN—H2O (1:1)(8 mL) was treated with a solution of NaCN13H$_2$ (1M in THF) (0.13 mL, 0.67 equiv, 0.13 mmol). The mixture was stirred under a nitrogen atmosphere at room temperature for 2 hours. The solvent was then vaporated. The unreacted aldotamoxifen was removed by excessive washing with CH$_2$Cl$_2$(3×5 mL). The final product was used without further purification. The characterization of DTPA-TX is shown in FIG. 25 and FIG. 26.

Radiosynthesis of $^{111}$In-DTPA-TX

DTPA-TX conjugate (5 mg) was dissolved in 1 mL of ethanol/water (2:1) mixture. An aliquot containing 0.1 mg DTPA-TX was added with [111]InCl$_3$ (0.7 mCi, in 20 ul, 0.04 N HCl; NEN Dupont, Boston, Mass.). Sodium acetate (0.6 N, 20 ul) and sodium citrate (0.06 N, 20 ul) were added. The mixture stood for 30 min. The purity was determined to be greater that 99% (using CHCl$^3$/MeOH;1:1, Rf=0.2, Bioscan, Washington, DC).

Results

This characterization data demonstrates DTPA was soluble in water, but the conjugate was not. The IT remained the same. Characterization of DTPA-TX solubility, IR(cm$^{-1}$) and NMR (D$_2$O), UV (254 nm), melting point (° C.) and mass spec was compared to that of DTPA in Table 17.

procedure to obtain tissue for receptor analysis. Also, labeled DTPA-Tx is more hydrophilic than tamoxifen or estradiol, thus, it has less uptake in liver and lung. In addition, the DTPA-Tx is also easier to prepare. The DTPA-Tx also has utility as a marker molecule, as it may be used to evaluate the causes behind the failure (40%) of tamoxifen therapy when indicators are ER(+).

TABLE 17

Characterization of DTPA-Tamoxifen

| | Solubility | IR (cm$^{-1}$) | NMR (D$_2$O) | UV (254 nm) | Melting Point (° C.) | Mass Spec. |
|---|---|---|---|---|---|---|
| DTPA-TX* | EtOH/H$_2$O (1:2) CH$_3$CN/H$_2$O (1:2) | 1720 (C=O) | 7.0 ppm (aromatic) | 0.945 (1 mg/MeOH) | >320 | 958.5(M + HCl)$^+$ 912.7(—CO$_2$H) 840(—(CH$_2$CO$_2$H)$_2$) 798.0 |
| DTPA | H$_2$O | 1720 (C=O) | — | 0.280 (1 mg/MeOH) | 221 | 512.2(M$^+$) |

*DTPA-TX; DTPA-tamoxifen.
+DTPA; DTPA-p-(amino ethyl) anilide.
M.P.: melting point.
M.S.: mass spectrometry.
N.M.R.: Proton nuclear magnetic resonance.

Radiosynthesis

In this no-carrier-added synthesis, the radiochemical yield is 100%, with a radiochemical purity $\geq$99%.

Figure 18A:
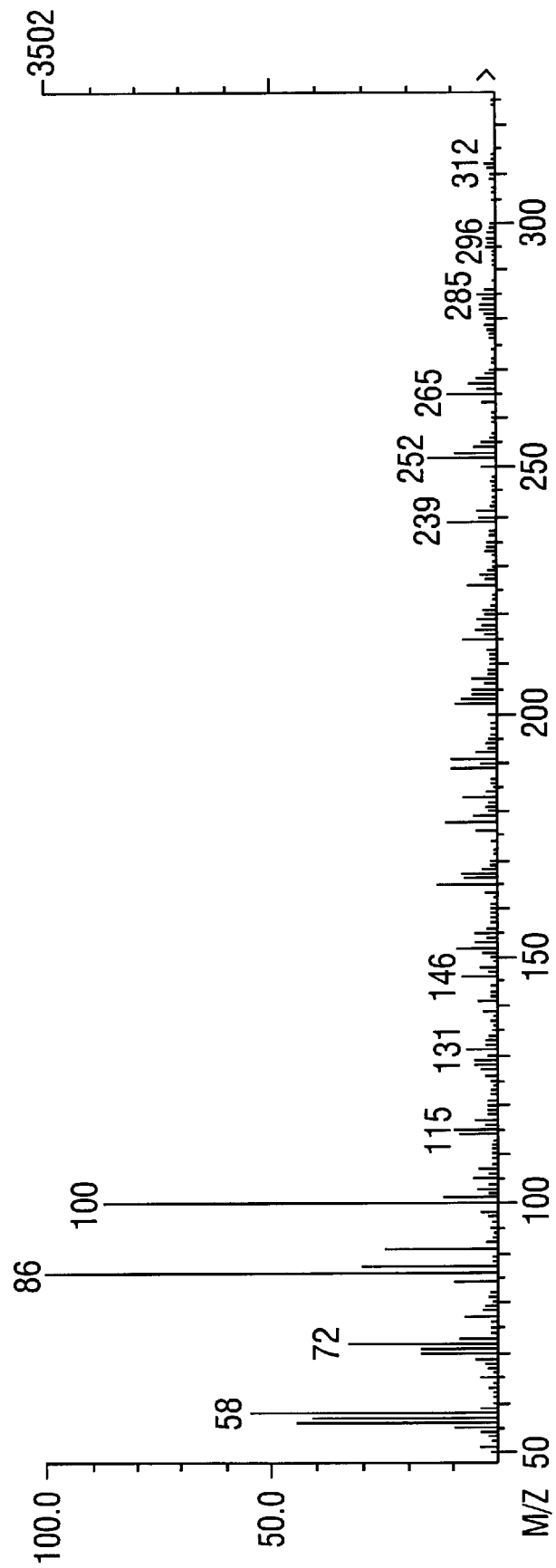
FIG. 18 Mass Spec. of TX-NH$_2$
Figure 18B:
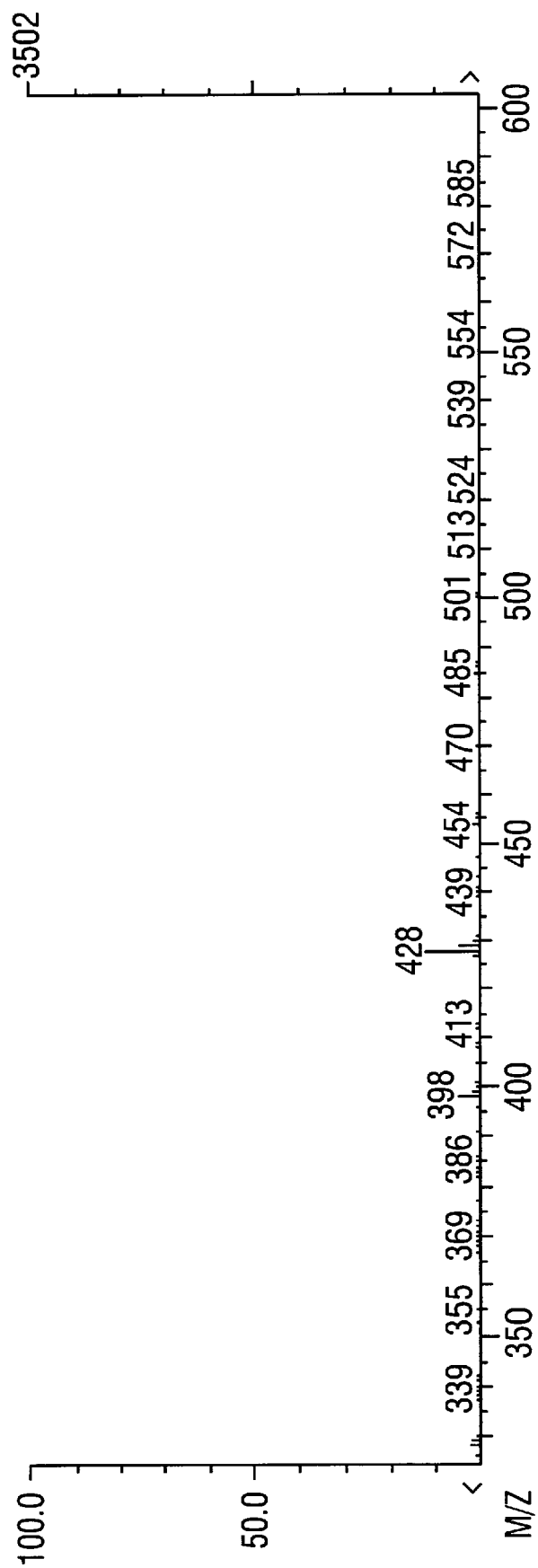

The precursor for the preparation of labeled DTPA-TX and the method of use are further embodiments of the present invention. This precursor is diethylenetriaminepentaacetic acid-tamoxifen conjugate (structure shown in FIG. 18). Such a precursor can be radiolabeled with $^{153}$Gd (t ½ 241 d), $^{59}$Fe (t ½=45 d), and $^{54}$Mn (t ½=303 days), $^{99m}$Tc (t ½, 6 h), $^{68}$Ga (t ½ 68 min). All radioisotopic ligands will be useful to detect ER(+) lesions by PET and SPECT. The unlabeled Gd-DTPA-TX, Fe-DTPA-TX and Mn-DTPA-TX will be useful to detect ER(+) lesions by MRI.

$^{111}$In-DTPA-TX can detect ER(+) breast tumors, it is useful to detect other ER(+) lesions (e.g. ovarian cancer, meningioma, endometriosis). It can also be used for the evaluation of chemotherapy response to ER(+) diseases.

EXAMPLE 27

DTPA-TX For Detection of ER(+) Lesions

The present example outlines a method by which the DPTA-Tx may be used to detect ER(+) lesions in vivo. DTPA-Tx can be chelated with other inorganic metals (e.g. Gd, Mn, Fe), and therefore has application in the detection of ER(+) lesions by MRI (magnetic resonance imaging).

The advantages of the use of the presently described method is that the labeled DTPA-Tx may noninvasively identify ER(+) recurrences without resorting to surgical The DTPA-tamoxifen derivative is particularly well suited for these and many other uses, as its precursor, may be stored in kit form. When needed, the precursor may then be conveniently reconstructed to provide the DTPA-tamoxifen derivative.

In Vivo Tissue Distribution Studies

The biodistribution of $^{111}$In-DTPA-TX in breast tumor-bearing rats is shown in Tables 18 and 19. The tumor-to-blood and tumor-to-muscle ratios increased as a function of time. At 24 and 48 hours postinjection, liver uptake was increased suggesting that this could be due to DTPA-TX metabolites. Bone uptake did not alter significantly suggesting lack of in vivo indium dissociation from the molecule. The biodistribution data is shown in FIG. 8, FIG. 9, FIG. 10, FIG. 11, FIG. 12, and FIG. 13.

Assay of $^{111}$In-DTPA-TX Biodistribution in Breast-Tumor-Bearing Rats

Female Fischer 344 rats (250–275 g) Harlan, Inc., Indianapolis, Ind.) were inoculated with mammary tumor cells using the 13762 tumor cell line (s.c. 10$_5$ cells/rat). This tumor cell line is specific to Fischer rats. After 14 days, a tumor size of 1–2 cm was observed. In tissue distribution studies, five groups of rats (N=3/group) were anesthetized with ketamine (10–15 mg/rat). The $^{111}$In-DTPA-TX reconstituted in 5% ethanol/saline was given to the five groups of rats (10 uCI/rat, iv) and tissue distribution was studied at 30 min, 2 h, 4 h, 24th and 48 h intervals. The tissues were excised, weighed and counted for radioactivity. The percent of injected dose per gram of tissue weight was determined.

TABLE 18

Biodistribution of $^{111}$In-DPTA Tamoxifen in Breast Tumor Bearing Rats
(Percent of Injected Dose Per Gram Weight; N = 3/Time Interval)

| | 30 min | 2 hr | 4 hr | 24 hr | 48 hr | 4 h$^2$ | 4 h(blocked)2 |
|---|---|---|---|---|---|---|---|
| /Blood | 0.439 ± 0.040 | 0.057 ± 0.015 | 0.043 ± 0.036 | 0.060 ± 0.021 | 0.067 ± 0.021 | 0.082 ± 0.002$^3$ | 0.039 ± 0.001 |
| Heart | 0.166 ± 0.010 | 0.025 ± 0.005 | 0.022 ± 0.013 | 0.022 ± 0.054 | 0.044 ± 0.004 | 0.037 ± 0.001$^3$ | 0.015 ± 0.001 |
| Lung | 0.368 ± 0.117 | 0.063 ± 0.037 | 0.037 ± 0.027 | 0.126 ± 0.023 | 0.125 ± 0.011 | 0.056 ± 0.016 | 0.041 ± 0.022 |
| Liver | 0.421 ± 0.037 | 0.464 ± 0.075 | 0.339 ± 0.017 | 0.301 ± 0.750 | 2.192 ± 0.392 | 0.077 ± 0.025 | 0.064 ± 0.036 |

TABLE 18-continued

Biodistribution of $^{111}$In-DPTA Tamoxifen in
Breast Tumor Bearing Rats
(Percent of Injected Dose Per Gram Weight; N = 3/Time Interval)

|  | 30 min | 2 hr | 4 hr | 24 hr | 48 hr | 4 h$^2$ | 4 h(blocked)2 |
|---|---|---|---|---|---|---|---|
| Kidney | 1.262 ± 0.042 | 0.550 ± 0.153 | 0.545 ± 0.208 | 3.076 ± 0.461 | 3.243 ± 0.397 | 0.554 ± 0.052 | 0.842 ± 0.474 |
| Uterus | 0.704 ± 0.636 | 0.540 ± 0.351 | 0.064 ± 0.056 | 0.200 ± 0.037 | 0.233 ± 0.008 | 0.074 ± 0.004$^3$ | 0.045 ± 0.005 |
| Muscle | 0.255 ± 0.261 | 0.118 ± 0.086 | 0.009 ± 0.009 | 0.072 ± 0.076 | 0.026 ± 0.003 | 0.008 ± 0.002 | 0.007 ± 0.003 |
| Tumor | 0.300 ± 0.030 | 0.109 ± 0.058 | 0.089 ± 0.054 | 0.204 ± 0.043 | 0.236 ± 0.069 | 0.054 ± 0.007 | 0.040 ± 0.009 |
| Bone | 0.108 ± 0.012 | 0.795 ± 1.230 | 0.047 ± 0.058 | 0.089 ± 0.006 | 0.141 ± 0.077 | 0.030 ± 0.005 | 0.018 ± 0.009 |
| Urine | 194.362 (n = 1) | 172.59 ± 35.7 | 47.39 ± 11.65 | 0.752 ± 0.218 | 0.476 ± 0.352 |  |  |

TABLE 19

Tumor to Tissue and Uterus to Tissue Ratio of $^{111}$In-DTPA Tamoxifen
in Breast Tumor Bearing Rats (N = 3/Time Interval)

| Ratio | 30 min | 2 hr | 4 hr | 24 hr | 48 hr |
|---|---|---|---|---|---|
| Tumor/Muscle | 3.97 ± 0.56 | 1.85 ± 2.04 | 11.85 ± 3.70 | 8.56 ± 1.52 | 9.77 ± 3.11 |
| Tumor/Blood | 0.69 ± 0.14 | 1.96 ± 0.93 | 1.95 ± 0.68 | 3.58 ± 0.86 | 3.74 ± 1.43 |
| Uterus/Muscle | 1.55 ± 1.28 | 10.00 ± 4.29 | 5.44 ± 3.60 | 8.85 ± 3.39 | 8.96 ± 1.27 |
| Uterus/Blood | 0.71 ± 0.02 | 4.20 ± 0.25 | 1.67 ± 0.92 | 3.55 ± 1.00 | 3.78 ± 1.48 |

EXAMPLE 28

Estrogen Receptor Assay of Mammary Tumors

To demonstrate the 13762-cell-line-induced tumors in rats that were estrogen-receptor positive, a receptor assay was performed. Briefly, the tumor tissue (16 g) was dissected from 13762 mammary tumor-bearing female rats. The tissue was homogenized in Tris buffer (15 ml) as described previously, and then centrifuged at 100,000 g to prepare a tumor tissue cytosol. This tissue cytosol was then pretreated with dextran-coated charcoal before the assay was performed. A saturation curve was obtained for [$^3$H]estradiol ($10^{-5}$–$10^{-10}$ M) in the presence and absence of estradiol ($10^{-5}$M). Scatchard analysis was performed to determine the receptor affinity and density. Protein concentrations were determined according to the method of Lowry et al. (12). Autoradiographic Studies of [$^{131}$I]ITX in Mammary Tumor-Bearing Rats Female mammary tumor-bearing rats (n=3) after receiving [$^{111}$I]ITX (30 μCi, iv) were sacrificed at 24 hours. The body was fixed in carboxymethyl cellulose (4%) block. The frozen body was mounted to a cryostat (LKB 2250 cryomicrotome, Ijamsville, Md.) and 40 μm coronal sections were made. The section was thawed and mounted on a slide. The slide was placed in contact with x-ray film (X-Omat AR, Kodak, Rochester, N.Y.) for 48 hours.

Gamma Scintigraphic Imaging of Estrogen Receptor Sites

Gamma scintigraphic images were obtained from GE Starport System (GE Company, Milwaukee, Wis.). The image was displayed on the terminal monitor. The graphic processor displayed 256×256 pixels. Each pixel was 14 bits deep. Six New Zealand female rabbits (3–4 Kg B.W.) were administered 300 μCi of [$^{131}$I]iodotamoxifen (iv) and multiple images at 2, 24 and 48 hours were accomplished. To ascertain the radioactivity uptake in uterus is via an ER-mediated process, the rabbits were administered with diethylstilbestrol (15 mg,iv) 1 hour prior to receiving [$^{131}$I]ITX and the images were obtained at 2, 24 and 48 hours.

Results

Estrogen Receptor Assay of Breast Tumors

The estrogen receptor assay was performed as previously described. Briefly, pig uteri cytosol was prepared from a uterine homogenate containing EDTA (1.5 mM) and sodium azide (3 mM) in tris buffer (10 mM, ph 7.4). The concentrations of DTPA-TX and tamoxifen (10 nM–10 μM) were incubated with [$^3$H] estradiol (5 nM) in tissue cytosol (0.2 ml). The concentration of DTPA and tamoxifen that decreased specific estradiol binding by 50% (IC 50) was determined. Protein concentration was determined by the method of Lowry et al. (12).

From the Scatchard analysis in the estrogen receptor assay, the 13762 tumor-cell-induced tumors had an estrogen receptor density (Bmak) of 7.5 fmol/mg of cytosol protein and a receptor binding affinity (Kd) of 33 nM. Estrogen receptor assay was performed according to previous reports. Protein concentrations were determined to be 400 ug/ml. In ER(+) breast cancer patients, estrogen receptor positivity was defined as equal to or greater than 10 fmol/mg cytosol protein. Levels between 5 and 10 were considered equivocal.

Autoradiographic Studies of $^{111}$In-DTPA-TX in Breast Tumor-Bearing Rats

Figure 14:
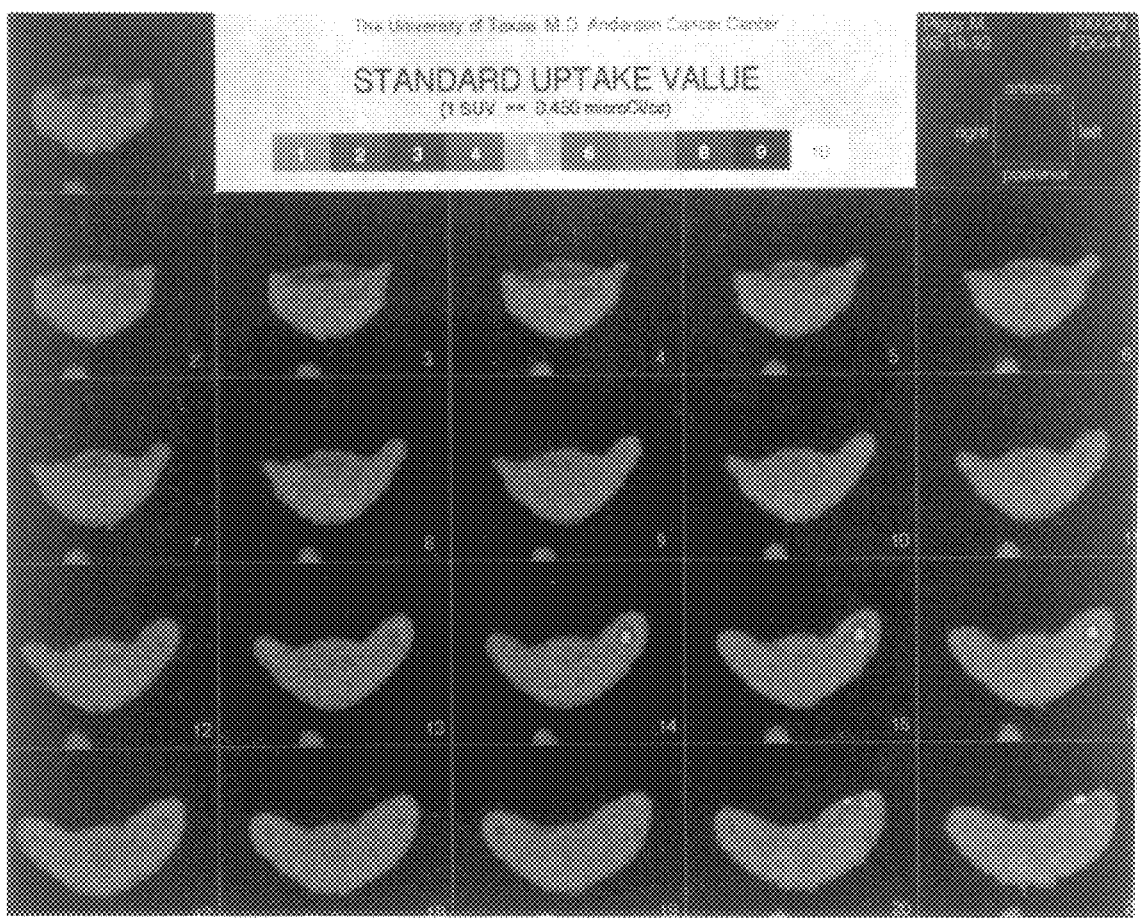
FIG. 14 PET image (transaxial) of the pelvic region of a pig pretreated with diethylstilbestrol (50 mg) 1 hour prior to giving [$^{18}$F] fluoro analog of tamoxifen (10 mCi, i.v.). The image was obtained 1 hour postinjection of [$^{18}$F] fluoro analog of tamoxifen. The pig was positioned supine and scanned from cranial to caudal. Twenty-one slices per scan were collected. From slices 1–7, the image demonstrates decreased uptake in uterus.
Figure 15:
FIG. 15 Fischer 344 rats inoculated with tumor cells in lumbar area.

In vivo autoradiographic studies in breast tumor-bearing rats indicated that the tumor could be visualized at all time intervals studied (FIG. 14 and FIG. 15).

Gamma Scintigraphic Imaging of Breast Tumors

Gamma scintigraphic images were obtained with a GE Starport System (GE Company, Milwaukee, Wis.) equipped with high resolution, medium energy, parallel-hole collimator. Five breast-tumor-bearing rats were administered 300 μCi of $^{111}$In-DTPA-TX, and whole body planar images were obtained at 30 min., 2 hrs., 4 hrs., 24 hrs., and 48 hrs.; 300,000 counts were acquired in 128×128 matrix.

In gamma scintigraphic imaging studies with $^{111}$In-DTPA-TX, the breast tumors could be well visualized at 30 min, 2, 4, 24 and 48 hours. (Shown in FIG. 16 and FIG. 17).

EXAMPLE 29

In Vivo Response of MCF-7 Human Breast Cancer Cells to Tamoxifen and Iodotamoxifen The MCF-7 human breast cancer cell line was maintained in Eagle's Minimum Essential Medium supplemented with sodium pyruvate, nonessential amino acids, L-glutamine, vitamin solution (GOBCP BRL Grand Island, N.Y.) and 5% (vol/vol) heat-inactivated fetal bovine serum, and incubated in 5% $CO_2$-95% air at 37° C. The cultures were free of mycoplasma and pathogenic murine viruses (assayed by Microbiological Associates, Bethesda, Md.). Female athymic NCr-nu/nu mice were obtained from the NCI-Frederick Cancer Research Facility (Frederick, Md.). The mice were maintained in specific-pathogen-free conditions in a facility approved by the American Association for Accreditation of Laboratory Animal Care.

Tumor cells in log-phase growth were harvested by trypsinization and $2\times10^6$ cells in 0.1 ml of PBX injected into the mammary fatpad of the nude mice. A 60-day release pellet containing 0.72 17-β estradiol (Innovative Research of America, Toledo, Ohio) was implanted s.c. in each animal. After 20 days the 17β estradiol peppet was removed from one group, and these mice were not treated further. The remaining mice were treated daily for 6 weeks with s.c. injections of either 50 µg of Tamoxifen or Iodotamoxifen in 0.1 ml of peanut oil, or with oil alone. The tumors were measured twice weekly, and the tumor volumes calculated with the formula $W^2\times L/2$, where W=smaller.

Results

Figure 39:
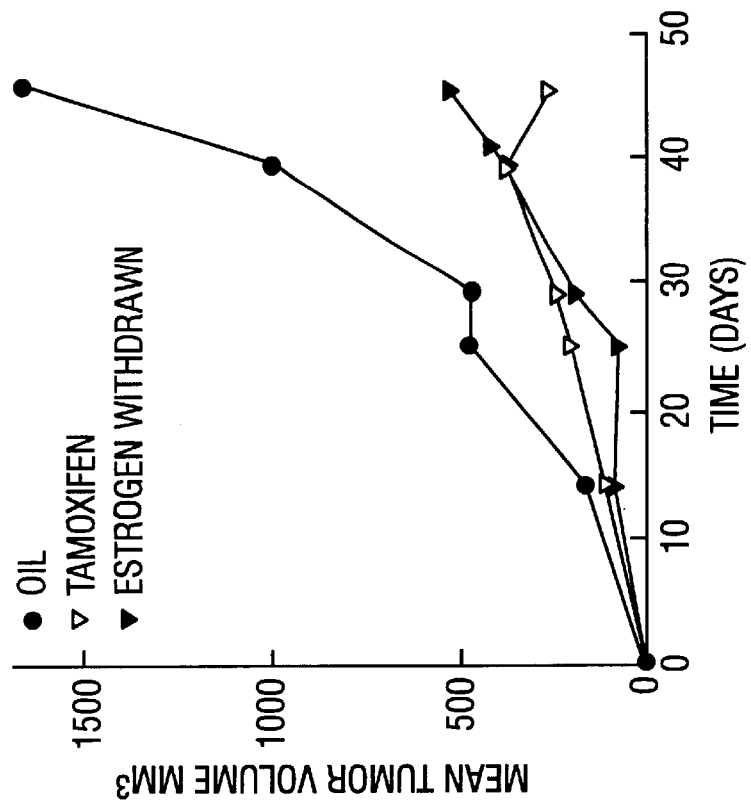
Figure 38:
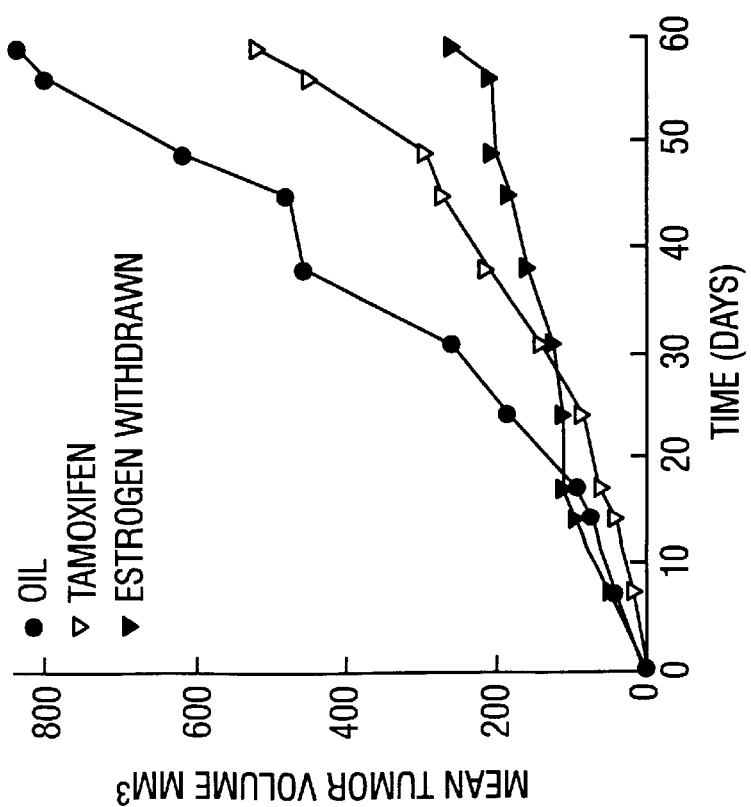
Figure 40A:
FIGS. 40A and 40B τ-Scintigraphy images of a rabbit primed with DES (1 mg/day, 3 d,sc) (FIG. 40A) followed by $^{131}$I-iodotamoxifen (0.5 mCi, iv) (FIG. 40B); after blocking with DES (15 mg, iv), the uterus showed decreased uptake with $^{131}$I-iodotamoxifen (FIG. 40C.
Figure 40C:
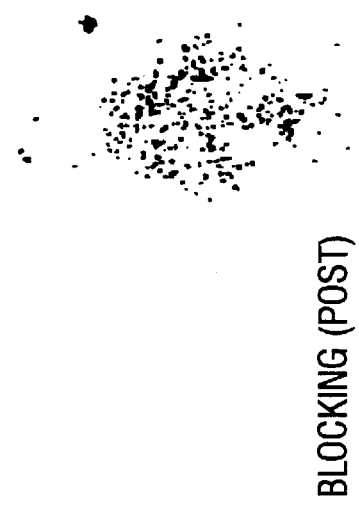
Figure 40B:
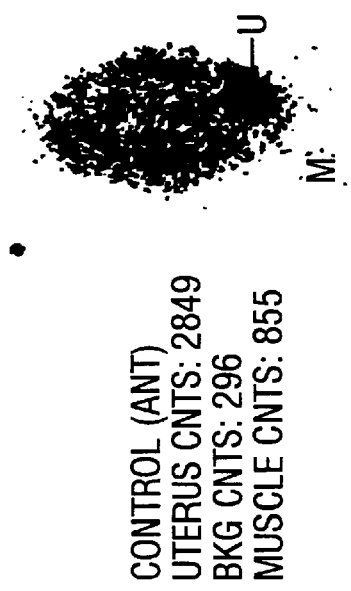
Figure 40D:
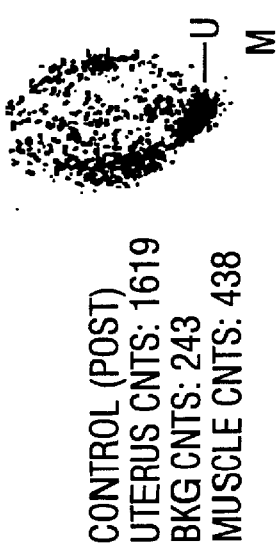
FIG. 40D).

The MCF-7 human breast cancer cell line grew progressively in the nude mice in the presence of 17-β estradiol. There was only minimal tumor growth in the animals from which the estradiol pellets were removed on day 20 (FIG. 38). In the mice treated with either tamoxifen or iodotamoxifen, the growth of the MCF-7 tumors was greatly reduced compared with the tumor growth in the control groups (FIG. 38 and FIG. 39). The results demonstrate that iodotamoxifen is active in vivo and can suppress the growth of hormone-dependent human breast cancer cells.

EXAMPLE 30

Example Methods for Selecting (Screening) Patients for Tamoxifen Treatment

The present example outlines a method using the various tamoxifen derivatives of the present invention to screen patients in tamoxifen or tamoxifen analog therapy. Assessment of ER(+) breast tumors or other ER(+) lesions with labeled DTPA-TX ligand prior to chemotherapy would provide a rational means of selecting patients for treatment with tamoxifen or tamoxifen analogues. Such selection of patients would permit more accurate evaluation of antiestrogens, since their use is limited to the patients with ER(+) lesions, who could potentially benefit from the drug.

EXAMPLE 31

Autoradiographic Studies of [111]IN-DTPA-TX in Breast Tumor-Bearing Rats

Female breast tumor-bearing rats (n=3) after receiving $^{111}$In-DTPA-TX (300 uCi, iv) were sacrificed at 30 min, 2, 4, 24 and 48 h. The body was fixed in carboxymethyl cellulose (4%) block. The frozen body was mounted to a cytostat (LKB 2250 cryo-microtome, Ijamsville, Md.) and 40 um coronal sections were made. The section was thawed and mounted on a slide. The slide was placed in contact with x-ray film (X-Omat AR, Kodak, Rochester, N.Y.) for 48 hours.

EXAMPLE 32

Gamma Scintigraphic Imaging of Estrogen Receptor Sites

Figure 2:
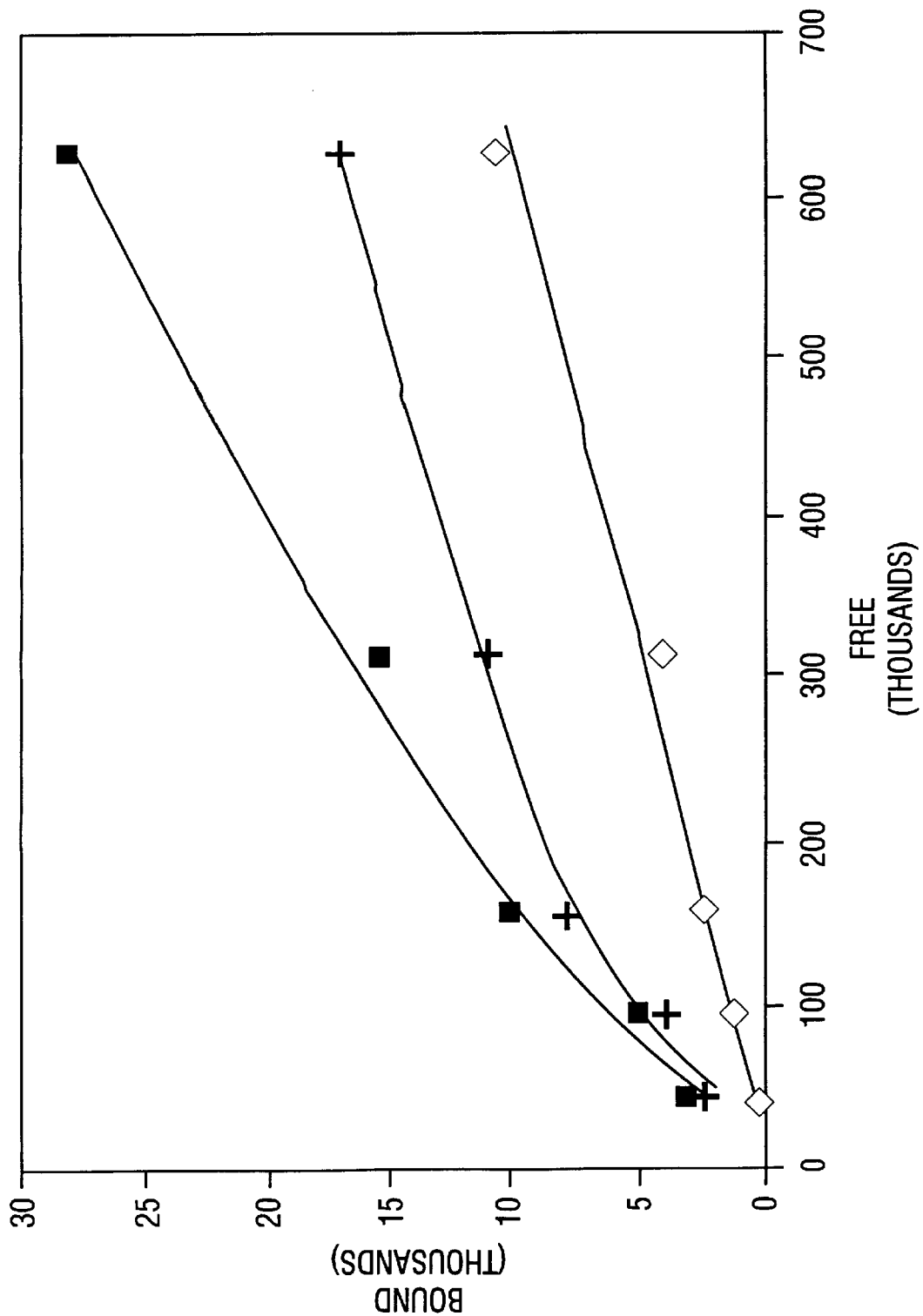
FIG. 2 Estrogen receptor saturation experiment measuring findings in pig uterus in vitro. This is to determine the nature of estradiol interaction with the estrogen receptor site.

In gamma scintigraphic imaging studies with [111I]ITX, the rabbit uterus showed increased uptake of [131I]ITX 24 hours postinjection (FIG. 2). This increased uptake can be blocked by pretreatment of the rabbit with DES, suggesting the uptake in the uterus is via an ER-mediated process. The uterus:muscle and uterus:background uptake ratios were 4.6 and 9.6,1 respectively.

The present study demonstrates that rabbit uterus uptake of [131I]ITX can be blocked by pretreatment with DES, suggesting the uptake in uterus is via an ER-mediated process.

TABLE 20

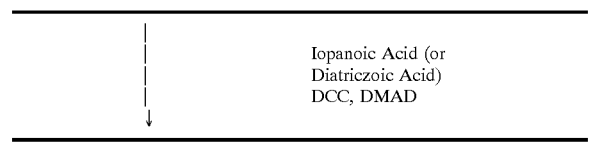

It is also contemplated that the amino tamoxifen derivatives will be useful for therapeutic purposes, for example in the therapy of estrogen receptors positive tumors, such as mammary tumors, and other estrogen receptor positive cancers. The amino tamoxifen derivatives may also be used conjugated with microcapsules, particularly conjugated to the surface of microcapsules, to provide a superior therapeutic agent having enhanced estrogen receptor rich tissue targeting capacity. In this regard, it is contemplated that the amino tamoxifen of the invention, and derivatives thereof, may be successfully conjugated to the surface of microcapsules, thereby also potentially providing a superior sustained release biopharmaceutical for in vivo use. $IC_{50}$ data generated with this conjugate (TX-NH-PBLG) is provided in Table 17.

TABLE 21

| Effect of Tamoxifen Analogues on Estrogen Receptor Binding (n = 9/analogue) | | | |
| --- | --- | --- | --- |
| Compound | $IC_{50}$ (M) | RBA | $K_i$ |
| Tamoxifen (TX) | $3 \times 10^{-5}$ | 100 | 15,000 |
| TX-$N_3$ (trans) | $3.8 \times 10^{-5}$ | 80 | 18,750 |
| TX-$NH_2$ (trans) | $3 \times 10^{-4}$ | 10 | 150,000 |
| TX-PBLG | $3 \times 10^{-4}$ | 10 | 150,000 |

°TX-PBLG (50 mg, MW. 50,000), prepared in DMSO (5 ml)
°RBA: relative finding affinity
°Studies used [3H] estradiol (5 nM)

The following flow chart demonstrates the basic chemical synthesis of amino tamoxifen derivatives of the present invention together with potential uses thereof:

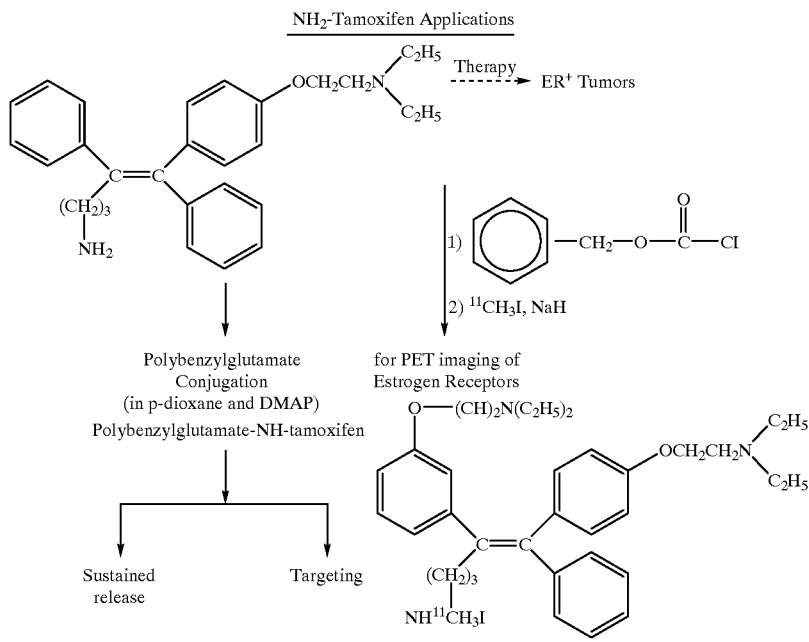

EXAMPLE 33

Use of Indium DTPA-Tamoxifen in MRI Analysis and in Combination with Vitamin A The present example outlines the use of the present invention for use in magnetic resonance imaging (MRI). The particular tamoxifen derivatives described here that useful for this application are not radioactive, i.e., they constitute "cold" labels, and are therefore particularly well suited for use in conjunction with the invention.

Figure 41:
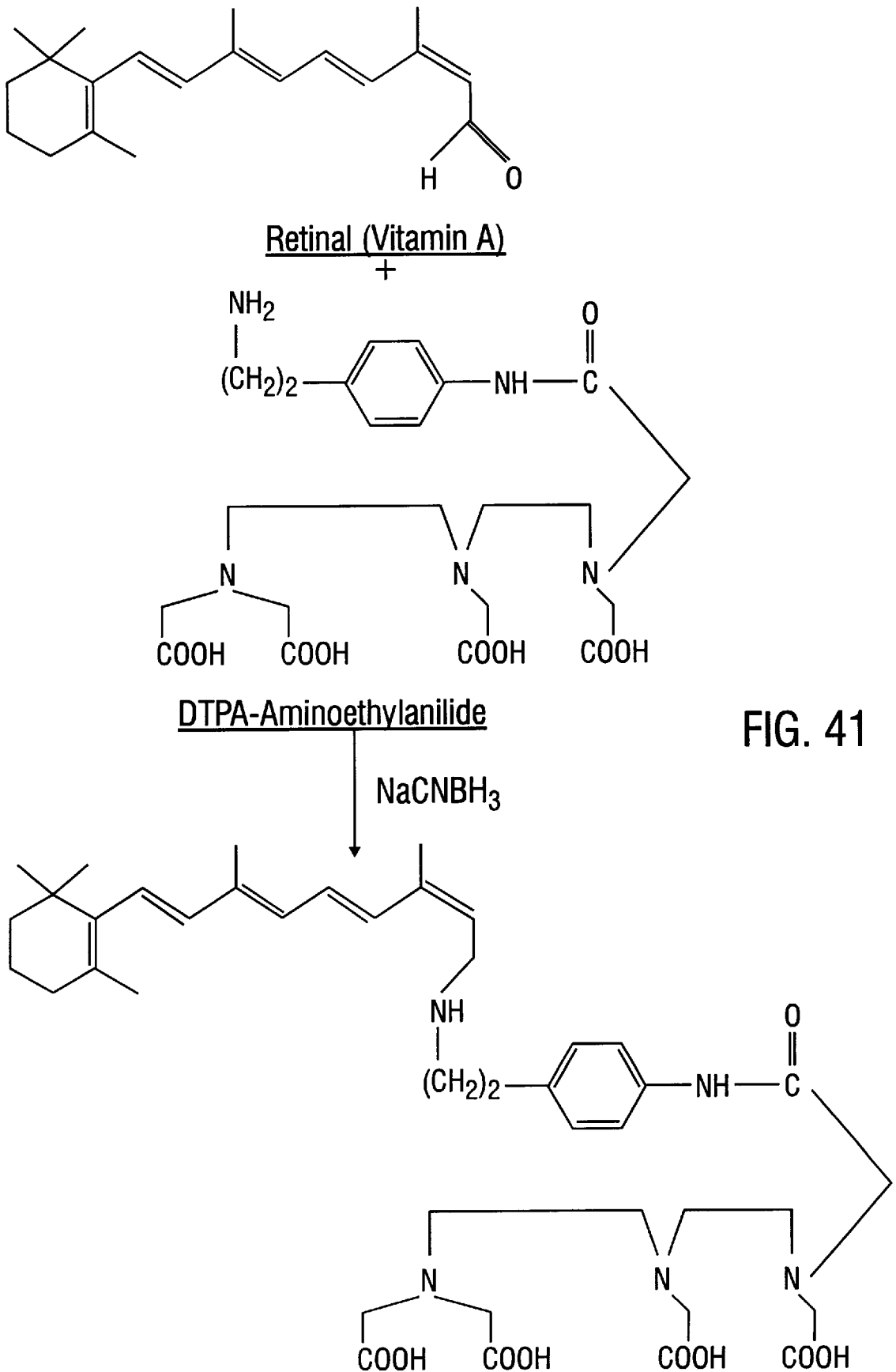
Figure 42B:
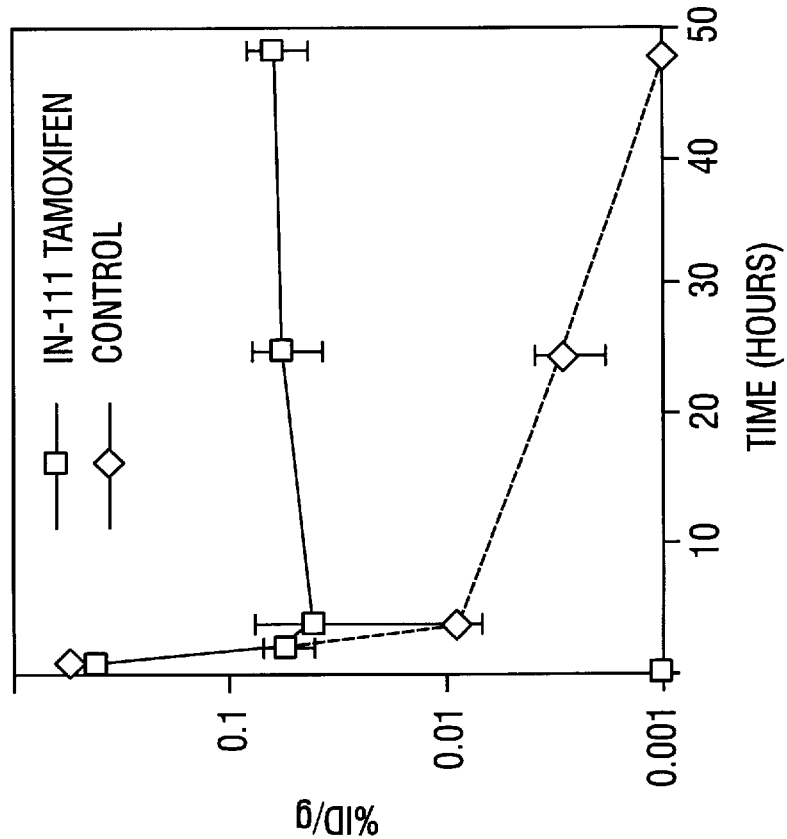
Figure 42A:
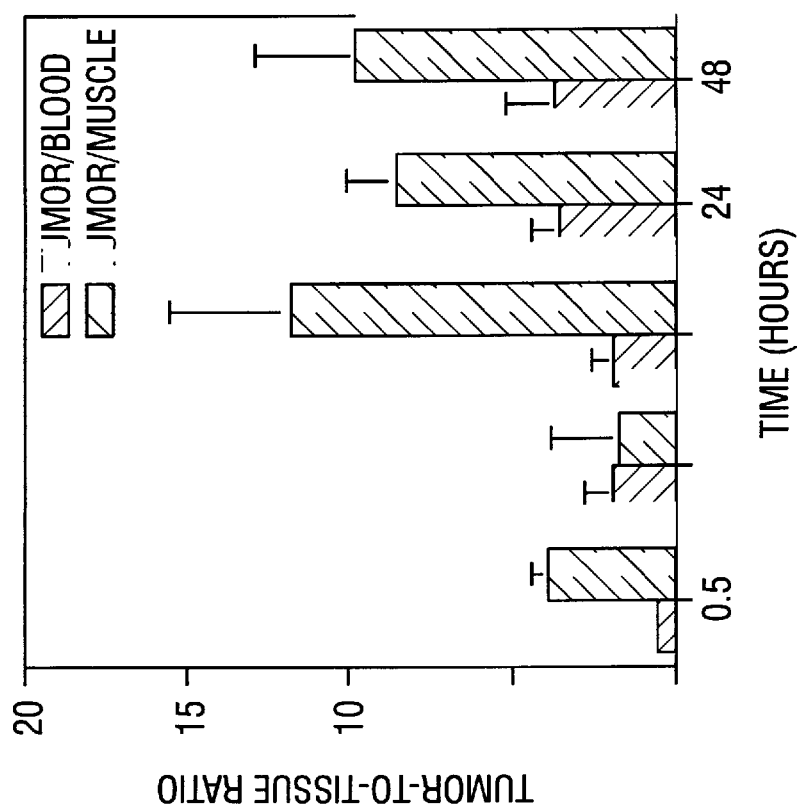
Figure 43C:
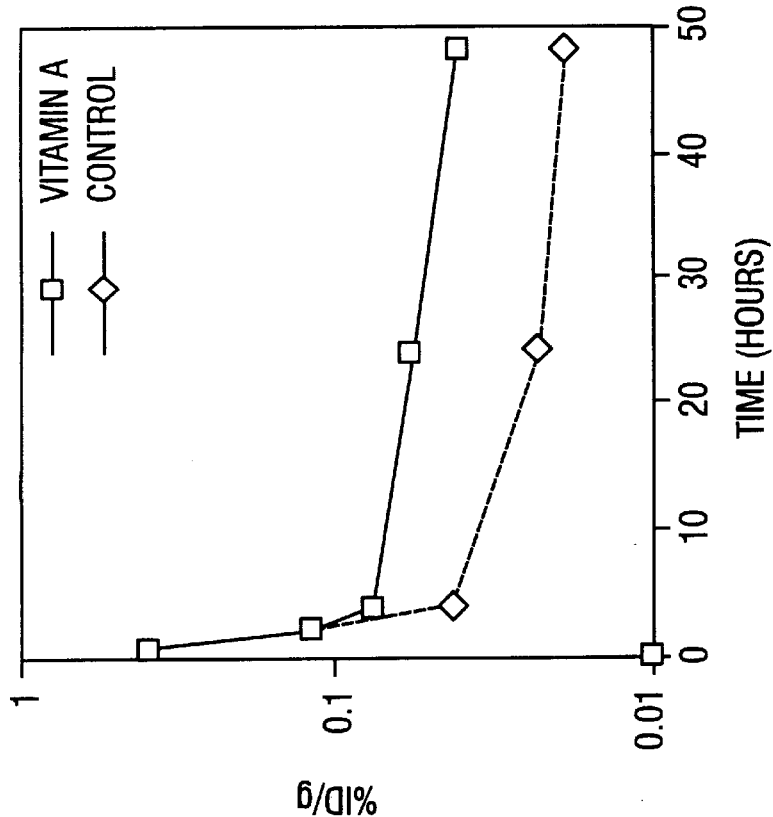
Figure 43B:
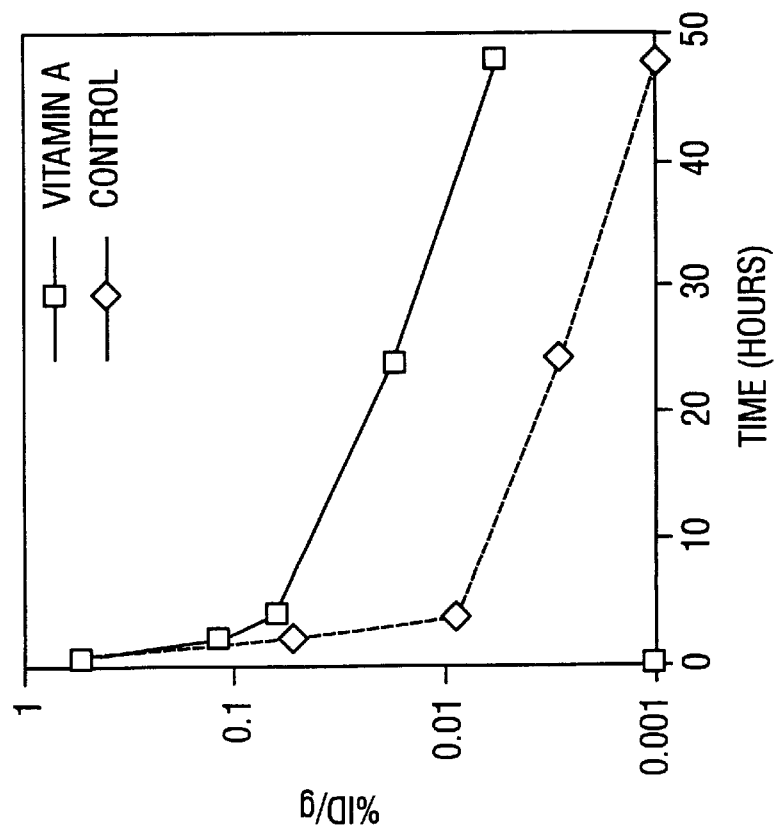
Figure 44A:
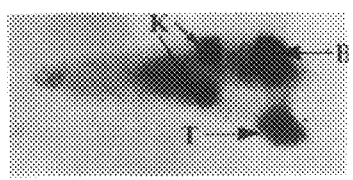
FIGS. 44A, 44B, 44C, 44D, 44E, $^{111}$In-DTPA-TX δ-scintigraphy. Anterior view of breast tumor-bearing rats receiving $^{111}$In-DTPA (300 μCi, i.v.) showed increased uptake in the tumors as a function of time at 30 min (44A), 2 hrs. (44B), 4 hrs. (44C), 24 hrs. (44C), and 48 hrs. (44D). T=Tumor, B=Bladder, L=Liver, K=Kidneys.
Figure 44B:
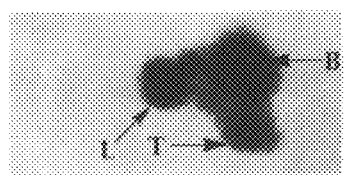
Figure 44C:
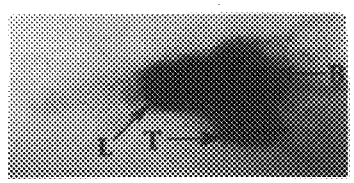
Figure 44D:
Figure 44E:
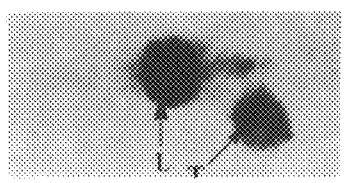
Figure 45A:
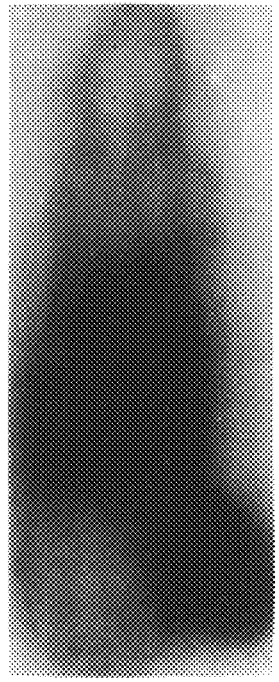
FIGS. 45A, 45B, and 45C Planar scintigraphy and auto radiography of $^{111}$In-DTPA-tamoxifen conjugate. $^{111}$In-DTPA-TX autoradiograms (breast tumor-bearing rats (300 μCi/rat, i.v.).
Figure 45B:
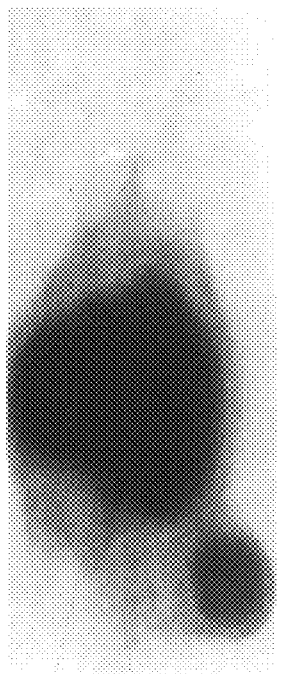
Figure 45C:
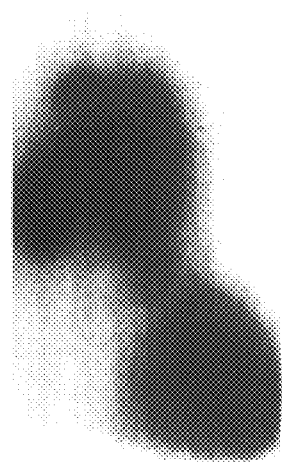
Figure 46A:
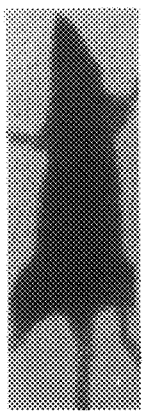
FIGS. 46A (30 min) 46B (2 hrs.), 46C (4 hrs.), 46D (24 hrs.), and 46E (48 hrs.) demonstrate the increase in uptake of $^{111}$In-DTPA retinal (200 μCi, i.v.) in breast tumor-bearing rats as a function of time. ($^{111}$In-DTPA-retinal-δ scintigraphy.)
Figure 46B:
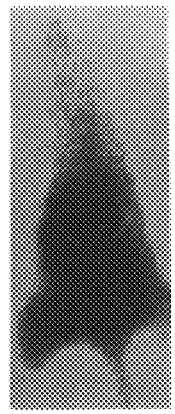
Figure 46C:
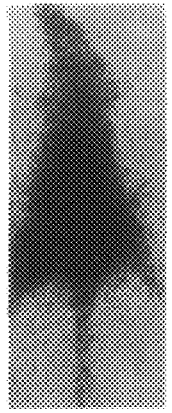
Figure 46D:
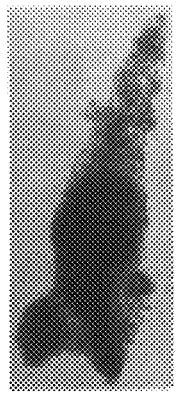
Figure 46E:
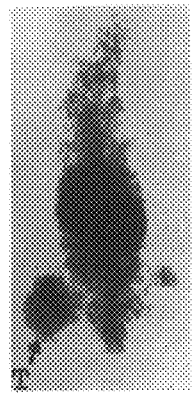
Figure 47A:
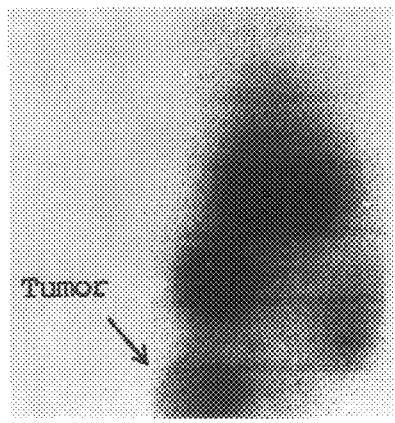
FIGS. 47A (4 hrs.) and 47B (24 hrs.) Planar scintigraphy and autoradiography of $^{111}$In-DTPA-vitamin A conjugate. Breast tumor-bearing rats injected with 200 μCi/rat, i.v., with the conjugate.
Figure 47B:
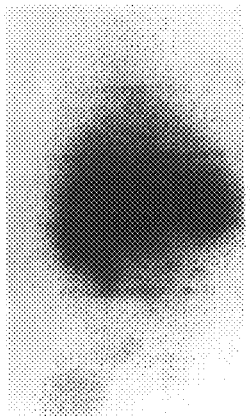
Figure 48:
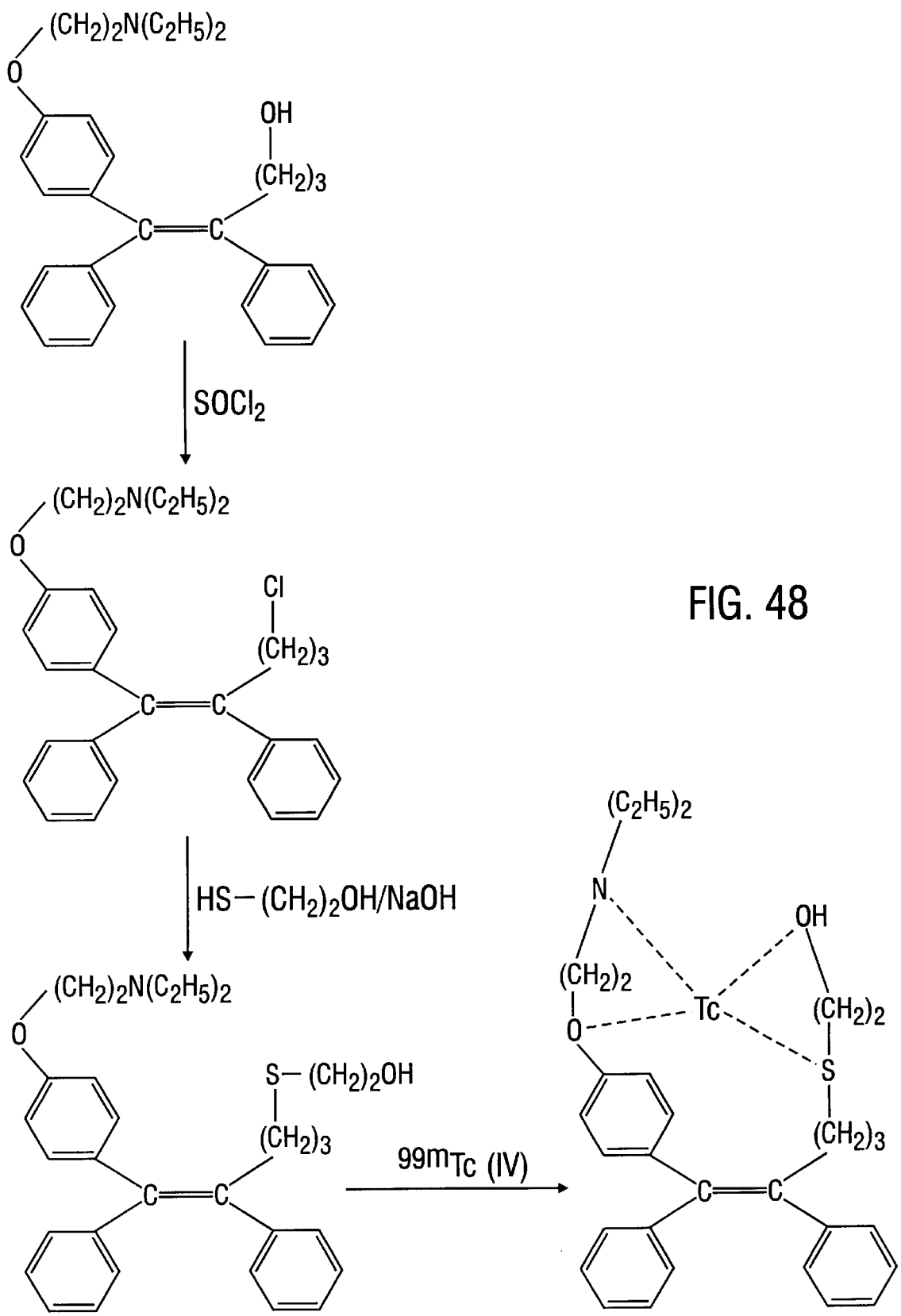
Figure 49A:
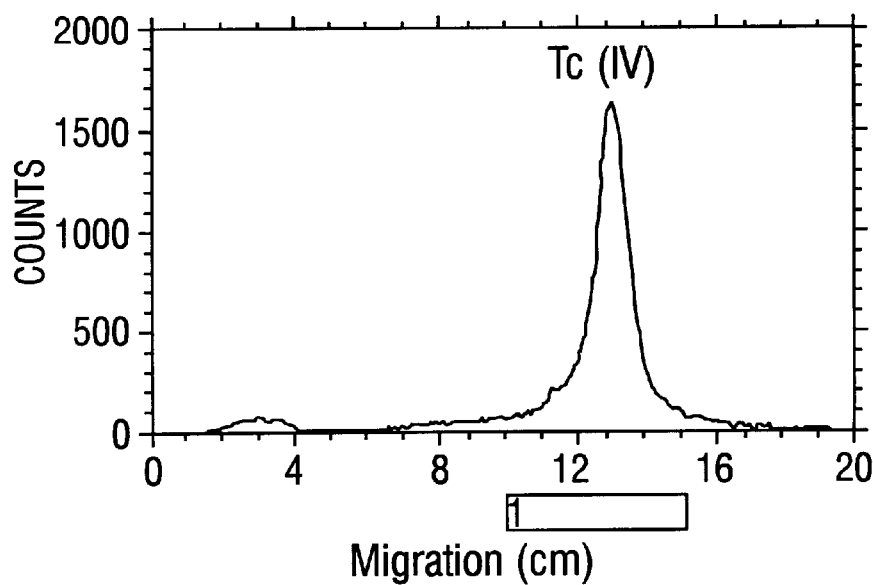
FIGS. 49A, 49B and 49C $^1$H-NMR of cis and trans products of tamoxifen.
Figure 49B:
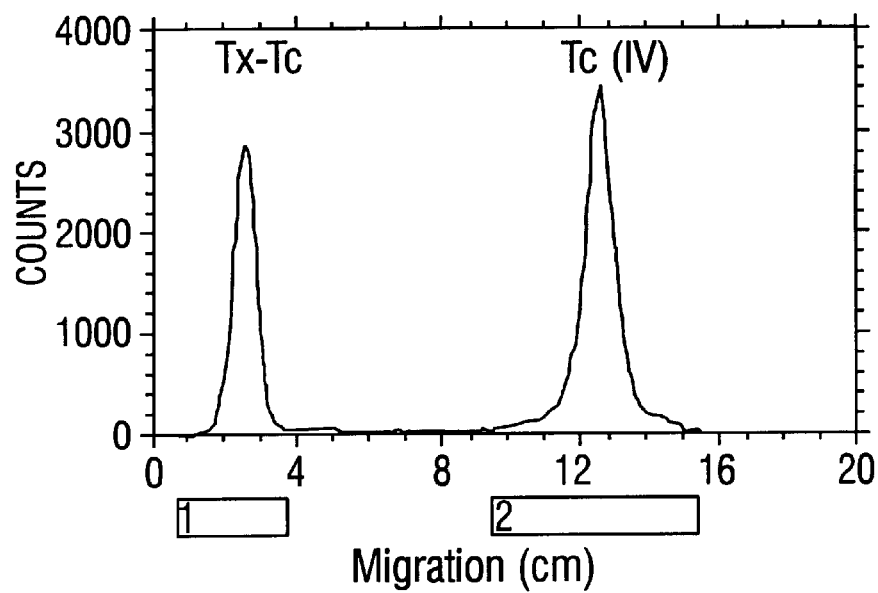
Figure 49C:
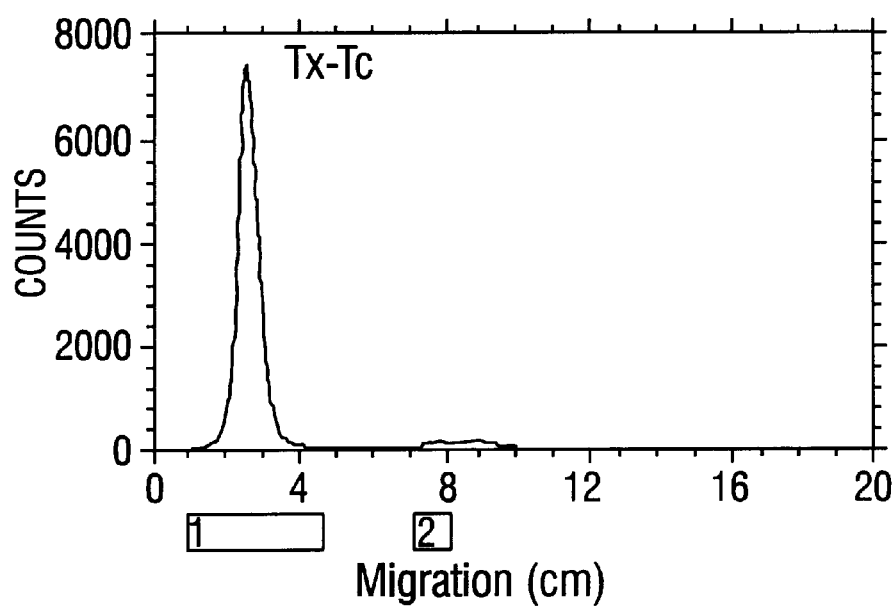

The present derivatives may be used in conjunction with Vitamin A. An outline for the synthesis of DTPA-Vitamin A conjugate is provided in FIG. 41. Increasing the ethyl chain of tamoxifen by one carbon with halogens attached produced superior affinities and greater potencies compared with tamoxifen. At the same halogen position, an aldehyde group was attached.

This aldotamoxifen derivative was conjugated to aminoethylanilide-DTPA, followed by sodium cyanoborohydride reduction yielded a water soluble DTPA-tamoxifen conjugate. Using the similar approach, DTPA-Vitamin A was prepared by treating retinal with aminoethylanilide-DTPA, followed by reduction reaction. Both conjugates were structurally proven by $^1$H-nuclear magnetic resonance (NMR) $^{13}$C-NMR, High Pressure Liquid Chromatograph (HPLC) and Mass Spectrometry.

Both conjugates could be easily labeled with $^{111}$In. Biodistribution of both conjugates indicated that tumor-to-blood and tumor-to-muscle ratios increased as a function of time (Tables 1 and 2). The unconjugated DTPA (control group) has faster blood clearance and less tumor-to-tissue uptake ratios compared with DTPA-Tamoxifen and DTPA-Vitamin A conjugates (shown in FIG. 1 and FIG. 2). Planar scintigraphy and autoradiography of both conjugates showed that tumor uptake remained steady throughout the time periods (images shown in FIG. 3 and FIG. 4). The present data indicated that both conjugates can detect ER(+) breast tumors, therefore, both conjugates should have potential use in monitoring treatment of breast cancer therapy with Tamoxifen and Vitamin A.

Aim and Method of Study

The objective of the proposed study is to improve the diagnosis, prognosis, and the planning and monitoring of the treatment of breast cancer. To accomplish this goal, a mixture of DTPA-tamoxifen and DTPA-Vitamin A (cocktail mixture) for imaging and therapy of breast tumors was used.

The following uses of the DTPA-TX constitute other embodiments of the present invention:

1. Synthesize water-soluble DTPA-tamoxifen conjugate and DTPA-Vitamin A conjugate.
2. Non-invasively identify the diagnostic potential of $^{111}$In-labeled DTPA-tamoxifen, DTPA-Vitamin A and the mixture of DTPA-tamoxifen/DTPA-Vitamin A (cocktail mixture) by planar scintigraphy.
3. Evaluation of the therapeutic response of DTPA-tamoxifen, DTPA-Vitamin A and the cocktail mixture in breast cancer animal model.
4. Correlating the tumor estrogen-receptor density determined by receptor assay with $^{111}$In-labeled cocktail mixture uptake before and after the cocktail mixture therapy of breast cancer.

The detection and measurement of estrogen receptor positive tumors and the rate of lipid peroxidation by the use of radiolabeled cocktail mixture should provide a useful tool for the detection of primary and secondary tumors. It is proposed for selecting and following the most favorable choice of tamoxifen and Vitamin A therapy and predict its outcome. The present invention and methods demonstrate the binding of a cocktail mixture to tumors and the detection of same with SPECT. Such an agent will be used to predict the response of tamoxifen and Vitamin A therapy for breast cancer. Such a cocktail mixture will also be used in methods for determining the causes behind occasional failure of tamoxifen therapy when indicators are ER-positive thus providing yet a further screening method. Also, the combination of tamoxifen and Vitamin A are proposed for suppressing the breast tumor cell growth, as both compounds actively inhibit tumor cell proliferation.

Radiohalogenated tamoxifen can non-invasively detect ER (+) lesions, yet the labeling procedure is complex and time consuming. DTPA-tamoxifen and DTPA-Vitamin A analogues have been developed, and these compounds are mixed in saline and labeled with $^{111}$In for SPECT evaluation of breast cancer. The data provided here illustrates a basis for the presently unproved method for the diagnosis and monitoring of the treatment of breast cancer through the application of a new cocktail mixture.

Tumor/blood ratio ranged from 0.11 to 0.07. Tumor/muscle ratio ranged from 5.68 to 7.38. Biodistribution of $^{131}$I-TX at 1, 3, 6 and 24 hrs showed a tumor uptake value 0.18±0.062, 0.23±0.152, 0.26±0.166 and 0.27±0.016. When rats primed with estradiol (60 μg/rat, 3 days, s.c.), the value changed to 0.30±0.033, 0.42± to 0.039, 0.48±0.107, and 0.40±0.123. Tumor/blood ratio ranged from 1.95 to 11.0. When rats pretreated with DES (1.2 mg/rat, iv), the tumor uptake value changed to 0.32±0.058 ($^{99m}$Tc-TX, 2 h) and

TABLE A

Biodistribution of $^{111}$In-DTPA Tamoxifen in Breast-Tumor-Bearing Rats*

|        | 30 min         | 2 hr           | 4 hr           | 24 hr          | 48 hr          |
|--------|----------------|----------------|----------------|----------------|----------------|
| Blood  | 0.439 ± 0.40   | 0.057 ± 0.015  | 0.043 ± 0.036  | 0.060 ± 0.021  | 0.067 ± 0.021  |
| Heart  | 0.166 ± 0.010  | 0.025 ± 0.005  | 0.022 ± 0.013  | 0.054 ± 0.022  | 0.044 ± 0.004  |
| Lung   | 0.368 ± 0.117  | 0.063 ± 0.037  | 0.037 ± 0.027  | 0.126 ± 0.023  | 0.125 ± 0.011  |
| Liver  | 0.421 ± 0.037  | 0.464 ± 0.075  | 0.339 ± 0.017  | 3.009 ± 0.750  | 2.192 ± 0.392  |
| Kidney | 1.262 ± 0.042  | 0.550 ± 0.153  | 0.545 ± 0.208  | 3.076 ± 0.461  | 3.243 ± 0.397  |
| Uterus | 0.704 ± 0.636  | 0.540 ± 0.351  | 0.064 ± 0.056  | 0.200 ± 0.037  | 0.233 ± 0.008  |
| Muscle | 0.255 ± 0.261  | 0.118 ± 0.086  | 0.009 ± 0.009  | 0.025 ± 0.009  | 0.026 ± 0.003  |
| Tumor  | 0.300 ± 0.030  | 0.109 ± 0.058  | 0.089 ± 0.054  | 0.204 ± 0.043  | 0.236 ± 0.069  |
| Bone   | 0.108 ± 0.012  | 0.795 ± 1.230  | 0.047 ± 0.058  | 0.089 ± 0.006  | 0.141 ± 0.077  |
| Urine  | 194.362 (n = 1)| 172.59 ± 35.7  | 47.39 ± 11.65  | 0.752 ± 0.218  | 0.476 ± 9.352  |

*Each rat received $^{111}$In-DTPA-tamoxifen (10 μCi, iv). Each value is percent of injected dose per gram weight (n = 3)/time interval. Each data represents means of three measurements with standard deviation.

TABLE B

Biodistribution of $^{111}$In-DTPA Retinal in Breast-Tumor-Bearing Rats[1]
(Percent of Injected Dose Per Gram Weight; N = 3/Time Interval)

|           | 30 min         | 2 hr           | 4 hr           | 24 hr          | 48 hr          |
|-----------|----------------|----------------|----------------|----------------|----------------|
| Blood     | 0.658 ± 0.099  | 0.117 ± 0.026  | 0.065 ± 0.005  | 0.018 ± 0.004  | 0.007 ± 0.000  |
| Brain     | 0.020 ± 0.001  | 0.008 ± 0.001  | 0.005 ± 0.001  | 0.002 ± 0.000  | 0.001 ± 0.001  |
| Heart     | 0.178 ± 0.035  | 0.049 ± 0.011  | 0.030 ± 0.001  | 0.018 ± 0.001  | 0.014 ± 0.001  |
| Lung      | 0.418 ± 0.098  | 0.122 ± 0.024  | 0.066 ± 0.008  | 0.042 ± 0.012  | 0.035 ± 0.007  |
| Liver     | 0.225 ± 0.055  | 0.097 ± 0.023  | 0.066 ± 0.003  | 0.065 ± 0.008  | 0.061 ± 0.005  |
| Spleen    | 0.135 ± 0.030  | 0.067 ± 0.012  | 0.058 ± 0.005  | 0.066 ± 0.011  | 0.056 ± 0.009  |
| Kidney    | 1.884 ± 0.188  | 1.119 ± 0.186  | 0.883 ± 0.035  | 0.710 ± 0.021  | 0.628 ± 0.059  |
| Intestine | 0.302 ± 0.107  | 0.098 ± 0.004  | 0.052 ± 0.006  | 0.035 ± 0.005  | 0.024 ± 0.005  |
| Uterus    | 0.573 ± 0.011  | 0.169 ± 0.018  | 0.097 ± 0.019  | 0.086 ± 0.016  | 0.098 ± 0.013  |
| Muscle    | 0.097 ± 0.007  | 0.022 ± 0.005  | 0.012 ± 0.000  | 0.012 ± 0.004  | 0.007 ± 0.001  |
| Tumor     | 0.393 ± 0.050  | 0.120 ± 0.026  | 0.078 ± 0.007  | 0.060 ± 0.005  | 0.043 ± 0.002  |
| Bone      | 0.161 ± 0.032  | 0.055 ± 0.008  | 0.034 ± 0.006  | 0.031 ± 0.007  | 0.028 ± 0.003  |
| Urine     | 168.98 (n = 1) | 9.64 (n = 1)   |                | 0.030 (n = 1)  | 0.016 ± 0.004  |

[1]Each rat received $^{111}$In-DTPA-retinal (10 μCi, iv).

EXAMPLE 34

$^{99m}$TC-Labeled Tamoxifen Analog

The present example is provided to demonstrate the preparation and use of a class of SPECT ligands. These ligands may be used, for example, in the imaging of breast tumors, particularly estrogen receptor positive breast tumors.

$^{99m}$TC-labeled tamoxifen (TX) analogue was prepared by reacting hydroxyethylthio TX analogue with reduced Tc-IV. The yield was 50–60% (purity >99%). $^{131}$I-TX was prepared by treating tosyl-TX with Na$^{131}$I. The yield was 20–25% (>99% purity). Biodistribution studies of both analogues were performed in DMBA-induced mammary tumor-bearing rats (10 μCi/rat, i.v., n=3/time interval). Biodistribution $^{99m}$Tc-TX at 1, 2, 4, 6 and 18 hrs showed a tumor uptake value (% injected dose/gram tissue) of 0.37±0.058, 0.38±0.066, 0.27±0.041, 0.28±0.124 and 0.10±0.013.

0.22±0.059 ($^{131}$I-TX, 6 h). In rats pretreated with estradiol, a significant increase in tumor uptake value was observed after $^{131}$I-TX postinjection. $^{99m}$Tc-TX uptake in tumor could not be blocked by DES, suggesting the uptake was not due to a receptor-mediated process. $^{131}$I-TX may be useful in differentiating functioning ER(+) breast tumors.

Using clomiphene, a three step-process was used; to hydroxytamoxifen, then tosyl tamoxifen, and eventually to a halogenated tamoxifen. Eight cis and trans isomers of halogenated tamoxifen analogues were then prepared. In the NMR for the cis form and the trans form, there are subtle differences in the aromatic portion of the molecules, while the aliphatic portion is virtually the same. In testing these two, their killing power on human breast tumor cells as well as their binding power was compared. Using MCF-7 cells incubated for 72 hr, they were subjected to the new compound and its ability to reduce growth by 50% was measured using MTT tetrazolium dye assay. Eight new compounds were superior in killing power to tamoxifen itself; the bromo, for example, had almost 25 times the killing power of tamoxifen. By using pig uterine cytosol, it was noted that the halogenated tamoxifen had a better binding affinity than tamoxifen itself. Bromotamoxifen was 150 times better than tamoxifen and fluorotamoxifen had a binding power 30 times that of tamoxifen.

The toxicity of the different tamoxifens were relatively atoxic. Iodotamoxifen was slightly more toxic than some of the others, but the dosage was 50 mg/kg before there was any toxicity at all. The toxicity of fluorotamoxifen seems minimal, since doses as high as 200 mg/kg were well tolerated. In comparison, the usual human dose of 10–20 mg twice a day for tamoxifen is far smaller than that readily tolerated by the animal.

Of these eight different agents, fluorotamoxifen was pursued for its killing and binding power. This technology was used as PET imaging agent. Using the PET camera, the uterus of a pig was defined. The fluorotamoxifen was then administered, and a configuration was noted that was much like what was seen in the anatomical specimen, with the uterus and the fallopian-tube-ovarian complex. From the cross-sectional configuration as well, it appears that fluorotamoxifen can be used as an imaging agent. Administration of tamoxifen, or diethylstilbestrol (DES), the uptake in the target organ could be blocked.

As a breast tumor model, a rat with deposition of ER(+) tumor cells (NF13762 cell line) in the flank was used. In utilizing fluorotamoxifen, uptake was observed within the uterus as well as the tumor in the flank. Thus, a fluorinated tamoxifen which can readily visualize estrogen receptor sites, even in the implanted neoplasm is revealed. In studying the distribution, good uptake in the tumor and other sites, in the brain and in the liver were noted. Good biodistribution in the uterus/blood ratio was also observed. The uteri:blood ratio was 13.5 and could be blocked somewhat by any of the estrogens or by tamoxifen itself. Fluorotamoxifen can be prepared as an analog of tamoxifen itself with high specific activity, and it can also be prepared so that it will demonstrate a positive estrogen receptor site in the test animal.

Other agents were also synthesized which would be helpful as diagnostic agents to demonstrate estrogen receptor activity. The synthesis of iodotamoxifen, which could be used in SPECT camera, was achieved. A sulfhydrytamoxifen was also processed, to which was attached technetium (t½=6 hours) to provide another agent effective in imaging with SPECT camera. Both ligands may also be useful in predicting the response of tamoxifen analog therapy and tumor targeting (screening method). In addition, such ligands will be useful in determining the causes behind occasional failure of tamoxifen therapy when biopsy indicators are ER-positive.

Synthesis of Hydroxyethylmercaptometyl-N-, N-diethyltamoxifen

Cis or trans chloro analogue of tamoxifen (0.213 g, 0.476 mmol)[8] dissolved in dimethylformamide (DMF, 25 ml) was added NaH (17 mg, 0.57 mmol) and mercaptoethanol (44.5 mg, 0.57 mmol). The reaction was heated at 80° C. for 2 h. DMF was then distilled and $CHCl_3$ (50 ml) was added. The mixture was washed with water (4×20 ml). The $CHCl_3$ layer was dried over $MgSO_4$, filtered and evaporated to dryness. The crude product was reconstituted in $CHCl_3$, loaded on a silica gel packed column and eluted with 10% triethylamine in ether:petroleum ether (1:1). The product was isolated, cis (200 mg, 86.2%) or trans (150 mg, 64.7%). $M^+=489$ (cis), $^1$H-NMR of cis and trans products are shown in FIG. 1. Anal. Cis ($C_{31}H_{39}NO_2S.½H_2O$) C, H, N, S, Calc. C: 73.34, H: 8.14, N: 2.76, S: 6.30; Found: 74.12, H: 7.70, N: 2.72, S: 5.77.

Radiolabeling of Hydroexyethylmercapto Analogue of Tamoxifen

Hydroxyethylmercapto analogue of tamoxifen (1 mg) was dissolved in acetone (1 ml). $^{99m}$Tc-IV (reduced with HCL)[12] (3 mCi) was added and the reaction was reacted at 100° C. for 1 hr. After evaporation of acetone, the mixture was reconstituted in $CH_2Cl_2$ (1 ml). Excess water washing (5×1 ml) was used to remove free $^{99m}$Tc-IV. The $CH_2Cl_2$-layer was dried over $MgSO_4$ and evaporated to dryness. The pure product (1 mCi) was reconstituted in 10% EtOH (5 ml). (The proposed synthetic scheme of $^{99m}$Tc-tamoxifen is shown in FIG. 2). Three TLC solvent systems were used to prove the product. These systems are acetone, saline and ether:petroleum ether:triethylamine (PET) (1:1:10%). All free $^{99m}$Tc will migrate to solvent front in these systems, however, $^{99m}$Tc-labeled product remains at origin. FIG. 46 showed the radio-TLC analysis of the product (eluted with saline). The product isolated ranges from 20–40% yield.

Synthesis of $^{131}$I-Iodo Analogue of Tamoxifen

Tosyl analogue of tamoxifen (10 mg) was dissolved in acetone (1 ml). Na$^{131}$I (3.15 mCi in 0.2 ml borate buffer, pH 8.5) was added. The reaction mixture was heated at 100° C. for 2 h. Acetone was then evaporated under $N_2$. The unreacted tosyl analogue was hydrolyzed with 2N HCl (1 ml) at 110° C. for 15 minutes. The mixture was basified with 2N NaOH (1.5 ml). The product was extracted from $CH_2Cl_2$ (2 ml) and purified from a silica gel packed column (SPE 500 mg, Waters, Clifton, N.J.). The column was eluted with 10% triethylamine in ether:petroleum ether (1:1). The solvent was evaporated and the final product was reconstituted in 0.05 M citric acid (10 ml). The product isolated was 690 μCi. Radio-thin layer chromatogram indicated one peak which corresponded to unlabeled iodo analogue of tamoxifen with Rf=0.65 from 10% triethylamine in ether:petroleum ether (1:1).

Biodistribution of $^{131}$I-iodotamoxifen in Tumor-Bearing Rats

Female Fisher 344 rats (250–275 g) (Harlan, Inc., Indianapolis, Ind.) were inoculated with mammary tumor cells using the 13762 tumor cell line (s.c. $10^5$ cells/rat). After 14 days, a tumor size of 1–2 cm was observed. For $^{131}$I-ITX studies, five groups of rats (N=3/group) were anesthetized with ketamine (10–15 mg/rat). The trans $^{131}$I-ITX was given to four of the five groups (8.9 μCi/rat, i.v.) and biodistribution was studied at 1, 3, 6 and 24 h intervals. In blocking studies, the fifth group of rats was given diethylstilbestrol (DES) (1.2 mg/rat) for 1 h, followed by 8.9 μCi of $^{131}$I-ITX; biodistribution was studied 6 h later. The tissues were collected at different time intervals. The tissues were weighted and counted for radioactivity. The percent of injected dose per gram of tissue weight was calculated.

Biodistribution of $^{131}$I-ITX in Mammary Tumor-Bearing Rats Primed with Estradiol Four groups of tumor-bearing rats (N=3/group) primed with estradiol (60 μg, s.c., 3 days) were given $^{131}$I-ITX (10 μCi/rat, iv). The biodistribution studies were conducted at 1, 3, 6 and 24 h.

Biodistribution of $^{99m}$Tc-Sulfhydratamoxifen ($^{99m}$Tc-TX) in Mammary Tumor-Bearing Rats Six groups of rats (N=3/group) were anesthetized with ketamine. $^{99m}$Tc-TX was given to five of the six groups (10 μCi/rat, iv) and biodistribution was studied 1, 2, 4, 6 and 18 hrs. In blocking studies the sixth group of rats was given DES (1.2 mg/rat) for 1 h, followed by $^{99m}$Tc-TX; biodistribution was studies 2 hrs later. The tissues were collected at different time intervals. The percent of injected dose per gram of tissue weight was determined.

Estrogen Receptor Assay of Mammary Tumors

To ascertain whether 13762-cell-line-induced tumors in rats were estrogen-receptor positive, a receptor assay was performed. Briefly, the tumor tissue (16 g) was dissected from 13762 mammary tumor-bearing female rats. The tissue was homogenized in Tris buffer (15 ml) as described and then centrifuged at 100,000 g to prepare a tumor tissue cytosol. This tissue cytosol was then pretreated with dextran-coated charcoal before the assay was performed. A saturation curve was obtained for [$^3$H]estradiol ($10^{-5}$–$10^{10}$M) in the presence and absence of estradiol ($10^{-5}$M). Scatchard analysis was performed to determine the receptor affinity and density. Protein concentrations were determined according to the method of Lowry et al.[12]

Imaging Studies

A group of rats (N=4) were administered with $^{99m}$Tc-TX (300 μCi, iv). The planar image was performed with a gamma camera (Iso Graphics Inc., Atlanta, Ga.). The camera was connected with a computer (ADAC System 1). A high resolution collimator (140 KeV Nuclear Chicago) was used. Each rat was positioned supine in the camera. After each rat received $^{99m}$Tc-TX, eight 15-minute consecutive images were acquired. The acquisition time for each image was 5 minutes.

Results

Radiosynthesis

Following standard procedures,[14] the [$^{13}$I]ITX was prepared in a 20–25% yield (decay corrected) and the $^{99m}$Tc-TX was prepared in 20–40%. I-131 radiolabeled compound could be resolved from the unlabeled reaction mixture components with very little difficulty, giving a high specific activity product in a reasonable yield. The specific activity was determined based on UV absorbance (254 nm) and radioactivity detection of a sample of known mass and radioactivity. In this no-carrier-added synthesis, the specific activity for $^{131}$I-ITX was 1 to 2 Ci/μmol (radiochemical purity) >99%). Authentic non-radiolabeled ITX were co-injected to confirm the identity of the radiolabeled compounds. For $^{99m}$Tc-TX chelation, we observed that using the trans isomer of TX to chelate $^{99m}$Tc-IV was unstable during the purification process. Thus, only the cis-isomer of TX was used to chelate $^{99m}$Tc-IV and subsequently, the biodistribution studies were performed.

In Vivo Tissue Distribution Studies

The biodistribution of the [$^{131}$I]ITX in rats is shown in Tables 10 (Example 19) and Table 22.

TABLE 22

Biodistribution of $^{131}$I-Iodo Analogue of Tamoxifen in Tumor-Bearing Rats Primed with Estadiol[1]

| Tissue | 1 h | 3 h | 6 h | 24 h |
|---|---|---|---|---|
| Blood | 0.155 ± 0.0040 | 0.120 ± 0.0137 | 0.086 ± 0.0018 | 0.036 ± 0.0001 |
| Lung | 2.835 ± 0.1396 | 3.035 ± 0.4111 | 3.058 ± 0.4577 | 1.124 ± 0.2256 |
| Liver | 6.746 ± 0.0546 | 6.734 ± 0.1221 | 4.665 ± 0.4606 | 2.710 ± 0.5325 |
| Kidney | 1.301 ± 0.0839 | 1.493 ± 0.1071 | 1.386 ± 0.1157 | 0.573 ± 0.1542 |
| Uterus | 0.334 ± 0.0485 | 0.400 ± 0.1316 | 0.559 ± 0.0982* | 0.335 ± 0.0770 |
| Muscle | 0.214 ± 0.0176 | 0.242 ± 0.1869 | 0.253 ± 0.0208 | 0.114 ± 0.0248 |
| Tumor | 0.303 ± 0.0333* | 0.422 ± 0.0389* | 0.479 ± 0.1065* | 0.397 ± 0.1231 |

[1.]Rats were primed with estradiol for 3 days (60 μg/rat s.c.). On day 4, each rat was given $^{131}$I-ITX (10 μCi/rat).
[2.]P < 0.05 (t-test) when compared to mammary tumor-bearing rats not primed with estradiol at the corresponding time shown in Table 1.

The uptake of tumor-to-blood ratios increased as a function of time. At 24 h postinjection, the tumor uptake ratios were 0.267±0.0160 and 0.397±0.1231 (primed with estradiol). Thyroid uptake increased slightly which may not be a significant in vivo deiodination. In blocking studies, both tumor and uterus value were decreased in 6 h blocking group; when compared to 6 h non-blocking group; however, this was not a significant difference. Instead, priming tumor-bearing rats with estradiol can enhance the tumor uptake value at 1, 3 and 6 h (Table B). These findings suggest the tumor uptake of $^{131}$I-ITX is via a receptor-mediated process.

The biodistribution of the $^{99m}$Tc-TX in rats is shown in Table 23.

TABLE 23

Biodistribution of $^{99m}$Tc-Sulfhydraltamoxifen in
Mammary Tumor-Bearing Rats[1]
(Percent of Injected Dose per Gram Weight; N-3/Time Interval)

| Tissue | 1 h | 2 h | 2 h[2] | 4 h | 6 h | 18 h |
|---|---|---|---|---|---|---|
| Blood | 0.724 ± 0.205 | 0.551 ± 0.011 | 0.791 ± 0.113 | 0.400 ± 0.031 | 0.496 ± 0.275 | 0.243 ± 0.015 |
| Liver | 2.274 ± 0.068 | 1.927 ± 0.319 | 3.153 ± 0.537 | 1.378 ± 0.198 | 3.508 ± 0.672 | 1.988 ± 0.218 |
| Lung | 0.530 ± 0.107 | 0.446 ± 0.036 | 0.994 ± 0.230 | 0.317 ± 0.073 | 0.534 ± 0.258 | 0.254 ± 0.027 |
| Spleen | 2.365 ± 0.687 | 1.634 ± 0.222 | 2.235 ± 0.587 | 1.744 ± 0.586 | 3.417 ± 0.705 | 2.155 ± 0.735 |
| Kidney | 2.652 ± 0.082 | 2.799 ± 0.440 | 1.333 ± 0.296 | 3.664 ± 0.446 | 1.773 ± 0.220 | 2.395 ± 0.139 |
| Intestine | 1.535 ± 0.330 | 0.804 ± 0.085 | 1.986 ± 1.252 | 0.564 ± 0.053 | 0.891 ± 0.265 | 0.254 ± 0.039 |
| Stomach | 2.738 ± 0.370 | 1.655 ± 0.304 | 2.392 ± 0.630 | 1.565 ± 0.163 | 2.311 ± 0.745 | 0.689 ± 0.127 |
| Uterus | 0.304 ± 0.030 | 0.352 ± 0.036 | 0.411 ± 0.055 | 0.240 ± 0.056 | 0.331 ± 0.221 | 0.067 ± 0.015 |
| Muscle | 0.068 ± 0.017 | 0.113 ± 0.035 | 0.082 ± 0.006 | 0.047 ± 0.003 | 0.055 ± 0.043 | 0.014 ± 0.001 |
| Tumor | 0.371 ± 0.058 | 0.323 ± 0.058 | 0.383 ± 0.066 | 0.272 ± 0.041 | 0.279 ± 0.124 | 0.104 ± 0.013 |

[1]-13762 cell lines was inoculated to rats (s.c. 10,00 cells/rat). When tumor size reached 1–2 cm, each rat was administered 10 μCi tracer.
[2]-In blocking studies, each rat was pretreated with DES (1.2 mg i.v.) 1 h prior to giving tracer.

The tumor-to-blood ratio was in the range of 0.07–0.11 and the tumor-to-muscle ratio was in the range of 5–7 with the time interval studies. The tumor uptake value can not be blocked with DES, suggesting the $^{99m}$Tc-TX uptake in tumor is not via a receptor mediated process.

From the Scatchard analysis in the estrogen receptor assay,t he 13762-tumor-cell-induced tumors had an estrogen receptor density (Bmax) of 7.5 fmol/mg of cytosol protein and a receptor binding affinity (kd) of 33 nM. Estrogen receptor assay was performed according to previous reports. Protein concentrations were determined to be 400 μg/ml. In ER(+) breast cancer patients, estrogen receptor positivity was defined as equal to or greater than 10 fmol/mg cytosol protein. Levels between 5 and 10 were considered equivocal.

Imaging Studies

Figure 50:
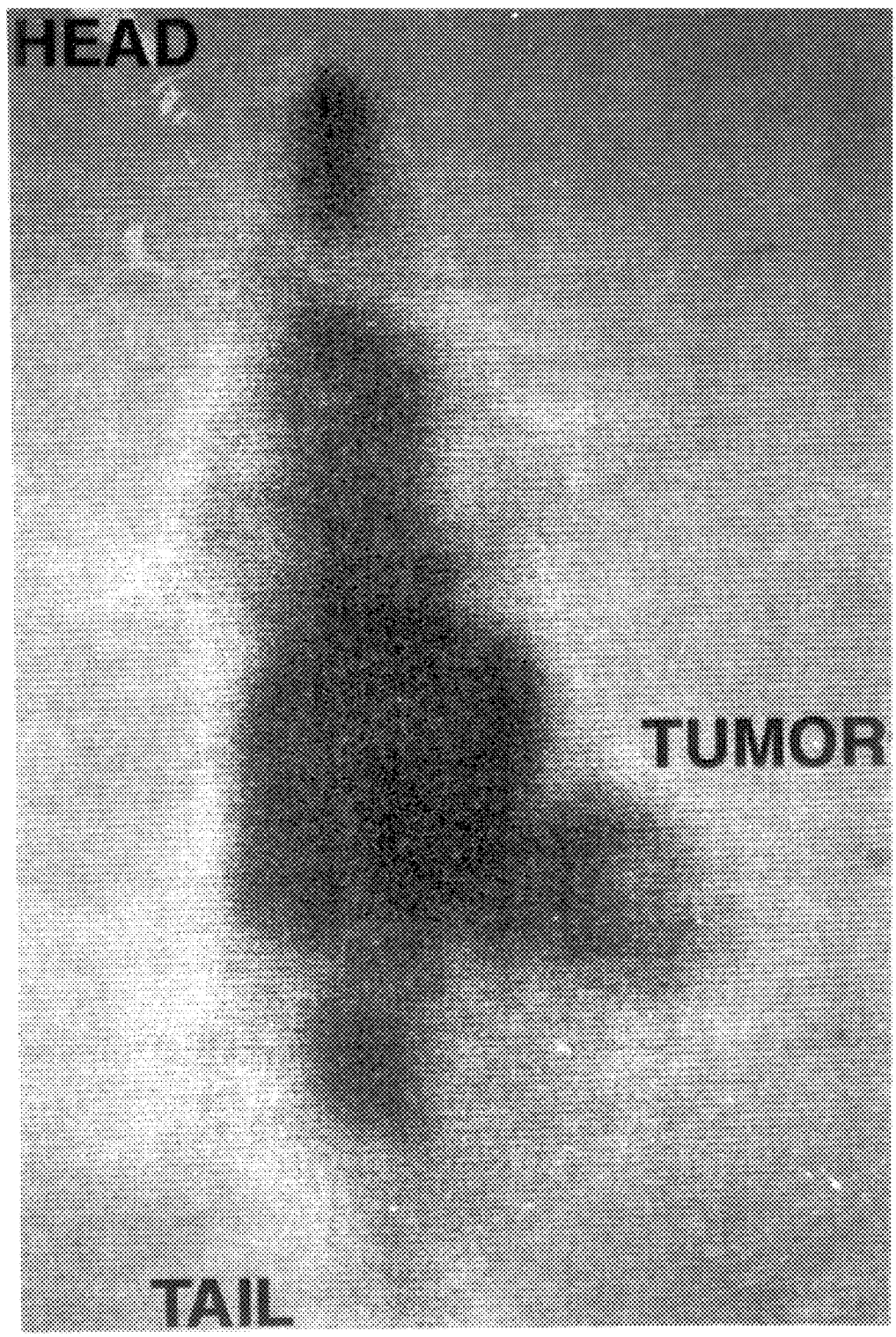
FIG. 50 shows an increased uptake of ITX by the stomach region of rats.

In in vivo gamma scintigraphy imaging studies, the tumor was visualized at 15 minutes to 2 hours postinjection. The stomach region of rats showed an increased uptake (shown in FIG. 50). Dissociation of $^{99m}$Tc from $^{99m}$Tc-TX might occur in vivo.

The tumor cell line used in the present study was originally derived from diemthylbenz[a]-anthracene (DMBA)-induced tumors. This chemical-induced tumor was reported to be estrogen receptor-positive. The present data support this finding.

Estradiol is very poorly water soluble material; thus, DES diphosphate is selected for $^{131}$I-ITX blocking studies. The blocking studies for $^{131}$I-ITX are not all that impressive, which could be due to the low estrogen receptor density in tumors and/or because of the possibility of endogenous estrogens which affects the results. However, priming older rats with estradiol can enhance the tumor uptake value. Data obtained from Table 21 and 22 support that ITX is lipophilic. ITX uptake in tumors may be rapidly distributed through blood flow within the first hours and may bind to tumor estrogen receptors as time increases. Thus, the tumor uptake of $^{131}$I-ITX is via an ER– mediated process. This analogue is useful in diagnosing breast tumors and imaging tumors with ERs (e.g., meningiomas).

$^{99m}$Tc-labeled tamoxifen analogue uptake in tumors was not blocked by pretreatment with DES. This finding suggests that $^{99m}$Tc-TX uptake in tumors is not via an ER-mediated process. Gamma scintigraphy of $^{99m}$Tc-Tx in tumor-bearing rats indicated that in vivo dissociation might occur.

$^{99m}$Tc and $^{131}$I-labeled analogues of tamoxifen have been prepared here and shown to be useful. In vivo biodistribution studies in mammary tumor-bearing rats suggest that I-131 labeled analogues of tamoxifen may be a good candidate for radiodiagnostic imaging of estrogen-responsive tissues.

EXAMPLE 35

Breast Cancer Therapy using Tamoxifen and Retinoic Acid

This study is designed to improve monitoring of breast cancer treatment. We will develop $^{111}$In-DTPA-tamoxifen for single photon emission computed tomography (SPECT) evaluation of breast cancer. If $^{111}$In=DTPA-tamoxifen binding with tumors is detected by SPECT, then this may predict response of tamoxifen/retinoic acid combination therapy for breast cancer.

Concentrations of serum selenium and antioxidants were increased significantly in patients treated with tamoxifen (3–6 months). Tamoxifen therapy may thus exert positive effects on the rate of lipid peroxidation and protective systems in postmenopausal women with breast cancer. In cancer, requirements for vitamins/antioxidants increase progressively. Therefore, levels of vitamins decreased in women with untreated breast cancer compared to normals. Combining antioxidants, Vitamin A and tamoxifen, would improve tamoxifen efficacy in breast cancer therapy, since they prevent lipid peroxidation. Reports indicate that tamoxifen efficacy increases when 13-cis-retinoic acid and tamoxifen are combined. No report attempts to predict the response of breast cancer to tamoxifen therapy.

To date, 10 patients have been imaged with ER+ breast tumors using $^{18}$F-tamoxifen by positron emission tomography (PET). Eight of 10 patients received tamoxifen therapy after PET. Three patients who responded well to tamoxifen therapy showed standardized uptake value (SUV) >2.4 in the tumor, whereas 4/5 patients who responded poorly to tamoxifen therapy showed SUV <2.0 in the lesion. PET-[$^{18}$F] fluorotamoxifen provides useful information in predicting effect of tamoxifen therapy in patients with recurrent or metastatic ER+ breast cancer.

The study will be conducted in three phases: 1) DTPA-tamoxifen will be synthesized. An estrogen receptor assay and biodistribution of DTPA-tamoxifen will be performed. 2) The dose and time effect of cis-retinoic acid therapy on uptake of $^{111}$In=DTPA-tamoxifen will be conducted in breast tumor-bearing mice, and 3) Breast tumor response to tamoxifen and cis-retinoic acid combination therapy will be evaluated. Statistical analysis of tumor size, weight and tumor estrogen receptor density among tamoxifen, cis-retinoic acid, and combination before and after breast cancer therapy will be correlated.

This presently described screening methods should improve monitoring of breast cancer treatment using $^{111}$In-DTPA-tamoxifen, as well as aldehyde or multiple aldehyde analogs of tamoxifen.

Eight of 10 patients received tamoxifen therapy after the PET study. Three patients who had a good response to tamoxifen therapy showed a standardized uptake value of [$^{18}$F]fluorotamoxifen of more than 2.4 in the tumor, whereas four of five patients who had a poor response to tamoxifen therapy showed a standardized uptake value of [$^{18}$f] fluorotamoxifen of less than 2.0 in the lesion. PET imaging using [$^{18}$f]fluorotamoxifen as the radiotracer provides useful information in predicting the effect of tamoxifen therapy in patients with recurrent or metastatic ER-positive breast cancer. Tamoxifen analogues for single photon emission computed tomography (SPECT) evaluation of breast cancer have also been developed.

Where the binding of tamoxifen to tumors can be detected with a SPECT tamoxifen radiotracer, then such a radiotracer may predict the response of tamoxifen and retinoic acid therapy for breast cancer. Also, the combination of tamoxifen and retinoic acid may produce synergetic efficacy by suppressing the breast tumor cell growth, as both compounds actively inhibit tumor cell proliferation. $^{111}$In DTPA-tamoxifen will be used to monitor 13-cis-retinoic acid and tamoxifen combined therapy in breast cancer animal models.

The data obtained from this study should provide an impact on improving the diagnosis and monitoring of the treatment of breast cancer through the application of a combined mixture of tamoxifen and Vitamin A.

The present invention provides a method for diagnosing and monitoring the treatment of breast cancer comprising administering to a patient suspected of having breast cancer a composition comprising tamoxifen and Vitamin A. Of course, other vitamins (e.g., Vitamin C and E) may be included together with or instead of Vitamin A in the practice of the claims method. In some embodiments, the tamoxifen is further defined as a DTPA-tamoxifen.

The present invention also contemplates a combination of tamoxifen analogs, such as DTPA-tamoxifen, with chemotherapeutic agents and/or chelating agents. The invention has further application as an estrogen receptor screen-in this manner, a patient having a tumor may first be tested with the analogs of the invention (e.g., DTPA-TX) to determine if the tumors will take up the analog. Where a tissue does demonstrate uptake an estrogen receptor positive tissue that has been determined to take up tamoxifen will have been identified, and a clinical protocol of chemotherapeutic agents may then be applied to the patient, with a greater probability of tissue uptake and likely response/effective. For example, the above described screen would be conducted on a patient prior to making the further clinical decision to treat the patient with taxol, a recognized chemotherapeutic agent. In essence, the methods employ a paramagnetic material or radionucleotide test, using the tamoxifen derivatives, in an assay to identify the specificity and effectiveness of a particular drug response.

DTPA represents a 4 carbonyl containing agent. It constitutes only one example of the substances that may be used as part of the herein disclosed amino tamoxifen conjugates. Other multiple-limbed chelating agents that have different carbonyl lengthsmay be used in the practice of the invention. For use in MRI, the tamoxifen can be chelated with iron, magnesium, or gadmalinium.

The following references are specifically incorporated herein by reference in pertinent part for the reasons indicated herein.

BIBLIOGRAPHY

1. T. Nogrady (1985), *Medicinal Chemistry: A Biochemistry Approach*, Oxford University Press, New York, pp. 210–19.
2. Robertson et al. (1982), *J. Org. Chem.*, 47:2387–93.
3. Kallio et al. (1986), *Cancer Chemother Pharmacol.*, 17:103–8.
4. Mintun et al. (1988), *Radiology*, 169:45–8.
5. Hamacher et al. (1986), *J. Nucl. Med.*, 27(2):235–8.
6. Foster et al. (1986), *Anticancer Drug Design*, 1:245–57.
7. Still et al. (1978), *J. Orn. Chem.*, 43:2923–4.
8. Foster et al. (1985), *J. Med. Chem.*, 28:1491–7.
9. Wieland et al. (1988), *Int. Rad. J. Appl. Instrum.* [A], 39:1219–25.
10. J. H. Fishman (1983), *Biochem. Biophys. Res. Commun.*, pp. 713–18.
11. McCague et al. (1988), *J. Med. Chem.*, 31:1285–90.
12. Lowry et al. (1951), *J. Biol. Chem.*, 193:265–75.
13. U.S. Pat. No. 4,839,155—McCague (1989)
14. U.S. Pat. No. 3,288,806—Dewald (1966)
15. Allen et al. (1980), *British Journal of Pharmacology*, 71:83–91.
16. Pomper et al. (1988), *J. Med. Chem.*, 31(7):1360–63.
17. Kiesewetter et al. (1984), *J. Organ. Chem.*, 49:4900.
18. Fur et al. (1984), *Pharmac. Ther.*, 25:127.
19. Kiesewetter et al. (1984) *J. Nucl. Med.*, 25:1212–1221.
20. Hochberg, R. B. (1979) *Science*, 205:1138–1140.
21. Katzenellenbogen et al. (1981), *J. Nucl. Med.*, 22:42–97.
22. Shani et al. (1985) *J. Med. Chem.*, 28:1504–1511.
23. Hanson et al. (1982), *Int. J. Nucl. Med. Biol.*, 9:105–107.
24. Kallio et al (1986) *Cancer Chemotherapy and Pharmacology*, 17:103–108.
25. Kuroda et al (1985) *J. Med. Chem*, 28:1497–1503.
26. DeGregorio et al (1987) *Cancer Chemother. Pharmacol.*, 20:316–318.
27. Yang et al (1991) *Pharmaceutical Research*, 8(2):174–177.
28. Ram et al (1989) *Journal of Labelled Compounds and Radiopharmaceuticals*, 27(6):601–668.
29. Katzenellenbogen et al (1984) *Cancer Research*, 44:112–119.
30. Robertson et al (1982) *J. Org. Chem.* 47:2387–2393.
31. DeGregorio et al (1989) *Cancer Chemother. Pharmacol.*, 23:68–70.
32. Kangas et al (1986) *Cancer Chemother. Pharmacol.*, 17:109–113.
33. Foster et al (1985) *J. Med. Chem.*, 28 (10):1491–1497.
34. Armstrong (1987) *J. of Chromatography*, 414:192–196.
35. Lien et al (1987) *Clin. Chem.*, 33(9):1608–1614.
36. Mosman, T. (1983) *J. Immunol. Methods*, 65:1608–1614.
37. Salituro et al (1986) *Steroids*, 48(5–6):287–313
38. Shani et al (1985) *J. Med. Chem.*, 28:1504–1511
39. Fernandez M D et al. (1984) *Eur. J. Cancer Clin. Oncol.*, 20:41–46.
40. Wittliff J L, (1984) *Cancer Res.*, 53:630–643.
41. McManaway M E. et al., (1984) *J. Nucl. Med.*, 25:472–477.
42. Jagoda E M et al. (1984) *J. Nucl. Med.*, 25:472–477.
43. Mintun M A et al, (1988) *Radiology* 169:45–50.

44. McGuire A H et al., (1991) *J. Nucl. Med.* 32:1526–1531.
45. Nogrady T., (1985) *Oxford University Press*, 210–219.
46. Kallio S et al., (1986) *Cancer Chemother. Pharmcol.* 17:103–108.
47. Pollack I F et al., (1990) *Cancer Res.*, 50:7134–7138.
48. Hamm J T and Allegra J C, (1991) *Witts RE, ed. Manual of Oncologic Therapeutics*, 122–126.
49. Yang D J et al., (1992) *J. Pharm. Sci.*, 81:622–625.
50. Hamacher K. et al., (1986) *J. Nucl. Med.* 27:235–238.
51. Loser R, et al., (1985) *Eur. J. Cancer Clin. Oncol.*, 21(8):985–990.
52. Foster A B et al., (1985) *J. Med. Chem.*, 28:1491–1497.
53. Robertson D. and Katzenellenbogen J A., (1987) *J. Org. Chem.*, 47:2387–2393.
54. Shani J. et al., (1985) *J. Med. Chem.*, 28:1504–1511.
55. Hanson R N., Seitz D E., (1982) *Int. J. Nucl. Med. Biol.* 9:105–107.
56. Kangas L. et al., (1986) *Cancer Chemother. Pharmacol.* 17:109–113.
57. Katzenellenbogen J A. et al., (1980) *J. Nucl. Med.* 21:550–558.
58. Tsai T-L., Katzenellenbogen B S., (1977) *Cancer Res.* 37:1537–1543.
59. Schneider M R et al., (1982) *J. Med. Chem.* 25:1070–1077.
60. McElvany K D et al., (1982) *J. Nucl. Med.* 23:425–430.
61. Holmes F A et al., (1990) *J. Clin. Oncol.*, 8(6):1025–1035.
62. Maehara Y et al., (1990) *Eur. Surg. Res.*, 22:50–56.
63. Bexwoda V R, (1991) *Cancer*, 68:867–872.
64. Fernandes B J et al., (1991) *CJS*, 34:349–355.
65. Wiseman et al. (1993), *Biochem. J.* 292:635–638.
66. Wiseman et al. (1993) *Biochemical Pharmacology*, 45(9): 1851–1855.
67. Lien et al. (1991), *Cancer Research*, 51:4837–4844.
68. Yang et al. (1994), *Life Sci.*, 55:53–67.
69. Chang et al. (1989), *J. Nucl. Med. Biol.*, 16:475–481.
70. Bezwoda et al. (1991) *Cancer*, 68:867–872.
71. Yang D J et al. (1995) *In: EMran AM ed. Chemists' View of Imaging Center*, 513–526.

What is claimed is:

1. An amino tamoxifen analog which is a compound of:

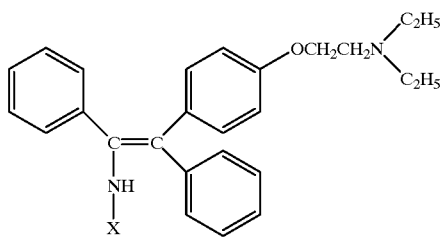

wherein X is an aldehyde.

2. The amino tamoxifen analog of claim 1, further comprising a detectable label.

3. The amino tamoxifen analog of claim 2, wherein the detectable label is $^{111}$In.

4. The amino tamoxifen analog of claim 1 wherein X is DTPA.

5. The amino tamoxifen analog of claim 2, wherein the detectable label is $^{68}$Ga.

6. The amino tamoxifen analog of claim 2, wherein the detectable label is $^{99m}$Tc.

7. The amino tamoxifen analog of claim 2, wherein the detectable label is $^{90}$Y.

8. The amino tamoxifen analog of claim 2, wherein the detectable label is $^{188}$Re.

9. The amino tamoxifen analog of claim 2, wherein the detectable label is $^{56}$Fe.

10. The amino tamoxifen analog of claim 2, wherein the detectable label is $^{55}$Mn.

11. The amino tamoxifen analog of claim 2, wherein the detectable label is $^{157}$Gd.

12. The amino tamoxifen analog of claim 2, wherein the detectable label is $^{121}$I.

13. The amino tamoxifen analog of claim 2, wherein the detectable label is $^{131}$I.

14. The amino tamoxifen analog of claim 2, wherein the detectable label is $^{18}$F.

15. The amino tamoxifen analog of claim 2, wherein the detectable label is $^{77}$Br.

16. The amino tamoxifen analog of claim 2, wherein the detectable label is $^{75}$Br.

17. The amino tamoxifen analog of claim 2, wherein the detectable label is $^{11}$CH$_3$I.

18. The amino tamoxifen analog of claim 2, wherein the detectable label is $^{111}$InCl$^3$.

19. The amino tamoxifen analog of claim 2, wherein the detectable label is $^{111}$InCl$^{333}$.

20. A pharmaceutical agent having binding affinity for an estrogen receptor comprising an amino tamoxifen analog and a detectable label bonded to an alkyl chain of said amino tamoxifen analog, wherein the analog has the structure:

21. The pharmaceutical agent of claim 20 wherein the detectable label is $^{111}$In.

22. The pharmaceutical agent of claim 20, wherein the detectable label is $^{68}$Ga.

23. The pharmaceutical agent of claim 20, wherein the detectable label is $^{99m}$Tc.

24. The pharmaceutical agent of claim 20, wherein the detectable label is $^{90}$Y.

25. The pharmaceutical agent of claim 20, wherein the detectable label is $^{188}$Re.

26. The pharmaceutical agent of claim 20, wherein the detectable label is $^{56}$Fe.

27. The pharmaceutical agent of claim 20, wherein the detectable label is $^{55}$Mn.

28. The pharmaceutical agent of claim 20, wherein the detectable label is $^{157}$Gd.

29. The pharmaceutical agent of claim 20, wherein the detectable label is $^{121}$I.

30. The pharmaceutical agent of claim 20, wherein the detectable label is $^{131}$I.

31. The pharmaceutical agent of claim 20, wherein the detectable label is $^{18}$F.

32. The pharmaceutical agent of claim 20, wherein the detectable label is $^{77}$Br.

33. The pharmaceutical agent of claim 20, wherein the detectable label is $^{75}$Br.

34. The pharmaceutical agent of claim 20, wherein the detectable label is $^{11}CH_3I$.

35. The pharmaceutical agent of claim 20, wherein the detectable label is $^{111}InCl^3$.

36. The pharmaceutical agent of claim 20, wherein the detectable label is $^{111}InCl^{333}$.

37. A pharmaceutical agent having anti-tumor activity against an estrogen hormone-dependent tumor comprising an amino tamoxifen DTPA analog, wherein the analog has the structure:

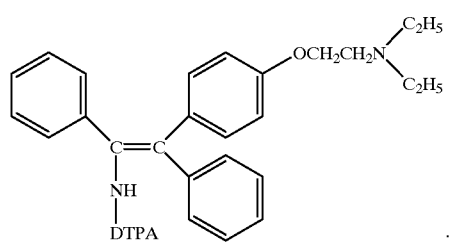

* * * * *

UNITED STATES PATENT AND TRADEMARK OFFICE
CERTIFICATE OF CORRECTION

PATENT NO. : 6,096,874
DATED : August 1, 2000
INVENTOR(S) : Wallace et al.

It is certified that error appears in the above-identified patent and that said Letters Patent is hereby corrected as shown below:

On the title page:

In item [75], Inventors, please delete "E. Delpassand, Bellaire; A. Cherif, Houston; S. Quadri, Houston" and insert --Ebrahim Delpassand, Bellaire; Abdallah Cherif, Houston; Syed M. Quadri -- therefor.

In item [63], Related U.S. Application Data, the third line, please delete "Oct. 11, 1990" and insert -- Oct 1, 1990 -- therefor.

In claim 18, column 78, line 21, please delete "$^{111}InCl^3$" and insert -- $^{111}InCl_3$ -- therefor.

In claim 19, column 78, line 23, please delete "$^{111}InCl^{333}$" and insert -- $^{111}InCl_3^{33}$ -- therefor.

In claim 35, column 79, line 5, please delete "$^{111}InCl^3$" and insert -- $^{111}InCl_3$ -- therefor.

In claim 36, column 79, line 7, please delete "$^{111}InCl^{333}$" and insert -- $^{111}InCl_3^{33}$ -- therefor.

Signed and Sealed this

Twenty-second Day of May, 2001

Attest:

NICHOLAS P. GODICI

Attesting Officer

Acting Director of the United States Patent and Trademark Office